United States Patent
Vann et al.

(10) Patent No.: US 7,323,696 B2
(45) Date of Patent: Jan. 29, 2008

(54) PHOSPHOR PARTICLE CODED BEADS

(75) Inventors: Charles S. Vann, Burlingame, CA (US); Charles R. Connell, Redwood City, CA (US); Aldrich N. K. Lau, Palo Alto, CA (US); Meng C. Taing, Hayward, CA (US); Steven M. Menchen, Fremont, CA (US)

(73) Assignee: Applera Corporation, Foster City, CA (US)

( * ) Notice: Subject to any disclaimer, the term of this patent is extended or adjusted under 35 U.S.C. 154(b) by 253 days.

(21) Appl. No.: 11/031,983

(22) Filed: Jan. 6, 2005

(65) Prior Publication Data

US 2005/0208543 A1    Sep. 22, 2005

Related U.S. Application Data

(60) Provisional application No. 60/535,427, filed on Jan. 9, 2004.

(51) Int. Cl.
*G01N 21/64* (2006.01)
*G21K 5/00* (2006.01)

(52) U.S. Cl. .............. 250/458.1; 250/459.1; 250/461.1; 250/461.2

(58) Field of Classification Search ............ 250/458.1, 250/459.1, 461.1, 461.2
See application file for complete search history.

(56) References Cited

U.S. PATENT DOCUMENTS

| | | | |
|---|---|---|---|
| 6,498,016 B1 * | 12/2002 | Nahar et al. ............... | 435/7.92 |
| 6,548,264 B1 | 4/2003 | Tan et al. | |
| 6,831,279 B2 * | 12/2004 | Ho ........................... | 250/458.1 |
| 2002/0028457 A1 | 3/2002 | Empedocles et al. | |
| 2003/0207331 A1 * | 11/2003 | Wilson et al. .............. | 435/7.1 |
| 2004/0048390 A1 * | 3/2004 | Wang et al. ................ | 436/172 |

FOREIGN PATENT DOCUMENTS

| | | |
|---|---|---|
| EP | 0 354 847 A2 | 2/1990 |
| EP | 1 249 502 A2 | 10/2002 |
| JP | 2001249131 | 9/2001 |

(Continued)

OTHER PUBLICATIONS

Invitation to Pay Additional Fees and Communication Relating to the Results of the Partial International Search dated Oct. 12, 2005, for Application No. PCT/US2005/000006.

PCT Notification of Transmittal of the International Search Report and the Written Opinion of the International Searching Authority, or the Declaration, dated Dec. 12, 2005, for Application No. PCT/US2005/000006.

Notification Concerning Transmittal of Copy of International Preliminary Report on Patentability (Chapter 1 of the Patent Cooperation Treaty) and Written Opinion of the International Searching Authority, mailed Jul. 20, 2006, for International Application No. PCT/US2005/000006.

*Primary Examiner*—David Porta
*Assistant Examiner*—Mindy Vu
(74) *Attorney, Agent, or Firm*—Finnegan, Henderson, Farabow, Garrett & Dunner, LLP; Scott R. Bortner

(57) ABSTRACT

Beads coded with phosphor particles and methods of making and using them are provided.

13 Claims, 18 Drawing Sheets bead pairs, two binary colors per bead: 16 codes

FOREIGN PATENT DOCUMENTS

| | | |
|---|---|---|
| WO | WO 94/07142 | 3/1994 |
| WO | WO 98/53093 | 11/1998 |
| WO | WO 99/19515 | 4/1999 |
| WO | WO 00/29617 A2 | 5/2000 |
| WO | WO 00/29617 A3 | 5/2000 |
| WO | WO 02/04527 A2 | 1/2002 |
| WO | WO 02/35228 A2 | 5/2002 |
| WO | WO 03/003015 A2 | 1/2003 |

* cited by examiner

A individual beads, two binary colors: 4 codes

B individual beads, three binary colors: 8 codes

C individual beads, two ternary colors: 9 codes bead pairs, two binary colors per bead: 16 codes

Normal Emulsion Polymerization in the Presence of Reactive Dyes

Core/Shell Microencapsulation of Dyes

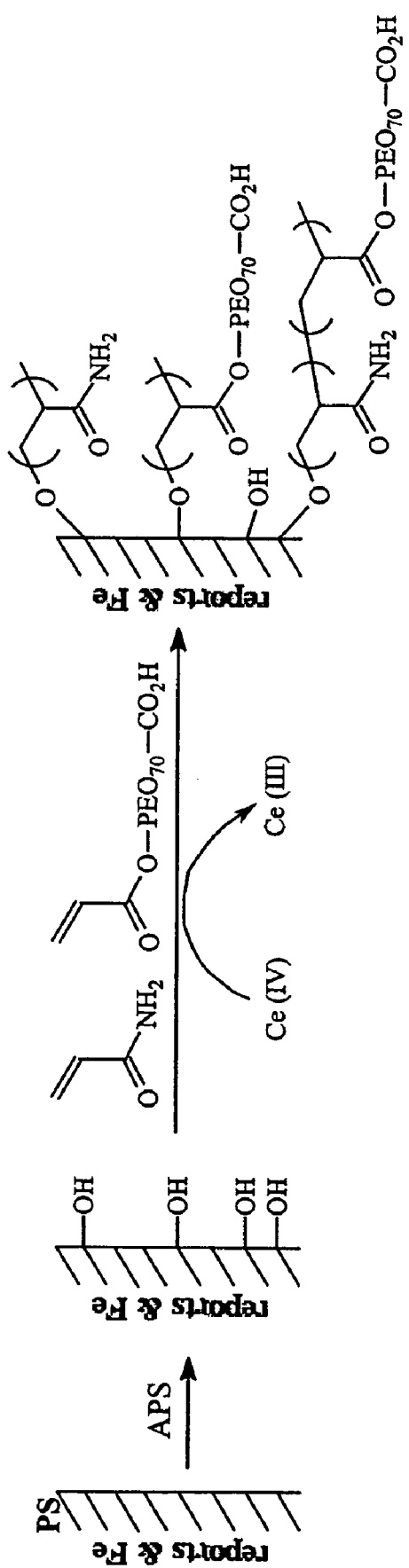
Fig. 15. Surface grafting based on free radical polymerization

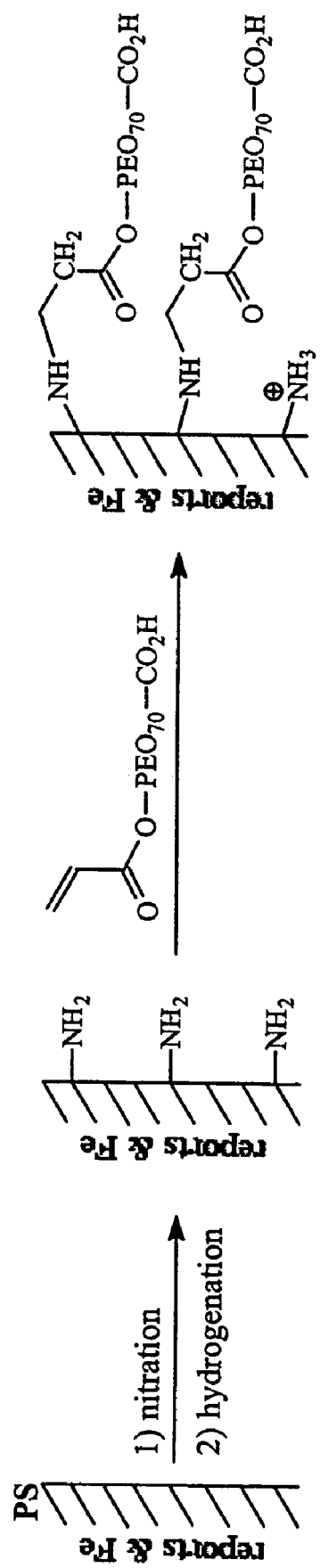
Fig. 16. Surface modification via Michael Addition

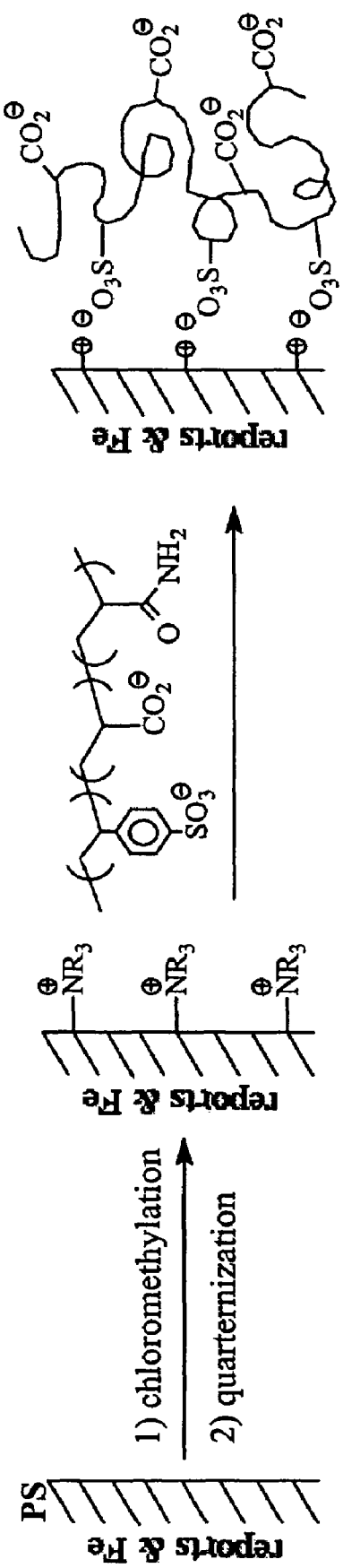
Fig. 17. Surface modification via ionic interaction

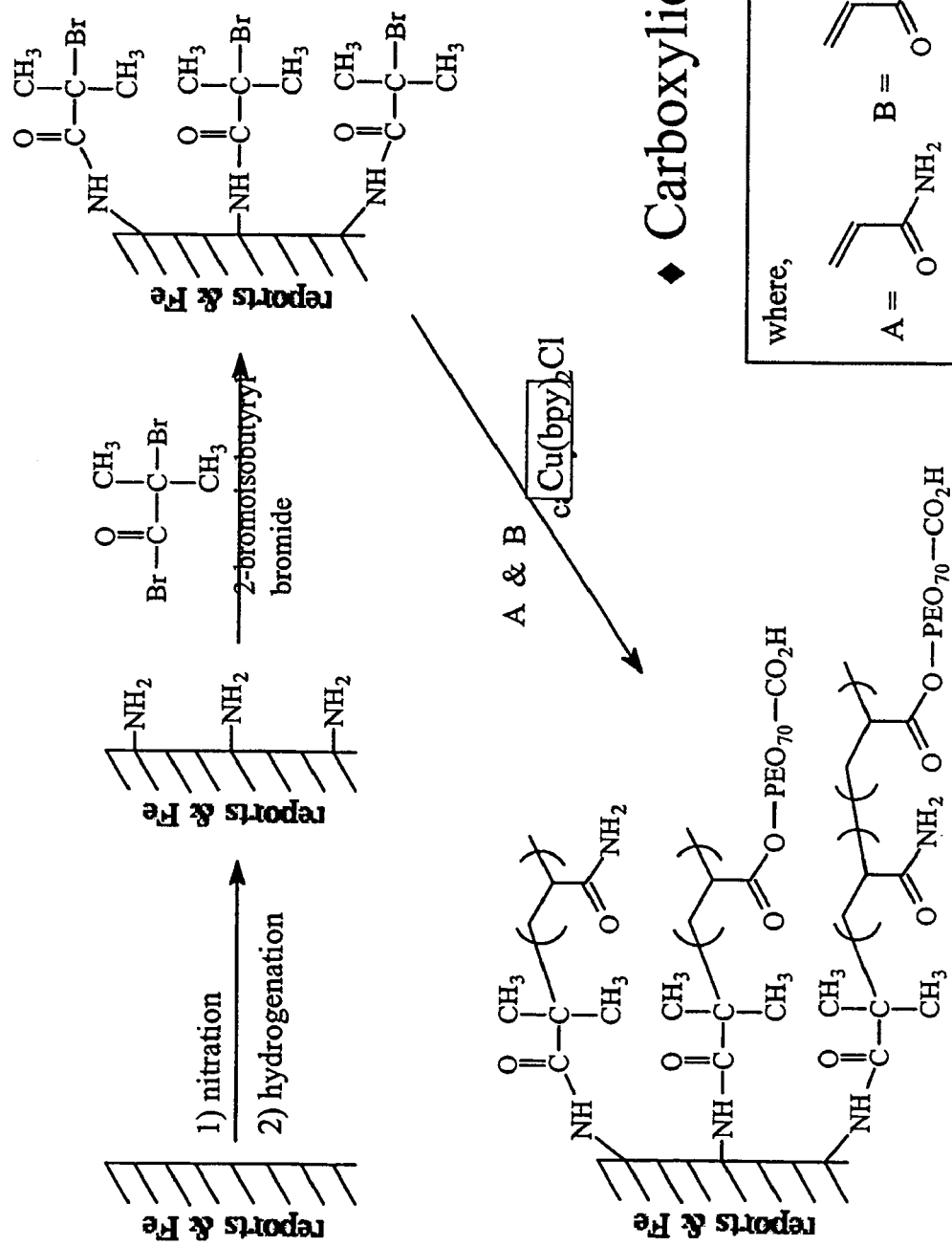
Fig. 18. Surface grafting via Atom Transfer Radical Polymerization

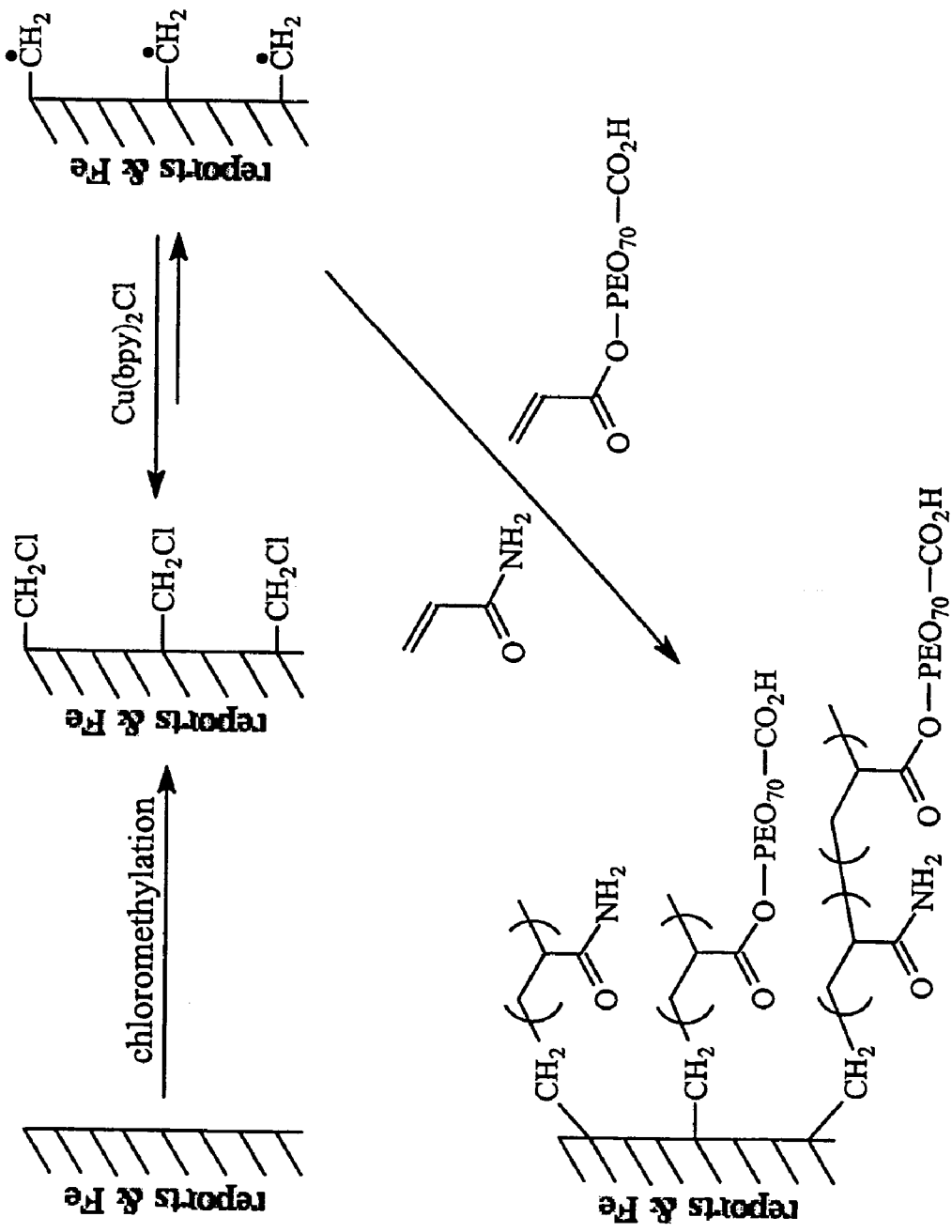
Fig. 19. Surface Initiated Living Radical Polymerization

Figure 20. Surface Modification of Polymer Beads by Poly(ethylene oxide)
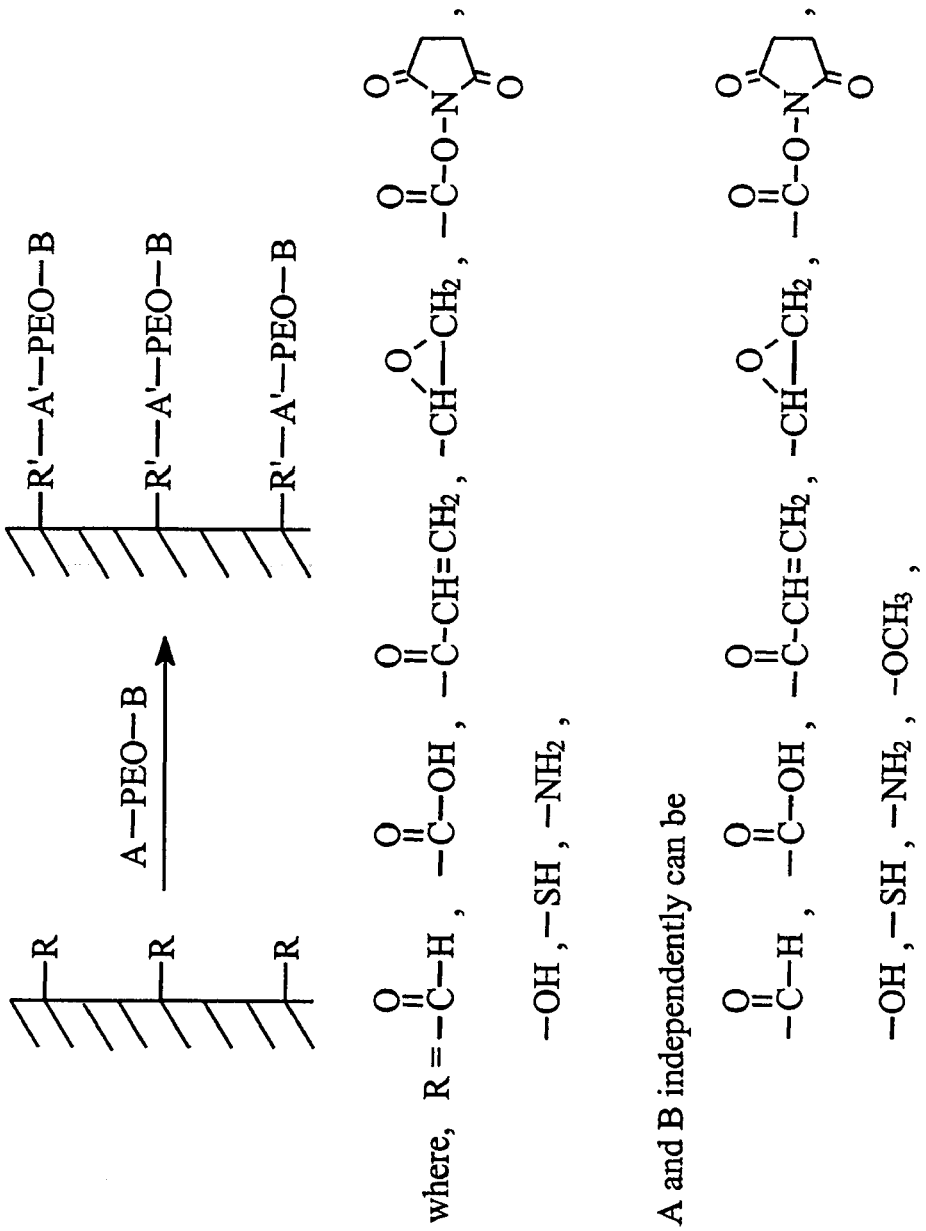

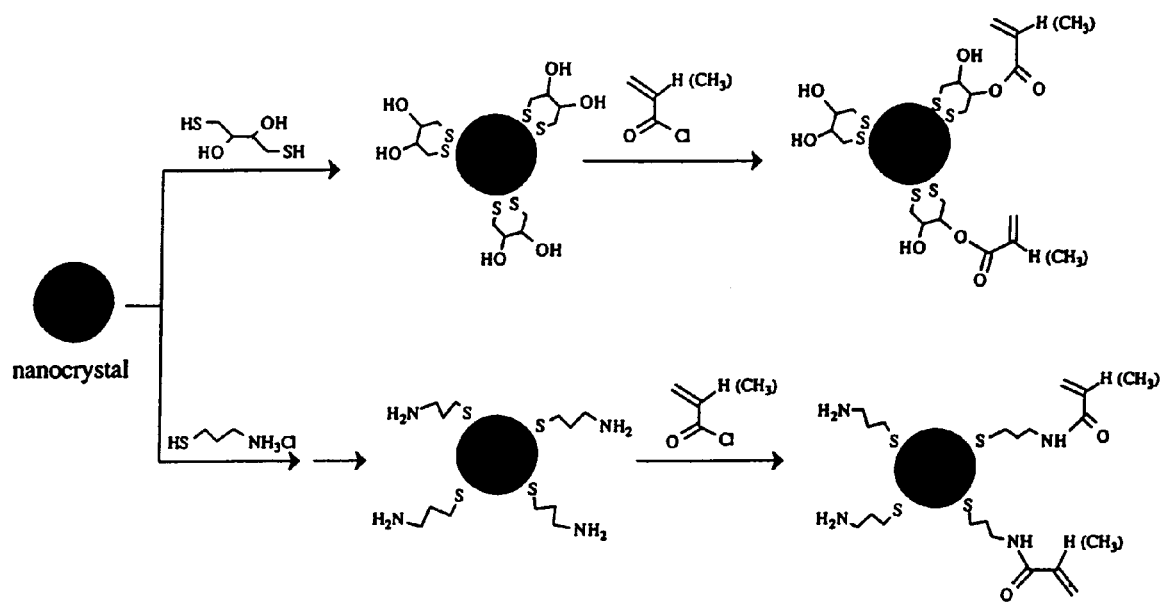
Figure 21. Surface modification of Nanocrystal and phosphor

PHOSPHOR PARTICLE CODED BEADS

This application claims the benefit of U.S. Provisional Application No. 60/535,427, filed Jan. 9, 2004. U.S. Provisional Application No. 60/535,427 is incorporated by reference herein for any purpose.

FIELD OF THE INVENTION

Certain embodiments of the invention relate to beads coded with phosphor particles. Certain embodiments relate to methods of making beads coded with phosphor particles. Certain embodiments relate to methods of using beads coded with phosphor particles.

BACKGROUND

Beads with a detectable signal or code may be used in a variety of applications. For example, one can detect the presence or absence of one or more targets in a sample using beads.

SUMMARY OF THE INVENTION

In certain embodiments, a bead comprising a substrate and two or more different phosphor particles is provided. In certain embodiments, each of the two or more different phosphor particles is capable of producing a different detectable signal.

In certain embodiments, at least one of the different detectable signals comprises light comprising at least one wavelength in the visible spectrum. In certain embodiments, at least one of the different detectable signal comprises light comprising at least one wavelength between 380 nm and 720 nm.

In certain embodiments, the two or more different phosphor particles emit light at wavelengths shorter than a wavelength capable of exciting the two or more different phosphor particles. In certain embodiments, at least one of the two or more different phosphor particles emits light at a wavelength shorter than a wavelength capable of exciting the at least one of the two or more different phosphor particles. In certain embodiments, the two or more different phosphor particles emit light at wavelengths longer than a wavelength capable of exciting the two or more different phosphor particles. In certain embodiments, at least one of the two or more different phosphor particles emits light at a wavelength longer than a wavelength capable of exciting the at least one of the two or more different phosphor particles.

In certain embodiments, the two or more different phosphor particles comprise at least one phosphor particle that emits light at a wavelength shorter than a wavelength capable of exciting the two or more different phosphor particles and at least one phosphor particles that emits light at a wavelength longer than a wavelength capable of exciting the two or more different phosphor particles.

In certain embodiments, a bead comprising a substrate and two or more different phosphor particles, wherein at least one first phosphor particle, when excited by a first wavelength of light, emits a second wavelength of light; and wherein at least one second phosphor particle, when excited by a third wavelength of light, emits the second wavelength of light, is provided.

In certain embodiments, the first wavelength of light is a wavelength of light in the visible spectrum. In certain embodiments, the first wavelength of light is between 380 nm and 720 nm. In certain embodiments, the second wavelength of light is shorter than the first wavelength of light and wherein the third wavelength of light is longer than the first wavelength of light.

In certain embodiments, the substrate is at least one substrate selected from glass, metal, and an organic polymer. In certain embodiments, the two or more different phosphor particles are distributed throughout the substrate. In certain embodiments, the two or more different phosphor particles are homogeneously distributed throughout the substrate. In certain embodiments, the two or more different phosphor particles are attached to the surface of the bead.

In certain embodiments, a method of determining the identity of a bead comprising two or more different phosphor particles is provided. In certain embodiments, a method of determining the identity of a bead comprising at least one phosphor particle and at least one quantum dot particle is provided. In certain embodiments, the method comprises irradiating the bead with at least one irradiating wavelength of light, wherein the at least one irradiating wavelength of light causes at least one particle to emit at least one emitting wavelength of light; detecting the at least one emitting wavelength of light; and determining the identity of the bead. In certain embodiments, the method further comprises repeating the irradiating and detecting 1 to 20 times. In certain embodiments, at least one of the at least one irradiating wavelength of light for each repetition is the same or different from at least one of the at least one irradiating wavelength of light for any previous irradiating of the bead. In certain embodiments, at least one of the at least one emitting wavelength of light for each repetition is the same or different from at least one of the at least one emitting wavelength of light for any previous emission by a phosphor particle.

In certain embodiments, a method of determining the identity of a bead comprising at least two different phosphor particles is provided. In certain embodiments, a method of determining the identity of a bead comprising a substrate and at least two different particles, wherein each of the at least two different particles is selected from a phosphor particle and a quantum dot particle, and wherein the bead comprises at least one phosphor particle and at least one quantum dot particle, is provided. In certain embodiments, the method comprises irradiating the bead with at least one first irradiating wavelength of light, wherein the at least one first irradiating wavelength of light causes a first particle to emit a first emitting wavelength of light; detecting at least the first emitting wavelength of light; irradiating the bead with at least one second irradiating wavelength of light, wherein the at least one second irradiating wavelength of light causes a second particle to emit the first emitting wavelength of light; detecting at least the first emitting wavelength of light; and determining the identity of the bead.

In certain embodiments, the method further comprises repeating the irradiating with at least one first irradiating wavelength of light, detecting the at least the first emitting wavelength of light, irradiating with at least one second irradiating wavelength of light, and detecting at least the first emitting wavelength of light 1 to 20 times, wherein at least one of the at least one first irradiating wavelength of light for each repetition is the same or different from at least one of the at least one first irradiating wavelength of light of any previous irradiation of the bead, wherein at least one of the at least one second irradiating wavelength of light for each repetition is the same or different from at least one of the at least one second irradiating wavelength of light of any previous irradiation of the bead, and wherein the first emitting wavelength of light for each repetition is the same or different from the first emitting wavelength of light of any previous emission by a phosphor particle.

In certain embodiments, the method further comprises irradiating the bead with at least one third irradiating wavelength of light, wherein the at least one third irradiating wavelength of light causes at least one third phosphor particle to emit at least one second emitting wavelength of light; and detecting the at least one second emitting wavelength of light. In certain embodiments, the method further comprises repeating the irradiating with at least one third irradiating wavelength of light and the detecting the at least one second emitting wavelength of light 1 to 20 times, wherein at least one of the at least one third irradiating wavelength of light for each repetition is the same or different from at least one of the at least one third irradiating wavelength of light of any previous irradiating of the bead, and at least one of the at least one second emitting wavelength of light for each repetition is the same or different from at least one of the at least one second emitting wavelength of light of any previous emission by a phosphor particle.

In certain embodiments, at least one of the at least one emitting wavelength of light comprises light in the visible spectrum. In certain embodiments, at least one of the at least one emitting wavelength of light is between 380 nm and 720 nm.

In certain embodiments, a kit comprising two or more different coded beads is provided. In certain embodiments, each different coded bead comprises a substrate; and two or more different phosphor particles, wherein each of the two or more different phosphor particles is capable of producing a different detectable signal; and wherein each different coded bead is distinguishable from other different coded beads by the detectable signals each bead emits.

In certain embodiments, a kit comprising two or more different coded beads is provided. In certain embodiments, at least one coded bead comprises a substrate; and two or more different phosphor particles, wherein at least one first phosphor particle emits a first wavelength of light when excited by a second wavelength of light and at least one second phosphor particle emits the first wavelength of light when excited by a third wavelength of light.

In certain embodiments, the two or more different coded beads comprises at least 10 different coded beads. In certain embodiments, each bead comprises at least one member of an affinity set, wherein at least one of the at least one member of the affinity set is selected from a polynucleotide, a polypeptide, a polysaccharide, streptavidin, biotin, a ligand, an antigen, and an antibody.

In certain embodiments, a method of determining the presence or quantity of at least one target in a sample is provided. In certain embodiments, the method comprises forming a mixture comprising at least one coded bead and a sample potentially containing at least one target. In certain embodiments, each coded bead comprises a substrate; two or more different phosphor particles, wherein each phosphor particles is capable of producing a detectable signal; and at least one target specific binding molecule. In certain embodiments, the method further comprises allowing at least one of the at least one target specific binding molecule to bind at least one of the at least one target; and identifying at least one of the at least one coded beads and determining the presence or quantity of at least one of the at least one target bound to at least one of the at least one coded beads.

In certain embodiments, the at least one target is at least two different targets. In certain embodiments, the at least one coded bead is two or more different coded beads. In certain embodiments, each of the two or more different coded beads comprises a different target specific binding molecule.

In certain embodiments, a bead comprising a substrate, at least one phosphor particle and at least one quantum dot particle is provided. In certain embodiments, each phosphor particle produces a different signal than each quantum dot particle.

In certain embodiments, the substrate is at least one substrate selected from glass, metal, and an organic polymer. In certain embodiments, at least one of the at least one phosphor particle and at least one of the at least one quantum dot particle are distributed throughout the bead. In certain embodiments, at least one of the at least one phosphor particle and at least one of the at least one quantum dot particle are attached to the surface of the bead. In certain embodiments, at least one of the at least one phosphor particle is distributed throughout the bead and at least one of the at least one quantum dot particle is attached to the surface of the bead. In certain embodiments, at least one of the at least one quantum dot particle is distributed throughout the bead and at least one of the at least one phosphor particle is attached to the surface of the bead.

In certain embodiments, at least one phosphor particle emits a first wavelength of light when excited by a second wavelength of light and at least one quantum dot particle emits the first wavelength of light when excited by a third wavelength of light. In certain, the first wavelength of light comprises a wavelength in the visible spectrum. In certain embodiments, the first wavelength of light comprises a wavelength between 380 nm and 720 nm.

In certain embodiments, a method of making a bead is provided. In certain embodiments, the method comprises forming an inverse emulsion comprising an oil phase and an aqueous phase, wherein the aqueous phase comprises at least one monomer and at least one phosphor particle; and initiating polymerization. In certain embodiments, the method comprises forming an inverse emulsion comprising an oil phase and an aqueous phase, wherein the aqueous phase comprises at least one monomer, at least one phosphor particle, and at least one quantum dot particle; and initiating polymerization.

In certain embodiments, the aqueous phase further comprises at least one crosslinker. In certain embodiments, the initiating polymerization comprises adding to the inverse emulsion at least one initiator selected from a free-radical initiator, a cationic initiator, and an anionic initiator. In certain embodiments, the initiating polymerization comprises exposing the inverse emulsion to at least one initiator selected from an electron beam, ultraviolet radiation, x-ray radiation, y radiation, and fast neutrons.

In certain embodiments, a method of making a bead is provided. In certain embodiments, the method comprises forming an emulsion comprising an oil phase and an aqueous phase, wherein the oil phase comprises at least one monomer and at least one phosphor particle; and initiating polymerization. In certain embodiments, the method comprises forming an emulsion comprising an oil phase and an aqueous phase, wherein the oil phase comprises at least one monomer, at least one phosphor particle, and at least one quantum dot particle; and initiating polymerization.

In certain embodiments, the oil phase further comprises at least one crosslinker. In certain embodiments, the initiating polymerization comprises adding to the emulsion at least one initiator selected from a free-radical initiator, a cationic initiator, and an anionic initiator. In certain embodiments, the initiating polymerization comprises exposing the emulsion to at least one initiator selected from an electron beam, ultraviolet radiation, x-ray radiation, Y radiation, and fast neutrons.

In certain embodiments, a bead is provided. In certain embodiments, the bead comprises a substrate; at least one first label that emits a first wavelength of light when excited by a second wavelength of light; and at least one second label that emits the first wavelength of light when excited by a third wavelength of light.

In certain embodiments, the second wavelength of light is longer than the first wavelength of light and the third wavelength of light is shorter than the first wavelength of light. In certain embodiments, the first wavelength of light comprises light in the visible spectrum. In certain embodiments, the first wavelength of light is between 380 nm and 720 nm.

In certain embodiments, the substrate is at least one substrate selected from glass, metal, and an organic polymer. In certain embodiments, at least one of the at least one first label and at least one of the at least one second label is distributed throughout the bead. In certain embodiments, at least one of the at least one first label and at least one of the at least one second label is attached to the surface of the bead. In certain embodiments, at least one of the at least one first label is distributed throughout the bead and at least one of the at least one second label is attached to the surface of the bead.

In certain embodiments, a method of determining the identity of a bead comprising a substrate and at least two labels is provided. In certain embodiments, the method comprises (1) irradiating the bead with at least one first irradiating wavelength of light, wherein the at least one first irradiating wavelength of light causes a first label to emit a first emitting wavelength of light. In certain embodiments, the method further comprises (2) detecting at least the first emitting wavelength of light. In certain embodiments, the method further comprises (3) irradiating the bead with at least one second irradiating wavelength of light, wherein the at least one second irradiating wavelength of light causes a second label to emit the first emitting wavelength of light. In certain embodiments, the method further comprises (4) detecting at least the first emitting wavelength of light. In certain embodiments, the method comprises determining the identity of the bead.

In certain embodiments, the method further comprises repeating (1) through (4) 1 to 20 times, wherein at least one of the at least one first irradiating wavelength of light for each repetition is the same or different from at least one of the at least one first irradiating wavelength of light of any previous irradiating of the bead, wherein at least one of the at least one second irradiating wavelength of light for each repetition is the same or different from at least one of the at least one second irradiating wavelength of light of any previous irradiating of the bead, and wherein the first emitting wavelength of light for each repetition is the same or different from the first emitting wavelength of light of any previous emission by a label.

In certain embodiments, the method further comprises irradiating the bead with at least one third irradiating wavelength of light, wherein the at least one third irradiating wavelength of light causes at least one third label to emit at least one second emitting wavelength of light; and detecting at least one of the at least one second emitting wavelength of light. In certain embodiments, the method further comprises repeating the irradiating with at least one third irradiating wavelength of light and detecting at least one of the at least one second emitting wavelength of light 1 to 20 times, wherein at least one of the at least one third irradiating wavelength of light for each repetition is the same or different from at least one of the at least one third irradiating wavelength of light of any previous irradiating of the bead, and wherein at least one of the at least one second emitting wavelength of light for each repetition is the same or different from at least one of the at least one second emitting wavelength of light of any previous emission by a label.

In certain embodiments, a bead comprising a substrate, at least one phosphor particle and at least one non-phosphor particle label is provided. In certain embodiments, each of the at least one non-phosphor particle label is selected from a fluorescent molecule, a dye, a radioisotope, a luminescent molecule, a quantum dot, a gold particle, a resonance light scattering particle, and porous silicon smart dust. In certain embodiments, at least one of the at least one non-phosphor particle label is selected from a dye, a fluorescent molecule, and a luminescent molecule. In certain embodiments, at least one of the at least one non-phosphor particle label is encapsulated in a microbead. In certain embodiments, each phosphor particle produces a different signal than each non-phosphor particle label.

In certain embodiments, the substrate is at least one substrate selected from glass, metal, and an organic polymer. In certain embodiments, at least one of the at least one phosphor particle and at least one of the at least one non-phosphor particle label are distributed throughout the bead. In certain, at least one of the at least one phosphor particle and at least one of the at least one non-phosphor particle label are attached to the surface of the bead. In certain embodiments, at least one of the at least one phosphor particle is distributed throughout the bead and at least one of the at least one non-phosphor particle label is attached to the surface of the bead. In certain, at least one of the at least one non-phosphor particle label is distributed throughout the bead and at least one of the at least one phosphor particle is attached to the surface of the bead.

In certain embodiments, at least one phosphor particle emits a first wavelength of light when excited by a second wavelength of light and at least one non-phosphor particle label emits the first wavelength of light when excited by a third wavelength of light.

In certain embodiments, a method of determining the identity of a bead comprising a substrate and at least two labels, wherein each of the at least two labels is selected from a phosphor particle and a non-phosphor particle label, and wherein the bead comprises at least one phosphor particle and at least one non-phosphor particle label, is provided. In certain embodiments, the method comprises irradiating the bead with at least one irradiating wavelength of light, wherein the at least one irradiating wavelength of light causes at least one label to emit at least one emitting wavelength of light; detecting the at least one emitting wavelength of light; and determining the identity of the bead. In certain embodiments, the method further comprises repeating the irradiating and detecting 1 to 20 times, wherein at least one of the at least one irradiating wavelength for each repetition is the same or different from at least one of the at least one irradiating wavelength for any previous irradiation, and wherein at least one of the at least one emitting wavelength for each repetition is the same or different from at least one of the at least one emitting wavelength for any previous emission by a label.

In certain embodiments, a method of determining the identity of a bead comprising a substrate and at least two labels, wherein each of the at least two labels is selected from a phosphor particle and a non-phosphor particle label, and wherein the bead comprises at least one phosphor particle and at least one non-phosphor particle label, is provided. In certain embodiments, the method comprises (1) irradiating the bead with at least one first irradiating wavelength of light, wherein the at least one first irradiating wavelength of light causes a first label to emit a first emitting wavelength of light. In certain embodiments, the method further comprises (2) detecting at least the first emitting wavelength of light. In certain embodiments, the method further comprises (3) irradiating the bead with at least one second irradiating wavelength of light, wherein the at least one second irradiating wavelength of light causes a second label to emit the first emitting wavelength of light. In certain embodiments, the method further comprises (4) detecting at least the first emitting wavelength of light. In certain embodiments, the method comprises determining the identity of the bead.

In certain embodiments, the method further comprises repeating (1) through (4) 1 to 20 times, wherein at least one of the at least one first irradiating wavelength of light for each repetition is the same or different from at least one of the at least one first irradiating wavelength of light of any previous irradiation of the bead, wherein at least one of the at least one second irradiating wavelength of light for each repetition is the same or different from at least one of the at least one second irradiating wavelength of light of any previous irradiation of the bead, and wherein the first emitting wavelength of light for each repetition is the same or different from the first emitting wavelength of light of any previous emission by a label.

In certain embodiments, the method further comprises irradiating the bead with at least one third irradiating wavelength of light, wherein the at least one third irradiating wavelength of light causes at least one third label to emit at least one second emitting wavelength of light; and detecting the at least one second emitting wavelength of light. In certain embodiments, the method further comprises repeating the irradiating with at least one third irradiating wavelength of light and the detecting the at least one second emitting wavelength of light 1 to 20 times, wherein at least one of the at least one third irradiating wavelength of light for each repetition is the same or different from at least one of the at least one third irradiating wavelength of light of any previous irradiating of the bead, and at least one of the at least one second emitting wavelength of light for each repetition is the same or different from at least one of the at least one second emitting wavelength of light of any previous emission by a label.

In certain embodiments, the bead further comprises at least one moiety by which other substances can be attached to the bead. In certain embodiments, the at least one moiety comprises at least one reactive moiety. In certain embodiments, the at least one moiety comprises at least one member of an affinity set. In certain embodiments, at least one of the at least one moiety is streptavidin. In certain embodiments, at least one of the at least one moiety is a polynucleotide. In certain embodiments, at least one of the at least one moiety is a polypeptide.

BRIEF DESCRIPTION OF THE FIGURES

FIG. 6A shows certain embodiments of beads having two different labels, each of which is either present or absent, i.e., each label is binary. FIG. 6A shows four codes with binary, two-color beads. FIG. 6B shows certain embodiments of beads having three different labels, where each label is either present or absent, i.e., each label is binary. FIG. 6B shows eight codes with binary, three-color beads. FIG. 6C shows certain embodiments of beads having two different labels, each of which can have three different intensities, i.e., each label is ternary. The three different intensities shown in FIG. 6C are (1) two copies of the same label, (2) one copy of the same label, and (3) no copies of the label. FIG. 6C shows nine different codes with ternary, two-color beads.

FIG. 7 shows sixteen codes with the exemplary binary, two-color bead pair. The vertical line between bead 1 and bead 2 of each bead pair is shown solely for purposes of convenience to indicate the bead pairs, and does not necessarily indicate a physical connection between the beads of the bead pair.

FIG. 9(A) shows: (i) two different probe sets comprising coded beads that have different first target-specific probes, A and B, that differ in their pivotal complement (T on probe A and C on probe B), and that have the same second target-specific probe, Z, and (ii) a target sequence, comprising pivotal nucleotide A.

FIG. 9(B) shows the three target-specific probes, attached to different coded beads, annealed to the target. The sequence-specific portion of probe A is fully complementary with the 3' target region including the pivotal nucleotide. The pivotal complement of probe B is not complementary with the 3' target region. The sequence-specific portion of probe B, therefore, contains a base-pair mismatch at the 3' end. The sequence-specific portion of probe Z is fully complementary to the 5' target region.

FIG. 9(C) shows ligation of target-specific probes A and Z, attached to coded beads, to form ligation product A-Z. Probes B and Z are not ligated together to form a ligation product due to the mismatched pivotal complement on probe B.

FIG. 9(D) shows denaturing the double-stranded molecules to release the A-Z ligation product and unligated probes B and Z.

FIG. 15 shows a non-limiting exemplary surface modification of polystyrene beads. The polystyrene beads are hydroxylated in an aqueous solution of ammonium persulfate (APS) at elevated temperature. Surface modification is then carried out using acrylamide and ω-carbonyl(polyethylene oxide)acrylate, molecular weight 3400 (Nektar) in the presence of Ceric(IV)ammonium nitrate in an aqueous solution. See, e.g., Bamford et al., *Macromol. Rapid Commun.*, 14: 379-384 (1994); Bamford et al., *Polymer*, 35: 2844-2852 (1994); Bamford et al., *Polymer*, 37: 4885-4889 (1996); Jabloner et al., *J. Polym. Sci.: A*1, 10:793 (1972); and U.S. Pat. Nos. 3,401,049; 3,698,931; 3,880,580; and 4,810,567; which are incorporated by reference herein for any purpose.

FIG. 16 shows a non-limiting exemplary surface modification of polystyrene beads. Amino groups are introduced onto the surface of the beads by surface nitration with nitric acid and subsequent hydrogenation. The amino groups are then reacted with acrylamide and ω-carboxyl(polyethylene oxide)acrylate, molecular weight 3400 (Nektar). The residual amino groups may be capped, e.g., with an acid anhydride such as acetic anhydride. In certain embodiments, the free amino groups can be converted to free thiol groups by one skilled in the art prior to carrying out the Michael addition reaction, thereby increasing the yield of the Michael addition reaction.

FIG. 17 shows a non-limiting exemplary surface modification of polystyrene beads. The surface of the bead is chloromethylated, e.g., by addition of chloromethyloctyl ether and a catalyst. A non-limiting exemplary catalyst is $SnCl_4$. The surface is then quarternized with a trialkyl amine such as trimethylamine. The resulting positively-charged beads are then coated with a negatively-charged polymer such as a terpolymer prepared by copolymerization of acrylic acid, styrene sulfonic acid, and N,N'-dimethylacrylamide (or acrylamide). The resulting surface-modified bead will have free carboxylic acid groups for conjugation. In certain embodiments, the unconjugated free carboxylic acid groups will reduce passive adsorption of certain biomolecules including, but not limited to, polynucleotides.

FIG. 18 shows a non-limiting exemplary surface modification of polystyrene beads. Amino groups are introduced onto the surface of the beads by surface nitration with nitric acid and subsequent hydrogenation. The surface amino groups are then acylated with 2-bromoisobutyryl bromide. Atom transfer radical polymerization is then initiated, e.g., by a catalyst such as copper 2,2'-dipyridyl chloride to graft acrylamide, N,N-dimethylacrylamide, and/or ω-carboxyl (polyethylene oxide)acrylate, molecular weight 3400 (Nektar), onto the surface of the bead. See, e.g., Truelsen et al., *Polym. Prepr.*, 43: 49 (2002); Jayachandran et al., *Polym. Prepr.*, 43: 65 (2002); and Husson et al., *Polym. Prepr.*, 43: 67 (2002); which are incorporated by reference herein for any purpose. In certain embodiments, the thickness of the grafted polymer can be controlled in order to produce an acrylamide shell over the polystyrene bead core.

FIG. 19 shows a non-limiting exemplary surface modification of polystyrene beads. The surface of the bead is chloromethylated, e.g., using chloromethyloctyl ether in the presence of a catalyst such as $SnCl_4$. Following chloromethylation, acrylamide; N,N-dimethylacrylamide; acrylic acid; poly(ethylene glycol)methyl ether acrylate; ω-carboxyl(polyethylene oxide)acrylate, molecular weight 3400 (Nektar); or a combination thereof may be grafted onto the surface of the bead in the presence of a catalyst such as, for example, copper 2,2'-dipyridyl chloride. See, e.g., Wang et al., *Macromolecules*, 28: 7901-7910 (1995); Li et al., *Polym. Prepr.*, 40: 250 (1999); Rademacher et al., *Polym. Prepr.*, 40: 255 (1999); Huang et al., *Macromolecules*, 32: 1694-1696 (1999); which are incorporated by reference herein for any purpose.

FIG. 20 shows a general non-limiting exemplary approach for modifying the surface of polystyrene beads. One skilled in the art can select appropriate R, A, and B functionalities for conjugating a selected molecule or molecules to the bead. A non-limiting exemplary scheme is as follows. The surface of the bead is first modified to create surface thiol groups, e.g., by first making surface amino groups, and then converting to thiol groups according to methods known in the art. The surface thiol groups are then reacted, e.g., with an acryloxyl group (where A is $CH_2=CH-CO_2$) to form a Michael Addition adduct containing an aldehyde, carboxylic, or NHS-ester (i.e., B is —CHO, —$CO_2H$, or —$CO_2NHS$). In certain embodiments, that adduct is capable of being conjugated to a 3'- or 5' amino group of an oligonucleotide.

FIG. 21 shows non-limiting exemplary methods of surface modification of quantum dot particles and phosphor particles. The surface of the particle is reacted with either 1,4-dimercapto-2,3,-butanediol or 3-amino propyl thio hydrochloride. The resulting surface-functionalized particles have either free hydroxyl groups or free amino groups on their surfaces. The surface-functionalized particle may be reacted with (meth)acryloyl chloride. The resulting particles have polymerizable moieties on their surfaces.

DETAILED DESCRIPTION OF EXEMPLARY EMBODIMENTS

Figure 1:
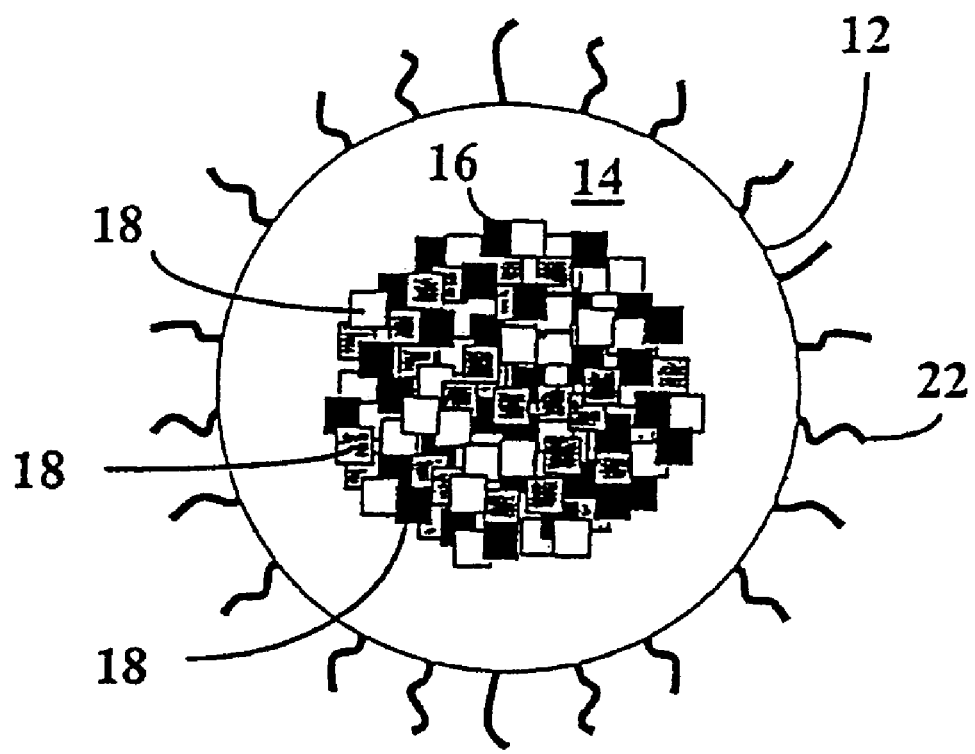
FIG. 1 illustrates certain embodiments of beads comprising phosphor particles wherein the phosphor particles are aggregated together.

It is to be understood that both the foregoing general description and the following detailed description are exemplary and explanatory only and are not restrictive of the invention, as claimed. In this application, the use of the singular includes the plural unless specifically stated otherwise. In this application, the use of "or" means "and/or"

unless specifically stated otherwise. Furthermore, the use of the term "including", as well as other forms, such as "includes" and "included," is not limiting. Also, terms such as "element" or "component" encompass both elements and components comprising one unit and elements and components comprising multiple subunits unless specifically stated otherwise. Also, the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

Definitions and Terms

A "bead" refers to any particle with which phosphor particles or other labels may be associated. Beads may be of any shape, including, but not limited to, spheres, rods, cubes, and bars. Beads may be any size. Beads may be made of any substrate, including, but not limited to, silica glass and organic polymers. Certain non-limiting examples of beads include those described, e.g., in U.S. Pat. Nos. 4,053,433; 4,499,052 (Fulwyler); U.S. Pat. No. 4,717,655 (Fulwyler); U.S. Pat. No. 3,957,741 (Rembaum, CalTech); U.S. Pat. No. 4,035,316 (Rembaum, CalTech); U.S. Pat. No. 4,105,598 (Rembaum, CalTech); U.S. Pat. No. 4,224,198 (Rembaum, CalTech); U.S. Pat. No. 4,326,008 (Rembaum, CalTech); U.S. Pat. No. 3,853,987 (Dreyer, CalTech); U.S. Pat. No. 4,108,972 (Dreyer, CalTech); U.S. Pat. No. 5,093,234 (Flow Cytometry Standards); U.S. Pat. No. 6,268,222 (Luminex); U.S. Pat. No. 5,326,692 (Molecular Probes); U.S. Pat. No. 5,573,909 (Molecular Probes); U.S. Pat. No. 5,723,218 (Molecular Probes); U.S. Pat. No. 5,786,219 (Molecular Probes); U.S. Pat. No. 5,028,545 (Soini); and U.S. Pat. No. 5,132,242 (Sau Cheung); as well as international application Publication Nos. WO 01/13119 (Luminex); WO 01/14589 (Luminex); WO 97/14028 (Luminex); WO 99/19515 (Luminex); WO 99/37814 (Luminex); WO 99/52708 (Luminex); WO 00/55363 (Amersham); WO 01/01141 (Amersham); WO 99/64867 (Amersham); and WO 94/11735 (Soini); which are incorporated by reference herein for any purpose.

As used herein, the term "polymer" includes a homopolymer and a copolymer. As used herein, a "homopolymer" is a polymer comprising one monomeric subunit. As used herein, a "copolymer" is a polymer comprising two or more different monomeric subunits. Thus, a polymeric chain comprising three different monomers (also known as a terpolymer) is included within the term "copolymer," as is a polymer chain comprising more than three different monomeric units. Exemplary polymers include, but are not limited to, cured epoxy resins; amine-containing polymers, including, but not limited to, poly(N-(3-aminopropyl) (meth)acrylamide); carboxylic acid-containing polymers, including, but not limited to, poly(acrylic acid )or poly(methacrylic acid) and their derivatives; poly((meth)acrylamide); poly(N-methyl (meth)acrylamide); poly(N,N-dimethyl (meth)acrylamide); poly(N-ethyl (meth)acrylamide); poly(N-propyl (meth)acrylamide); poly(N-iso-propyl (meth)acrylamide); poly(N-ethyl-N-methyl (meth)acrylamide); poly(N-hydroxymethyl (meth)acrylamide); poly(N-(2-hydroxyethyl) (meth)acrylamide); poly(N-(3-hydroxypropyl) (meth)acrylamide); poly(vinyl acetate); poly(vinyl alcohol); poly(N-vinyl formamide); poly(N-vinyl acetamide); poly(N-methyl-N-vinyl acetamide); poly(methyl (meth)acrylate); poly(ethyl (meth)acrylate); poly(propyl (meth)acrylate); poly(butyl (meth)acrylate); poly(vinyl pyrrolidone); poly(ethylene oxide); poly(vinyl methyl ether); poly(N-(meth)acrylylcinamide); poly(vinyl oxazolidone); poly(vinylmethyloxazolidone); poly(2-methyl-2-oxazoline); poly(2-ethyl-2-oxazoline); polystyrene and its derivatives; polymers of poly(ethylene glycol) (meth)acrylate; polymers of poly(ethylene glycol) methyl ether (meth)acrylate; polymers of poly(ethylene glycol) (meth)acrylate; polymers of poly(ethylene glycol) di(meth)acrylate; polymers of poly(ethylene glycol) diglycidyl ether; other suitable polymers capable of cross-linking; or their copolymers thereof.

The term "monomer" includes molecules that are capable of polymerizing to form straight-chain and/or branched polymers as well as molecules that are capable of polymerizing to form cross-linked polymers. The latter type of monomers are sometimes referred to as "cross-linking monomers."

In certain embodiments, beads are attached directly or indirectly to probes or other moieties. In certain embodiments, beads are indirectly attached to other molecules that are then attached to probes. In certain embodiments, beads may be attached to a probe prior to being added to a sample, or may become attached to a probe during the course of an incubation. In certain embodiments, beads may be attached directly to a probe, or through a linking molecule, such as a chemical linkage group, or affinity set, such as a streptavidin-biotin pair.

The terms "phosphor" and "phosphor particle," as used herein, refer to any inorganic phosphorescent particle. Exemplary phosphor particles include, but are not limited to, lanthanide phosphors, lanthanide chelates, yttrium chelates, yttrium oxysulfide activated with europium, europium chelates, erbium, sodium yttrium fluoride, vitroceramic phosphors, lanthanum fluoride, lanthanum oxysulfide, yttrium fluoride, yttrium gallate, yttrium aluminum garnet, gadolinium fluoride, barium yttrium fluoride, and gadolinium oxysulfide. Phosphor particles typically include an emitter. Exemplary emitters include, but are not limited to, erbium, holmium, terbium, thulium, europium, and other emitters. Certain non-limiting examples of phosphor particles have been discussed, for example, in U.S. Pat. No. 5,043,265 (Tanke et al.); U.S. Pat. No. 5,763,410 (Zarling et al.); U.S. Pat. No. 5,698,397 (Zarling et al.); U.S. Pat. Nos. 6,039,894; 6,399,397; and 6,159,686 (Kardos et al.); EP 0 660 936 B1 (Zarling et al.); EP 0 723 146 A1; and in Soini and Lovgren, CRC Crit. Rev. Anal. Chem. 18:105 (1987), which are incorporated by reference herein for any purpose. Certain exemplary luminescent materials, including but not limited to phosphors, are described, e.g., at the world wide web at mrw.interscience.wiley.com/ueic/articles/a15_519/frame-.html, which is incorporated by reference herein for any purpose.

In certain embodiments, phosphor particles comprise a coating. Exemplary coatings include, but are not limited to, surfactants, trialky phosphine oxide, polymers, passively adsorbed polymers, silica, glass, metals, polyethylene glycol (PEG), polypropylene glycol (PPO), diblock and triblock copolymers of PEO and PPO, etc. In certain embodiments, a coating comprises a hydrophilic polymer that is capable of reducing passive adsorption of certain molecules. In certain embodiments, the coating reduces passive adsorption of biomolecules. Exemplary coatings that can reduce passive adsorption include, but are not limited to, poly(ethylene oxide) methyl ether, polyacrylamide, poly(N-methyl-N-vinyl acetamide), poly(2-hydroxyethyl acrylate), and combinations thereof. One skilled in the art can select appropriate polymers for reducing passive adsorption.

In certain embodiments, phosphor particles may be modified to have reactive groups, members of affinity sets, or other molecules on their surfaces, with or without a coating. In certain embodiments, the reactive group on the surface is a polymerizable moiety such that a polymer/copolymer can be covalently grafted onto the phosphor particle.

The term "coded bead" refers to a bead encoded with a code specific to a particular bead and distinguishable from beads with other codes. If a bead is associated with a specific target or moiety, then the code of that bead is also associated with that particular target or moiety.

"Code" refers to the one or more labels which are specific to a particular bead. In certain embodiments, "code" refers to the one or more phosphor particles which are specific to a particular bead. In certain embodiments, "code" refers to the one or more phosphor particles and the one or more non-phosphor particle labels which are specific to a particular bead. In embodiments in which a code comprises more than one phosphor particle, the phosphor particles may be the same or different. In embodiments in which a code comprises more than one non-phosphor particle label, the one non-phosphor particle labels may be the same or different. Detection of a given code indicates the presence of a bead to which the code is specific. When codes are described as "detectably different," it means that they are distinguishable from one another by at least one detection method. Different codes include, but are not limited to, one or more labels that emit light of different wavelengths, one or more labels that emit light of different intensities, one or more labels that absorb light of different wavelengths, one or more labels that have different spectral signatures, one or more labels that have different radioactive decay properties, and one or more labels of different size. Different codes also include, but are not limited to, codes that emanate different numbers and/or patterns of signals.

The term "label" refers to any molecule or set of molecules that can provide a detectable signal. Labels include phosphor particles and non-phosphor particle labels. Exemplary non-phosphor particle labels include, but are not limited to, fluorescent molecules, fluorophores, organic dyes, chromogens, fluorescent dyes, metal-organic complexes, rare earth chelates, radioisotopes, enzymes, antigens including but not limited to epitope tags, affinity tags, binding proteins, luminescent molecules, phosphorescent groups, chemiluminescent groups, electrochemical detection moieties, quantum dots, and other nanoparticles, including, but not limited to, heavy metals, gold particles, resonance light scattering particles (see, e.g., Genicon Sciences, at the world wide web at invitrogen.com/content.cfm?pageid=9912, and references cited therein; Yguerabide, J. and Yguerabide, E. E; (1998) Anal. Biochem. 262:137-156;Yguerabide, J. and Yguerabide, E. E. (1998) Anal. Biochem. 262:157-176; and Bao, P. et al., (2002) Anal. Chem. 74:1792-1797; which are incorporated by reference herein for any purpose), and porous silicon smart dust (see, e.g., F. Cunin, T. A. Schmedake, J. R. Link, Y. Y. Li, J. Koh, S. N. Bhatia and M. J. Sailor (2002) *Nature Materials*, 1:39-41; J. R. Link, and M. J. Sailor (2003) *Proc. Nat Acad. Sci.*, 100:10607-10610; which are incorporated by reference herein for any purpose). In certain embodiments, a label can bind to another moiety or complex that produces a signal or that interacts with another moiety to produce a signal.

Labels include, but are not limited to, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751-56 (1997)). Labels also include, but are not limited to electro-chemiluminescence labels, including but not limited to, tris(bipyridal) ruthenium (II), also known as Ru(bpy)$_3^{2+}$, Os(1,10-phenanthroline)$_2$bis(diphenylphosphino)ethane$^{2+}$, also known as Os(phen)$_2$(dppene)$^{2+}$, luminol/hydrogen peroxide, Al(hydroxyquinoline-5-sulfonic acid), 9,1 0-diphenylanthracene-2-sulfonate, and tris(4-vinyl-4'-methyl-2,2'-bipyridal) ruthenium (II), also known as Ru(v-bpy$_3^{2+}$), and the like.

In certain embodiments, at least one reporter group comprises an electrochemiluminescent moiety that can, under appropriate conditions, emit detectable electrogenerated chemiluminescence (ECL). In ECL, excitation of the electrochemiluminescent moiety is electrochemically driven and the chemiluminescent emission can be optically detected. Certain exemplary electrochemiluminescent labels also include: Ru(bpy)$_3^{2+}$ and Ru(v-bpy)$_3^{2+}$ with emission wavelengths of 620 nm; Os(phen)$_2$(dppene)$^{2+}$ with an emission wavelength of 584 nm; luminol/hydrogen peroxide with an emission wavelength of 425 nm; Al(hydroxyquinoline-5-sulfonic acid) with an emission wavelength of 499 nm; and 9,10-diphenylanothracene-2-sulfonate with an emission wavelength of 428 nm; and the like. Certain other polyaromatic compounds and chelates of ruthenium, osmium, platinum, palladium, and other transition metals have shown electrochemiluminescent properties. Detailed descriptions of ECL and electrochemiluminescent moieties can be found, e.g., in A. Bard and L. Faulkner, Electrochemical Methods, John Wiley & Sons (2001); M. Collinson and M. Wightman, Anal. Chem. 65:2576 et seq. (1993); D. Brunce and M. Richter, Anal. Chem. 74:3157 et seq. (2002); A. Knight, Trends in Anal. Chem. 18:47 et seq. (1999); B. Muegge et al., Anal. Chem. 75:1102 et seq. (2003); H. Abrunda et al., J. Amer. Chem. Soc. 104:2641 et seq. (1982); K. Maness et al., J. Amer. Chem. Soc. 118:10609 et seq. (1996); M. Collinson and R. Wightman, Science 268:1883 et seq. (1995); and U.S. Pat. No. 6,479,233; all of which are incorporated by reference herein for any purpose.

Labels also include, but are not limited to, fluorescent molecules, including, but not limited to, fluoresceins, which include, but are not limited to, 6-carboxyfluorescein, 2',4',1,4,-tetrachlorofluorescein, and 2',4',5',7',1,4-hexachlorofluorescein (see, e.g., U.S. Pat. Nos. 5,188,934; 6,008,379; and 6,020,481; which are incorporated by reference herein for any purpose); rhodamines (see, e.g., U.S. Pat. Nos. 5,366,860; 5,847,162; 5,936,087; 6,051,719; and 6,191,278; which are incorporated by reference herein for any purpose); benzophenoxazines (see, e.g., U.S. Pat. No. 6,140,500; which is incorporated by reference herein for any purpose); energy-transfer fluorescent dyes, which comprise pairs of donors and acceptors (see, e.g., U.S. Pat. Nos. 5,863,727; 5,800,996; and 5,945,526; which are incorporated by reference herein for any purpose); and cyanines (see, e.g., WO 97/45539; which is incorporated by reference herein for any purpose); as well as any other fluorescent moiety capable of generating a detectable signal. Certain exemplary fluorescent dyes are described, e.g., in Haugland, R. P., *Handbook of Fluorescent Probes and Research Products*, Ninth Edition, which can be found at the worldwide web at probes.com/handbook/; Ullmann's Encyclopedia of industrial Chemistry, Copyright© 2002 by Wiley-VCH Verlag GmbH & Co. KGaA, DOI: 10.1002/14356007.a11_279, posted Jun. 15, 2000, which can be found at the worldwide web at mrw.interscience.wiley.com/ueic/articles/a11_279/frame-.html; and at the worldwide web at omlc.ogi.edu/spectra/PhotochemCAD/html/index.html; all of which are incorporated by reference herein for any purpose. Certain exemplary fluorescent dyes are also described, e.g., Lee, L. G. et al.

*Nucl. Acids Res.,* 20:2471-83 (1992); at the worldwide web at probes.com/lit/bioprobes38/6.pdf; and at the worldwide web at htrf-assays.com/techno/cryptates.htm; which are incorporated by reference herein for any purpose.

Other exemplary labels include, but are not limited to, luminescent molecules and molecules that can be involved in luminescent reactions, such as luciferin-luciferase reactions, as a non-limiting example. Certain exemplary luminescent molecules are described, e.g., in Demas et al., *Anal. Chem.,* 63: 829A-837A (1991), and at the worldwide web at mrw.interscience.wiley.com/ueic/articles/a15_519/frame-.html, which are incorporated by reference herein for any purpose. Labels also include, but are not limited to, chemiluminescent and electroluminescent molecules and reactions. In certain embodiments, chemiluminescent labels interact with a chemiluminescent substrate to produce a chemiluminescent signal. In certain embodiments, chemiluminescent labels bind to a molecule or complex that interacts with a chemiluminescent substrate to produce a chemiluminescent signal. As a non-limiting example, chemiluminescent labels may be exposed to film. Development of the film indicates whether or not the chemiluminescent labels are present in the sample and/or the quantity of the chemiluminescent labels in the sample.

Other exemplary labels include, but are not limited to, donor-acceptor interactions, in which a donor molecule emits energy that is detected by an acceptor molecule. The acceptor molecule then emits a detectable signal.

In certain embodiments, the term label refers to a molecule that interacts with a second molecule or other member of a set of molecules to provide a detectable signal. The signal may be provided by either the first molecule or the second molecule, e.g., FRET (Fluorescent Resonance Energy Transfer), or set of molecules. Labels include, but are not limited to, light-emitting or light-absorbing compounds which generate or quench a detectable fluorescent, chemiluminescent, or bioluminescent signal (see, e.g., Kricka, L. in *Nonisotopic DNA Probe Techniques* (1992), Academic Press, San Diego, pp. 3-28; Yeung et al., BioTechniques 36: 266-75 (2004); Dubertret et al., Nat. Biotech. 19: 365-70 (2001); Tyagi et al., Nat. Biotech. 18: 1191-96 (2000); which are incorporated by reference herein for any purpose).

Labels also include, but are not limited to, quantum dots. "Quantum dots" refer to semiconductor nanocrystalline compounds capable of emitting a second energy in response to exposure to a first energy. Typically, the energy emitted by a single quantum dot always has the same predictable wavelength. Exemplary semiconductor nanocrystalline compounds include, but are not limited to, crystals of CdSe, CdS, and ZnS. Suitable quantum dots according to certain embodiments are described, e.g., in U.S. Pat. Nos. 5,990, 479; 6,207,392 B1; 6,207,229; 6,251,303; 6,306,610; 6,319, 426; 6,322,901; 6,326,144; 6,426,513; 6,444,143; 6,576, 291; 6,607,829; in PCT Publication Nos. WO 01/71354, WO 02/47117, WO 00/17642, WO 00/17655, WO 00/17656, WO 01/07689, WO 99/26299, and WO 99/50916; and in "Quantum-dot-tagged microbeads for multiplexed optical coding of biomolecules," Han et al., Nature Biotechnology, 19:631-635 (2001); which are incorporated by reference herein for any purpose. Quantum dots are also described, e.g., at the worldwide web at evidenttech.com/index.php and at the worldwide web at qdots.com/live/index.asp, which are incorporated by reference herein for any purpose.

Labels of the present invention also include radioisotopes. Radioisotopes may be directly detected, or may excite a fluorophore that emits a wavelength of light that is then detected, e.g., using a scintillation counter. Other exemplary labels include, but are not limited to, molecules that are involved in infrared photon release.

Other examples of certain exemplary labels include particles with coded information, such as barcodes, and also include the microparticle tags described, e.g., in U.S. Pat. No. 4,053,433, which is incorporated by reference herein for any purpose. Certain other non-radioactive labeling methods, techniques, and reagents are reviewed in: *Non-Radioactive Labeling, A Practical Introduction,* Garman, A. J. (1997) Academic Press, San Diego; which is incorporated by reference herein for any purpose.

Exemplary labels also include, but are not limited to, reflecting, absorbing, and/or polarizing nanoparticles, and Raman scattering particles.

Finally, labels may be used according to any one of a large number of known techniques employing known labels, linkages, linking groups, affinity sets, reagents, reaction conditions, and analysis and purification methods. Labels include, but are not limited to, at least one element of multi-element indirect reporter systems, e.g., affinity tags such as biotin/avidin, antibody/antigen, ligand/receptor, including but not limited to binding proteins and their ligands, enzyme/substrate, and the like, in which one element interacts with other elements of the system in order to effect the potential for a detectable signal. Exemplary multielement reporter system include a probe comprising at least one biotin reporter group with an streptavidin-conjugated fluorophore, or vice versa; a probe comprising at least one dinitrophenyl (DNP) reporter group and a fluorophore-labeled anti-DNP antibody; and the like.

A "target" refers to any material that can be distinguished by a probe. Targets may include both naturally occurring and synthetic molecules.

The term "probe" or "target-specific probe" is any moiety that comprises a portion that can specifically bind a target. In certain embodiments, the probe may specifically bind one particular target. In certain embodiments, the probe may specifically bind a specific set of targets. For example, in certain embodiments, the probe may be degenerate such that it hybridizes to a particular set of sequences. In certain embodiments, a particular set of sequences may be antibody sequences. Exemplary probes may include, but are not limited to, nucleic acids, polypeptides, and other molecules that can specifically bind a target in a sample. Exemplary specific binding includes, but is not limited to, hybridization between nucleic acid molecules, antibody-antigen interactions, interactions between ligands and receptors, and interactions between aptamers and proteins.

The term "nucleotide base," as used herein, refers to a substituted or unsubstituted aromatic ring or rings. In certain embodiments, the aromatic ring or rings contain at least one nitrogen atom. In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, uracil, thymine, and analogs of the naturally occurring nucleotide bases, e.g., 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2 ms6iA), N2-dimethylguanine (dmG), 7-methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide," as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —$NR_2$ or halogen groups, where each R is independently H, $C_1$-$C_6$ alkyl or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352;, and WO 99/14226). Exemplary LNA sugar analogs within a polynucleotide include, but are not limited to, the structures:

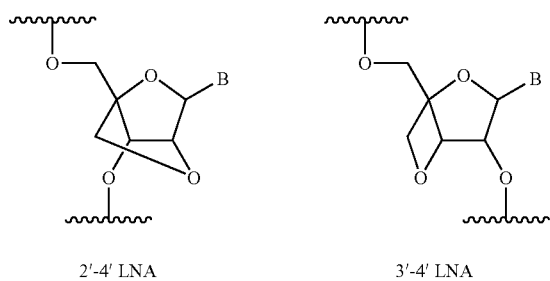

2'-4' LNA        3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T or U, the pentose sugar is attached to the $N^1$-position of the nucleotide base, except for pseudouridines, in which the pentose sugar is attached to the C5 position of the uracil nucleotide base (see, e.g., Kornberg and Baker, (1992) DNA Replication, $2^{nd}$ Ed., Freeman, San Francisco, Calif.).

One or more of the pentose carbons of a nucleotide may be substituted with a phosphate ester having the formula:

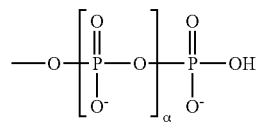

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and are sometimes denoted as "NTP," or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleotide chemistry, see: Shabarova, Z. and Bogdanov, A. *Advanced Organic Chemistry of Nucleic Acids*, VCH, New York, 1994.

The term "nucleotide analog," as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers which can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone.

As used herein, the terms "polynucleotide," "oligonucleotide," and "nucleic acid" are used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., H+, $NH_4^+$, trialkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-40 when they are sometimes referred to in the art as oligonucleotides, to several thousands of monomeric nucleotide units. Unless denoted otherwise, whenever a nucleic acid sequence is represented, it will be understood that the nucleotides are in 5' to 3' order from left to right and that "A"

denotes deoxyadenosine or an analog thereof, "C" denotes deoxycytidine or an analog thereof, "G" denotes deoxyguanosine or an analog thereof, and "T" denotes thymidine or an analog thereof, unless otherwise noted.

Nucleic acids include, but are not limited to, genomic DNA, cDNA, synthetic DNA, synthetic RNA, hnRNA, mRNA, rRNA, tRNA, fragmented nucleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deoxyribopolynucleotides according to the structural formulae below:

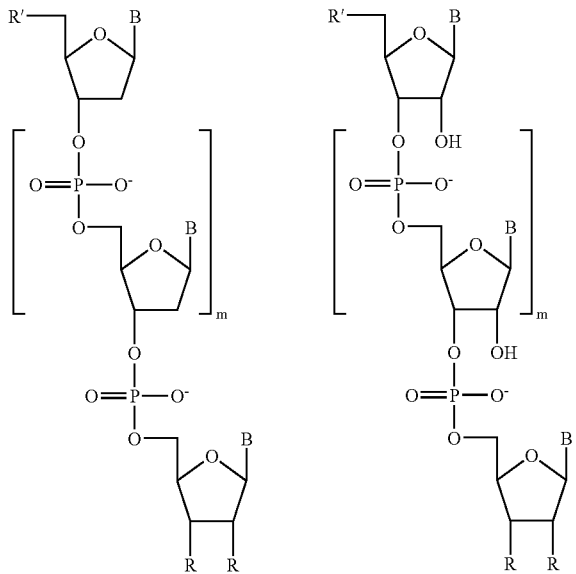

wherein each B is independently the base moiety of a nucleotide, e.g., a purine, a 7-deazapurine, a pyrimidine, or an analog nucleotide; each m defines the length of the respective nucleic acid and can range from zero to thousands, tens of thousands, or even more; each R is independently selected from the group comprising hydrogen, halogen, —R", —OR", and —NR"R", where each R" is independently (C1-C6) alkyl or (C5-C14) aryl, or two adjacent Rs are taken together to form a bond such that the ribose sugar is 2',3'-didehydroribose; and each R' is independently hydroxyl or

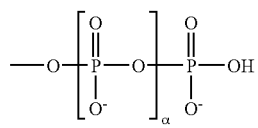

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid," "polynucleotide," and "oligonucleotide" may also include nucleic acid analogs, polynucleotide analogs, and oligonucleotide analogs. The terms "nucleic acid analog," "polynucleotide analog," and "oligonucleotide analog" are used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. No. 5,719,262; U.S. Pat. No. 5,698,685;); morpholinos (see, e.g., U.S. Pat. No. 5,698,685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate.

The terms "annealing" and "hybridization" are used interchangeably and mean the base-pairing interaction of one nucleic acid with another nucleic acid that results in formation of a duplex, triplex, or other higher-ordered structure. In certain embodiments, the primary interaction is base specific, e.g., A/T and G/C, by Watson/Crick and Hoogsteen-type hydrogen bonding. In certain embodiments, base-stacking and hydrophobic interactions may also contribute to duplex stability.

The term "variant" as used herein refers to any alteration of a protein, including, but not limited to, changes in amino acid sequence, substitutions of one or more amino acids, addition of one or more amino acids, deletion of one or more amino acids, and alterations to the amino acids themselves. In certain embodiments, the changes involve conservative amino acid substitutions. Conservative amino acid substitution may involve replacing one amino acid with another that has, e.g., similar hydorphobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. The hydropathic index is discussed, e.g., in Kyte etal., J. Mol. Biol., 157:105-131 (1982). It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or nonnatural, that may be incorporated, either enzymatically or synthetically, into a polypeptide or protein.

The term "separating moiety" refers to any moiety that, when associated with, attached to, or incorporated into a bead, may be used to separate the bead from at least one other component in a sample. Exemplary separating moieties include, but are not limited to, magnetic particles, paramagnetic particles, polynucleotides, antibodies, enzymes, proteins (including peptides), charged particles, and members of affinity sets, including, but not limited to, biotin and streptavidin.

The term "magnetic particle" refers to material which can be moved using a magnetic force. This includes, but is not limited to, particles that are magnetized; particles that are not magnetized but are influenced by magnetic fields (e.g., colloidal iron, iron oxides (e.g., ferrite and magnetite), nickel, and nickel-iron alloys); and particles which can become magnetized (e.g., ferrite, magnetite, iron, nickel, and alloys thereof).

A "probe set" is a group of two or more probes designed to detect at least one target. As a non-limiting example, a probe set may comprise two nucleic acid probes designed to hybridize to a target such that, when the two probes are hybridized to the target adjacent to one another, they are suitable for ligation together.

When used in the context of the present invention, "suitable for ligation" refers to at least one first target-specific probe and at least one second target-specific probe, each comprising an appropriately reactive group. In certain embodiments, "suitable for ligation" may refer to more than two target-specific probes. Exemplary reactive groups include, but are not limited to, a free hydroxyl group on the 3' end of the first probe and a free phosphate group on the 5' end of the second probe. In certain embodiments, the second probe may be a 5'-adenylated probe, in which the 5'-phosphate of adenosine is attached to the 5' end of the probe (a phosphoanhydride linkage). Exemplary pairs of reactive groups include, but are not limited to: phosphorothioate and tosylate or iodide; esters and hydrazide; RC(O)S$^-$, haloalkyl, or RCH$_2$S and α-haloacyl; thiophosphoryl and bromoacetoamido groups. Exemplary reactive groups include, but are not limited to, S-pivaloyloxymethyl-4-thiothymidine. In certain embodiments, first and second target-specific probes are hybridized to the target sequence such that the 3' end of the first target-specific probe and the 5' end of the second target-specific probe are immediately adjacent to allow ligation.

As used herein, an "affinity set" is a set of molecules that specifically bind to one another. Exemplary affinity sets include, but are not limited to, biotin and avidin, biotin and streptavidin, His$_6$ tag and nickel, receptor and ligand, antibody and ligand, antibody and antigen, a polynucleotide sequence and its complement, a polynucleotide and a protein that specifically binds that polynucleotide, and affinity binding chemicals available from Prolinx™ (Bothell, Wash.) as exemplified, e.g., by U.S. Pat. Nos. 5,831,046; 5,852,178; 5,859,210; 5,872,224; 5,877,297; 6,008,406; 6,013,783; 6,031,117; and 6,075,126. As used herein, a ligand is any molecule that may be specifically bound by a receptor. Ligands may be proteinaceous or non-proteinaceous. Exemplary ligands include, but are not limited to, proteins, polypeptides, polysaccharides, and small molecules. As used herein, an antigen is any molecule that may be specifically bound by an antibody. Antigens may be proteinaceous or non-proteinaceous. Exemplary antigens include, but are not limited to, proteins, polypeptides, polysaccharides, polynucleotides, and small molecules.

As used herein, the term "antibody" includes antibody fragments. Exemplary antibody fragments include, but are not limited to, Fab, Fab', F(ab')2, Fv, and single-chain antibodies.

In certain embodiments, affinity sets that are bound may be unbound. Methods of unbinding affinity sets include, but are not limited to, thermal denaturation, thermal dissociation, changing the pH, changing the salt concentration, changing the non-aqueous solvent concentration, and adding a competitive binding agent. For example, in certain embodiments, polynucleotide sequences that are hybridized may be thermally denatured. In certain embodiments, biotin bound to streptavidin may be heated and become unbound. In certain embodiments, a His$_6$ tag may be competitively unbound from nickel by the addition of imidazole.

Certain Exemplary Components

Targets

In certain embodiments, targets may include nucleic acid sequences. Exemplary target nucleic acid sequences include, but are not limited to, RNA and DNA. Exemplary RNA target sequences include, but are not limited to, mRNA, rRNA, tRNA, snRNA, viral RNA, synthetic RNA, and variants of RNA, such as splicing variants. Exemplary DNA target sequences include, but are not limited to, genomic DNA, plasmid DNA, synthetic DNA, phage DNA, nucleolar DNA, mitochondrial DNA, and chloroplast DNA.

In certain embodiments, target nucleic acid sequences include, but are not limited to, cDNA, yeast artificial chromosomes (YAC's), bacterial artificial chromosomes (BAC's), other extrachromosomal DNA, and nucleic acid analogs. Exemplary nucleic acid analogs include, but are not limited to, LNAs, PNAs, PPG's, and other nucleic acid analogs discussed herein.

A variety of methods are available for obtaining a target nucleic acid sequence for use with the beads, compositions, and methods of the present invention. When the nucleic acid target is obtained through isolation from a biological matrix, certain isolation techniques include, but are not limited to: (1) organic extraction followed by ethanol precipitation, e.g., using a phenol/chloroform organic reagent (see, e.g., Ausubel et al., eds., *Current Protocols in Molecular Biology* Volume 1, Chapter 2, Section I, John Wiley & Sons, New York (1993)), which may be accomplished using an automated DNA extractor, e.g., the Model 341 DNA Extractor available from PE Applied Biosystems (Foster City, Calif.); (2) stationary phase adsorption methods (see, e.g., Boom et al., U.S. Pat. No. 5,234,809; Walsh et al., *Biotechniques* 10(4): 506-513 (1991)); (3) salt-induced DNA precipitation methods (see, e.g., Miller et al., *Nucleic Acids Research*, 16(3): 9-10 (1988)), such precipitation methods being typically referred to as "salting-out" methods; and (4) cesium chloride banding (see, e.g., Sambrook et al., Molecular Cloning: a laboratory manual, 3$^{rd}$ Ed., Cold Spring Harbor Laboratory Press, Cold Spring Harbor, N.Y., 2001). In certain embodiments, the above isolation methods may be preceded by an enzyme digestion step to help eliminate unwanted protein from the sample, e.g., digestion with proteinase K, or other like proteases. See, e.g., U.S. patent application Ser. No. 09/724,613.

In certain embodiments, a target nucleic acid sequence may be derived from any living, or once living, organism, including but not limited to prokaryote, eukaryote, archaebacteria, plant, animal, and virus. In certain embodiments, the target nucleic acid sequence may originate from a nucleus of a cell, e.g., genomic DNA, snRNA, or unspliced RNA, or may be extranuclear nucleic acid, e.g., plasmid, mitochondrial nucleic acid, various RNAs, and the like. In certain embodiments, if the sequence from the organism is RNA, it may be reverse-transcribed into a cDNA target nucleic acid sequence. Furthermore, in certain embodiments, the target nucleic acid sequence may be present in a double-stranded or single stranded form.

Exemplary target nucleic acid sequences include, but are not limited to, amplification products, ligation products, transcription products, reverse transcription products, primer extension products, and cleavage products. In certain embodiments, target nucleic acid sequences may be produced by whole genome amplification. In certain embodiments, target nucleic acid sequences may be produced by isothermal amplification and/or ligation. In certain embodiments, target nucleic acid sequences may be produced by poymerase chain reaction (PCR) and/or ligation.

In certain embodiments, nucleic acids in a sample may be subjected to a cleavage procedure such as the cleavage procedure in an Invader™ assay (as exemplified, e.g., in U.S. Pat. Nos. 5,846,717; 5,985,557; 5,994,069; 6,001,567; and 6,090,543; which are incorporated by reference herein for any purpose). Such procedures produce a cleavage product when a nucleic acid of interest is present in a sample. In certain embodiments, the target may be such a cleavage product. Briefly, the cleavage procedure may employ two nucleic acid oligonucleotides that are designed to be complementary to the nucleic acid in the sample. A first oligonucleotide comprises a 5' portion that does not complement the nucleic acid in the sample, contiguous with a 3' portion that does complement the nucleic acid in the sample. A second oligonucleotide complements the nucleic acid in the sample in a region of the nucleic acid in the sample that is 3' of the region complemented by the first oligonucleotide, and includes a complementary or non-complementary portion that slightly overlaps with the region complemented by the first oligonucleotide. Hybridization of the two oligonucleotides to the nucleic acid in the sample causes a portion of the first oligonucleotide to be cleaved, often in the presence of an enzyme. The cleavage product is typically the 5' portion of the first oligonucleotide that does not complement the nucleic acid in the sample, and that portion of the complementary region that overlaps with the second oligonucleotide. This cleavage product comprises a known nucleic acid sequence. In certain embodiments, such cleavage products may be targets.

Different target nucleic acid sequences may be different portions of a single contiguous nucleic acid or may be on different nucleic acids. Different portions of a single contiguous nucleic acid may overlap.

The person of ordinary skill will appreciate that while a target nucleic acid sequence is typically described as a single-stranded molecule, the opposing strand of a double-stranded molecule comprises a complementary sequence that may also be used as a target sequence. Different target nucleic acid sequences may be at least partially complementary to one another.

Figure 8:
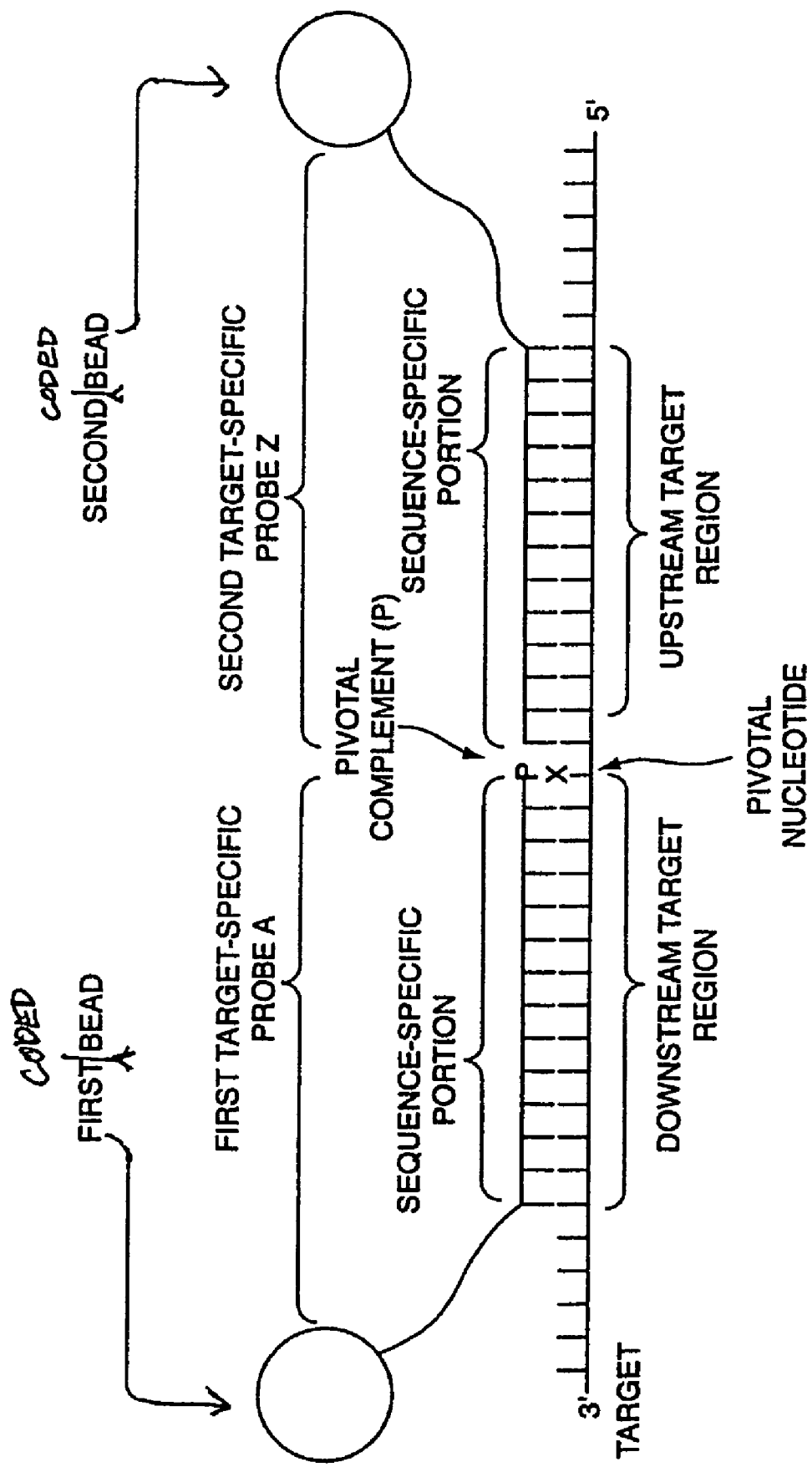
FIG. 8 illustrates a probe set comprising beads coded with phosphor particles according to certain embodiments.

In certain embodiments, a target nucleic acid sequence comprises an upstream or 5' region, a downstream or 3' region, and a "pivotal nucleotide" located in the upstream region or the downstream region (see, e.g., FIG. 8). In certain embodiments, the pivotal nucleotide may be the nucleotide being detected by the probe set and may represent, for example, without limitation, a single polymorphic nucleotide in a multiallelic target locus. In certain embodiments, more than one pivotal nucleotide is present. In certain embodiments, one or more pivotal nucleotides is located in the upstream region, and one or more pivotal nucleotides is located in the downstream region. In certain embodiments, more than one pivotal nucleotide is located in the upstream region and/or in the downstream region.

Other exemplary targets include, but are not limited to, polypeptide sequences. Polypeptide sequences include, but are not limited to, proteins, fragments of proteins, and other segments of amino acid sequences. Exemplary polypeptide target sequences include, but are not limited to, different polypeptide alleles (similar polypeptides with one or more different amino acids) and different polypeptide conformations (similar polypeptides with different secondary and/or tertiary structures).

Other exemplary naturally-occurring targets include, but are not limited to, hormones and other signal molecules, including, but not limited to, steroid-type molecules. Exemplary targets also include, but are not limited to, synthetic polypeptides, pharmaceuticals, and organic molecules.

Probes

In certain embodiments, a probe comprises a nucleic acid sequence-specific portion that is designed to hybridize in a sequence-specific manner with a complementary region on a target nucleic acid sequence. Exemplary nucleic acid probes include, but are not limited to, RNA and DNA. In certain embodiments, nucleic acid probes comprise nucleic acid analogs. Exemplary nucleic acid analogs include, but are not limited to, LNAs, PNAs, PPG's, and other nucleic acid analogs discussed herein. In certain embodiments, the sequence-specific portion of the probe may be specific for a particular sequence, or alternatively, may be degenerate, e.g., specific for a set of sequences.

Exemplary probes for target polypeptides include, but are not limited to, antibodies, ligands, and nucleic acid sequences that may be bound by the polypeptide.

In certain embodiments, probes comprise aptamers, which are nucleic acids that specifically bind to, e.g., certain polypeptide sequences or organic molecules. In certain embodiments, probes comprise polypeptides. Exemplary polypeptides include, but are not limited to, antibodies, receptor molecules, and enzymes. In certain embodiments, probes comprise antibodies directed to specific target polypeptide or non-polypeptide antigens.

In certain embodiments, a probe may include a member of an affinity set.

Polymers

It is to be understood that a polymer of the invention can comprise: (a) monomers of a single monomer subtype, e.g., a polymer having the form poly($M_1^1 M_2^0$) (or poly($M_1^1$)), that is, an $M_1$ homopolymer; (b) monomers selected from more than one subtype of $M_1$, e.g., a polymer having the form poly($M_1^2 M_2^0$) (or poly($M_1^2$)) is an $M_1$ copolymer containing monomers of a first subtype of $M_1$ and also monomers of a second subtype of $M_1$; and (c) monomers of one or more monomer subtypes of type $M_1$ and monomers of one or more monomer subtypes of type $M_2$, e.g., a polymer having the form poly($M_1^2 M_2^1$) contains two monomer subtypes of type $M_1$ and one monomer subtype of type $M_2$, that is, an $M_1/M_2$ copolymer. In certain embodiments, a monomer is a cross-linking monomer. Exemplary monomers include, but are not limited to, (meth)acrylamide, N,N-dimethyl (meth)acrylamide, vinyl acetate, styrene, N-vinylpyrrolidone, alkyl acrylates, N-butoxymethyl (meth)acrylamide, N-vinylamides, 4-vinylmorpholine vinyl methyl ketone, vinyl-methacrylate, vinyl norbornene, vinyl alkyl ethers, hydroxyethyl methacrylate, N,N'-methylenebisacrylamide, 2,2-bisacrylamido acetic acid, 2-(acryloyloxy) ethyl acid phosphate, ethylene glycol di(meth)acrylate, poly (ethylene glycol) di(meth)acrylate, and trimethylolpropane triacrylate.

Many methods of making polymers are known in the art and can be used to prepare polymers. Polymerization methods include, but are not limited to, suspension polymerization, dispersion polymerization, emulsion polymerization, inverse emulsion polymerization, microemulsion polymerization and membrane emulsification polymerization. Certain exemplary polymerization methods are summarized in C. A. Costello et al., *Copolymers in Kirk-Othmer Encyc. of Chem. Technol.* Vol. 7, 349-381 (4$^{th}$ ed. 1993).

In certain embodiments, beads are prepared using inverse emulsion polymerization (IEP). Exemplary IEP has been described, e.g., in "Inverse Emulsion (Microemulsion) Polymerization," Chapter 4 in *Radical Polymerization in Disperse Systems*, Barton et al., Ellis Horwood, New York, 1994, pp. 187-215; Candau et al., *J. Polym. Sci., Polym. Chem. Ed.*, 23:193-214 (1985); and Pross et al., *Polym. Int'l.*, 45:22-26 (1998), all of which are incorporated herein by reference for any purpose. IEP is sometimes referred to as inverse microsuspension polymerization or as inverse microemulsion polymerization. Polymerization in the inverse emulsion or microemulsion can be carried out by any manner known to those skilled in the art. Exemplary methods are described, e.g., in Griffin, *Emulsions in Kirk-Othmer Encyc. of Chem. Technol.* Vol. 8, 909-919 (3$^{rd}$ ed. 1979) and U.S. Pat. No. 5,530,069; and in the references cited therein, which are incorporated by reference herein for any purpose. In certain embodiments, e.g., when a phosphor particle is present, the polymerization reaction occurs in a discontinuous phase, which comprises at least one particle in the reaction solvent. Polymerization reactions involving a discontinuous phase may be carried out by any method, including, but not limited to, emulsion polymerization, inverse emulsion polymerization, and membrane emulsification polymerization.

Emulsion polymerization and inverse emulsion polymerization each comprise an aqueous phase and an oil phase. In certain embodiments, where the polymerization reaction contains particles, the aqueous phase and/or the oil phase may be discontinuous. In emulsion polymerization, the polymerization reaction occurs substantially in the oil phase. In inverse emulsion polymerization, the polymerization reaction occurs substantially in the aqueous phase. One skilled in the art can choose suitable components, which are soluble in the appropriate phase, for either emulsion polymerization or inverse emulsion polymerization. Thus, in certain embodiments, monomers and initiators that are soluble in the aqueous phase are typically chosen for inverse emulsion polymerization, and monomers and initiators that are soluble in the oil phase are typically chosen for emulsion polymerization. One skilled in the art can also choose a suitable surfactant, where appropriate. In certain embodiments, the polymerization reaction comprises at least one monomer and at least one initiator. In certain embodiments, the polymerization reaction further comprises a phosphor particle. In certain embodiments, the polymerization reaction further comprises a cross-linker.

Any suitable oil can be used to form an inverse emulsion. In certain embodiments, an oil is selected in which the monomer(s) to be polymerized are substantially insoluble. For the purpose of selecting an appropriate monomer/oil combination, "substantially oil insoluble" is defined as follows. At a temperature of 20° C., 1 ml of the selected monomer or monomer mixture is placed into 6 ml of the selected oil(s) and vortex mixed for 1 minute. After mixing, the liquid is allowed to stand for 10 minutes. The monomer(s) is substantially oil insoluble if phase separation, e.g., translucency, cloudiness and/or separate layers, can be observed with the unaided eye after the 10 minute period. Conversely, the monomer(s) is not substantially oil insoluble if no phase separation, i.e., a clear solution, is observed after the 10 minute period.

In certain embodiments, for emulsion polymerization, monomer(s) are chosen which are substantially insoluble in the aqueous phase. For the purpose of selecting an appropriate monomer, "substantially aqueous insoluble" is defined as follows. At a temperature of 20° C., 1 ml of the selected monomer or monomer mixture is placed into 6 ml of the selected aqueous solution and vortex mixed for 1 minute. After mixing, the liquid is allowed to stand for 10 minutes. The monomer(s) is substantially aqueous insoluble if phase separation, e.g., translucency, cloudiness and/or separate layers, can be observed with the unaided eye after the 10 minute period. Conversely, the monomer(s) is not substantially aqueous insoluble if no phase separation, i.e., a clear solution, is observed after the 10 minute period. Exemplary oils for use in emulsion and inverse emulsion polymerization include, but are not limited to, petroleum special (Fluka), aliphatic hydrocarbons (including, but not limited to, hexane, isooctane, decane, hexadecane, heptadecane, petroleum ethers, and mineral oils) aromatic hydrocarbons (including, but not limited to, benzene, toluene, cumene, alkylbenzenes and alkylarylbenzenes), fluorinated hydrocarbons (including, but not limited to, Fluorinert™ FC-37 (3M) and perfluoropolyethers, including, but not limited to Fomblin™ (Ausimont, Italy) and Demnum™ (Daikin Industries, Japan)), and other halogenated hydrocarbons. One skilled in the art can select a suitable oil for emulsion polymerization, inverse emulsion polymerization, or membrane emulsification polymerization. In certain embodiments, the choice of oil depends on the monomers selected. In certain embodiments, the choice of oil depends on the particles to be incorporated into the bead. In certain embodiments, the choice of oil depends on the desired bead size. In certain embodiments, the choice of oil depends on other additives included in the reaction mixture.

A wide variety of polymerization initiators may be used in polymerization methods of various embodiments of the invention. In certain embodiments, the polymerization is initiated by at least one free-radical, anionic and/or cationic initiator.

Exemplary free-radical initiators include, but are not limited to, azo compounds, which include, but are not limited to, 2,2'-azobisisobutyronitrile (AIBN), 4,4'-azobis (4-cyanopentanoic acid), and 2,2'-azobis (N,N'-dimethyleneisobutyramidine) dihydrochloride; peroxides, e.g., benzoyl peroxide; ; alkyl peresters, for example, bis(2-ethylhexyl) peroxydicarbonate and TRIGONOX ADC-NS60 (Akzo Chemie America); alkyl hydroperoxides, e.g., 1-butyl hydroperoxide; persulfates, e.g., ammonium persulfate and potassium persulfate; hydropersulfates; inorganic peroxides; redox initiating systems, including, but not limited to, the peroxy-redox types and, e.g., $K_2S_2O_8/Na_2S_2O_5$, ferrous ammonium sulfate, and ammonium persulfate; carbon-carbon initiators, e.g., hexasubstituted ethanes; and photoinitiators, such as Michler's ketone, i.e., 4,4'-bis-(dimethylamino)benzophenone, and IRGACURE-1700 and DAROCURE-1173 from Ciba-Geigy. See, e.g., Sanchez et al., *Initiators (Free-Radical) in Kirk-Othmer Encyc. of Chem. Technol.* Vol. 14, 431-460 (4$^{th}$ ed. 1993); which are incorporated by reference herein for any purpose.

Exemplary anionic initiators include, but are not limited to, aromatic radical anions, e.g., sodium naphthalene; alkyl lithium compounds, e.g., t-butyl lithium; fluorenyl carbanions; 1,1-diphenylmethylcarbanions; and cumyl potassium. Certain anionic initiators are described, e.g., in Quirk et al., Initiators (Anionic) in *Kirk-Othmer Encyc. of Chem. Technol.* Vol. 14, 461-476 (4$^{th}$ ed. 1993), which is incorporated by reference herein for any purpose.

Exemplary cationic initiators include, but are not limited to, protic acids, cation donor (initiator)/Friedel-Crafts acid (coinitiator) systems, and stable cation salts. Certain cationic initiators are described, e.g., in Faust, *Initiators (Cationic) in Kirk-Othmer Encyc. of Chem. Technol.* Vol. 14, 476-482 (4$^{th}$ ed. 1995), which is incorporated by reference herein for any purpose. In certain embodiments, the free-radical, anionic, and/or cationic initiator undergoes thermal or photolytic decomposition.

In certain embodiments, methods of initiating polymerization include, but are not limited to, exposing the monomer(s) to an electron beam, ultraviolet radiation, and/or a high energy ionizing radiation source, such as γ-radiation from a $^{60}$Co or $^{137}$Cs source, α-particles, β-particles, fast neutrons, and/or x-rays. See, e.g., Sanchez et al., *Initiators (Free-Radical)* at 454-457; Sheppard et al., *Initiators in Kirk-Othmer Encyc. of Chem. Technol.* Vol. 13, 367-370 (3$^{rd}$ ed. 1981); which are incorporated by reference herein for any purpose.

In certain embodiments, at least one surfactant is used to form an inverse emulsion. It is conventional to characterize a surfactant by its hydrophilic lipophilic balance (HLB), a measure of the relative simultaneous attraction of the surfactant for water or oil. On the HLB scale ranging from 1 to 40, relatively lipophilic surfactants have a low numerical value, while relatively hydrophilic surfactants have a high numerical value.

Many surfactants are described, e.g., in *McCutcheon's Emulsifiers & Detergents*, North American Ed., Manufacturing Confectioner Pub. Co., Glen Rock, N.J., 1988, pp. 1-217, which is incorporated by reference herein for any purpose. A surfactant may be nonionic, anionic, cationic, or both anionic and cationic, e.g., an amphoteric surfactant. In certain embodiments, charged groups on a surfactant are associated with at least one counterion. See, e.g., Lynn, Jr. et al., *Surfactants in Kirk-Othmer Encyc. of Chem. Technol.* Vol. 23, 483-541 (4$^{th}$ ed. 1997), which is incorporated herein by reference for any purpose.

Exemplary nonionic surfactants include, but are not limited to, polyoxyethylene surfactants, e.g., alcohol ethoxylates and alkylphenol ethoxylates; carboxylic acid esters, e.g., glycerol esters and polyoxyethylene esters; anhydrosorbitol esters, e.g., mono-, di- and tri-esters of sorbitan and fatty acids; polyalkylene oxide block copolymers; and poly(oxyethylene-co-oxypropylene) nonionic surfactants.

Exemplary anionic surfactants include, but are not limited to, carboxylates, e.g., soaps, polyalkoxycarboxylates and N-acylsarcosinates; sulfonates, e.g., alkylbenzene sulfonates, naphthalene sulfonates and petroleum sulfonates; sulfates, e.g., alcohol sulfates and ethoxylated and sulfated alcohols; and phosphates, e.g., phosphate esters.

Exemplary cationic surfactants include, but are not limited to, amines, e.g., aliphatic mono-, di- and polyamines derived from fatty and rosin acids; and quaternary ammonium salts, e.g., dialkyldimethyl and alkyltrimethyl ammonium salts, alkylbenzyldimethyl ammonium chlorides, and alkylpyridinium halides.

Certain amphoteric surfactants are known in the art. Exemplary amphoteric surfactants include, but are not limited to, alkylbetaines, amidopropylbetaines, and imidazolinium derivatives.

Certain considerations that may be taken into account in certain instances for selecting a suitable surfactant or surfactant blend to form an inverse emulsion are summarized, e.g., in Griffin, *Emulsions in Kirk-Othmer Encyc. of Chem. Technol.* Vol. 8, 909-919 (3$^{rd}$ ed. 1979), which is incorporated herein by reference for any purpose. Furthermore, in certain embodiments, certain monomers, e.g., acrylamide, may sometimes act as a co-surfactant.

In certain embodiments, a sufficient amount of the surfactant or surfactant blend is used such that a stable emulsion, inverse emulsion, or microemulsion is formed. It is within the skill in the art to determine which surfactant to choose and what such a sufficient amount of the surfactant is for the selected emulsion.

In certain embodiments, the oil and/or water phase of the emulsion may contain other additives, if desired. Exemplary additives include, but are not limited to, chain transfer agents, pH adjusters, co-initiators, sensitizers, charge-transfer complexes or donor-acceptor complexes (e.g., when photoinitiation is used), chelating agents, e.g., EDTA (e.g., to remove polymerization inhibitors), etc.

In certain embodiments, reactive moieties are included as an additive in the polymerization reaction. Reactive moieties may be a portion of a larger molecule that is included as an additive in the polymerization reaction. Exemplary reactive moieties include, but are not limited to, hydroxyl groups and derivatives thereof; amino groups and derivatives thereof; carboxylic acid groups and derivatives thereof; epoxy groups; alkene groups; allyl groups; 2-bromo-2-methylpropionyl groups; 2,2,6,6-tetramethylpiperidinyloxy (TEMPO) groups; N-hydroxysuccinimide groups and esters and other derivatives thereof; and molecules containing a combination of reactive groups. In certain embodiments, when reactive moieties are included in the polymerization reaction, the resulting polymer beads will comprise some of the reactive moieties on their surfaces such that the reactive moiety may be used to further modify the bead.

In certain embodiments, a member of an affinity set is included as an additive in the polymerization reaction. In certain embodiments, the resulting polymer beads will have some of the member of the affinity set on their surfaces such that they are available for binding to the other member of the affinity set.

In certain embodiments, the reactive moiety or member of an affinity set added to the polymerization reaction further comprises a polymerizable moiety, such that the reactive moiety or member of an affinity set is covalently incorporated into the bead during the polymerization reaction. In certain embodiments, the reactive moiety or member of an affinity set comprises a hydrophilic moiety and a hydrophobic moiety, such that it prefers the oil/water interface during the polymerization reaction. In certain embodiments, when the reactive moiety or member of an affinity set prefers the oil/water interface, it is preferably incorporated during the polymerization reaction to the region comprising the bead surface.

Certain Exemplary Embodiments

Beads

In certain embodiments, a bead is provided. In certain embodiments, a bead comprises a substrate and two or more different phosphor particles, wherein each of the two or more different phosphor particles is capable of producing a different detectable signal.

Exemplary beads may be made of any of a number of substrates, including, but not limited to, silica, glass, metal, organic polymers, polystyrene, acrylic, acrylic polymers, polyacrylamide, latex, polysaccharide, and polypropylene. In certain embodiments, beads are uncoated. In certain embodiments, beads are fully or partially coated. Exemplary substances used to coat beads include, but are not limited to, polymers, silica, glass, metals, polyethylene glycol (PEG), etc.

In certain embodiments, beads comprise at least one-phosphor particle. In certain embodiments, beads further comprise at least one label other than a phosphor particle. Exemplary non-phosphor particle labels include, but are not limited to, fluorescent molecules, dyes, radioisotopes, luminescent molecules, quantum dots, and other nanoparticles, including, but not limited to, gold particles, resonance light scattering particles, and porous silicon smart dust.

In certain embodiments, a bead has a diameter of between about 0.05 µm and about 20 µm. In certain embodiments, a bead has a diameter of between about 0.1 µm and about 10 µm. In certain embodiments, a bead has a diameter of between about 1 µm and about 6 µm. In certain embodiments, a bead has a diameter of between about 3 µm and about 5 µm. In certain embodiments, a bead has a diameter of about 2 µm, about 3 µm, about 4 µm, about 5 µm, or about 6 µm.

In certain embodiments, a label is incorporated into a microbead prior to attachment to, or incorporation into, a bead. Exemplary labels that may be incorporated into microbeads include, but are not limited to, fluorescent molecules, dyes, radioisotopes, luminescent molecules, quantum dots, and other nanoparticles, including, but not limited to, gold particles, resonance light scattering particles, and porous silicon smart dust. In certain embodiments, at least one phosphor particle is incorporated into a microbead prior to attachment to, or incorporation into, a bead. In certain embodiments, each microbead comprises one phosphor particle. in certain embodiments, each microbead comprises more than one phosphor particle.

In certain embodiments, at least one dye is incorporated into a microbead prior to attachment to, or incorporation into, a bead. In certain embodiments, microbeads comprising dyes are referred to as "dye dots." In certain embodiments, a hydrophobic dye is incorporated into a hydrophilic microbead. In certain embodiments, a microbead comprises one or more molecules of a label. In certain embodiments, each microbead comprises one or more molecules of the same label. For example, a particular dye may be encapsulated into a microbead and then one or more of the microbeads may be attached to, or incorporated into, a bead. In certain embodiments, two or more different microbeads, each containing a different dye, are attached to, or incorporated into, a bead. In certain embodiments, encapsulating each type of dye into separate microbeads prior to incorporation into beads may reduce quenching between the different dyes.

In certain embodiments, a microbead comprises a substrate and at least one label. Microbeads may be made of any substrate, including, but not limited to, silica glass and organic polymers. Microbeads comprising dyes may be made by any method, including, but not limited to, absorption of the dyes into microbeads that have been swollen in an aqueous or organic solution; and incorporation of the dyes into microbeads during polymerization, e.g., by inverse emulsion polymerization, emulsion polymerization, or membrane emulsion polymerization. Exemplary methods of making microbeads include, but are not limited to, the methods shown in FIGS. 11 through 14.

Figure 11:
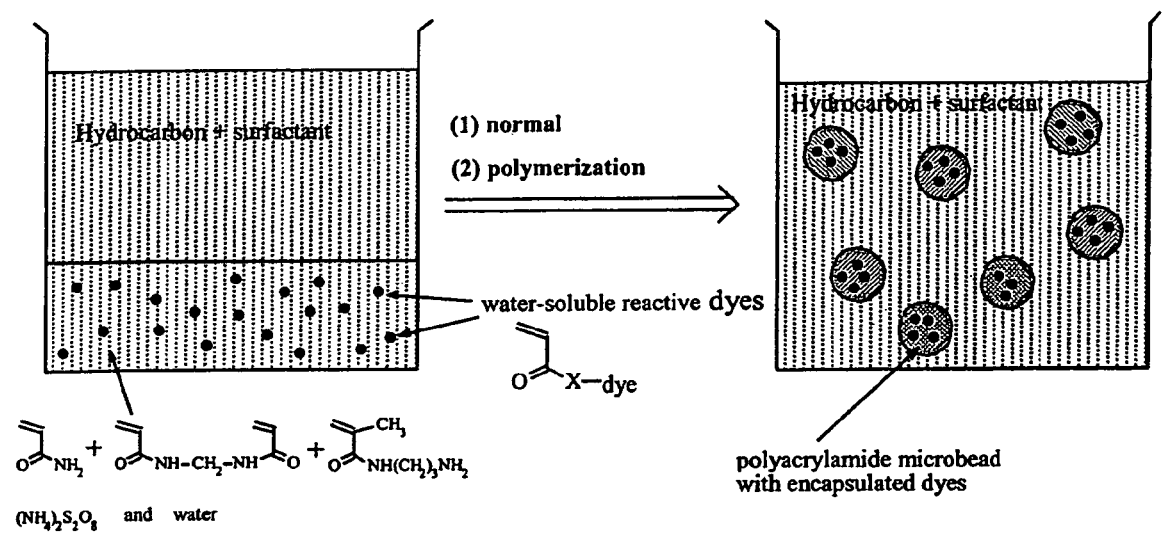
FIG. 11 shows a non-limiting exemplary method of making polyacrylamide microbeads using reactive dyes and inverse emulsion polymerization. The reaction is carried using acrylamide, bis-acrylamide, amine-functionalized methacrylamide, and water-soluble reactive dyes in the aqueous phase.

FIG. 11 shows a nonlimiting exemplary method of making microbeads encapsulating dyes using inverse emulsion polymerization. The reaction is carried out using acrylamide, bis-acrylamide, amine-functionalized methacrylamide, and water soluble aqueous dyes in the aqueous phase. In certain embodiments, the amine-functionalized methacrylamide is replaced with acrylic acid sodium salt. In certain embodiments, the emulsion further comprises a surfactant. The polymerization is initiated, e.g., by the addition of ammonium persulfate. In certain embodiments, the water soluble aqueous dyes comprise polymerizable moieties so that they may be covalently incorporated into the polymer during polymerization.

Figure 12:
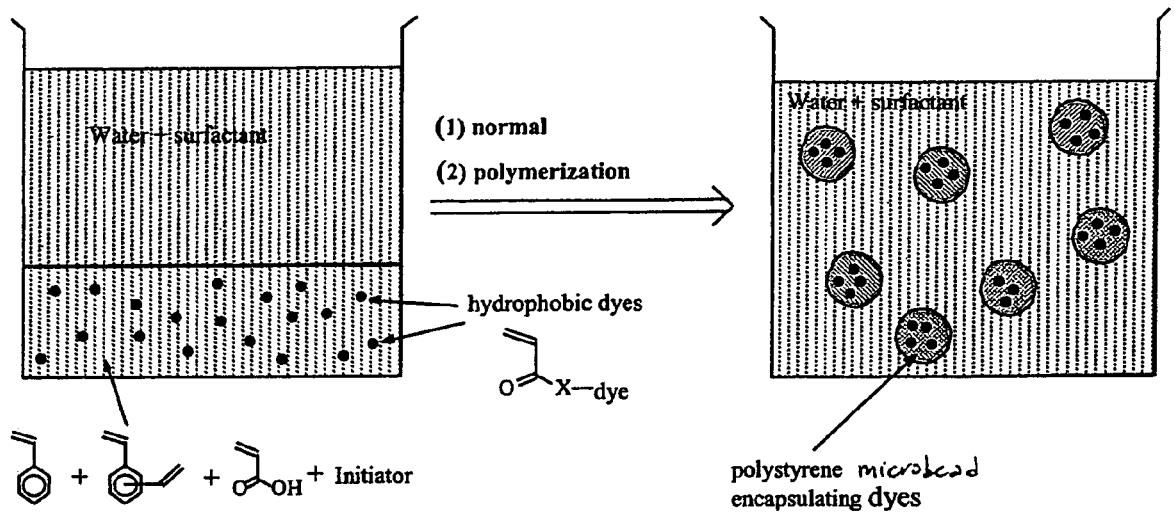
FIG. 12 shows a non-limiting exemplary method of making polystyrene microbeads using reactive dyes and emulsion polymerization. The reaction is carried out using styrene, divinyl styrene, acrylic acid, and hydrophobic reactive dyes in the oil phase.

FIG. 12 shows a nonlimiting exemplary method of making microbeads encapsulating dyes using emulsion polymerization. The reaction is carried out using styrene, divinyl styrene, acrylic acid, and oil soluble aqueous dyes in the oil phase. In certain embodiments, the acrylic acid is replaced with a protected vinylaniline. In certain embodiments, the emulsion further comprises a surfactant. The polymerization is initiated, e.g., by the addition of at least one initiator. Exemplary initiators include, but are not limited to, thermal initiators (e.g., 2,2'-azobisisobutyronitrile (AIBN)); organic peroxides, including, but not limited to, hydroperoxides (e.g., cumyl hydroperoxide), dialkyl peroxides (e.g., t-butyl cumyl peroxide and dicumyl peroxide), diacyl peroxides (e.g., benzoyl peroxide and decanoyl peroxide), ketone peroxides (e.g., 2,4-pentanedione peroxide), peroxydicarbonates (e.g., di(n-propyl peroxydicarbonate)), peroxylesters (e.g., t-amyl perbenzoate and t-butyl peroxypicalate), and peroxyketals (e.g., 1,1-di(t-butylperozy)cyclohexane). In certain embodiments, the oil soluble aqueous dyes comprise polymerizable moieties so that they may be covalently incorporated into the polymer during polymerization.

Figure 13:
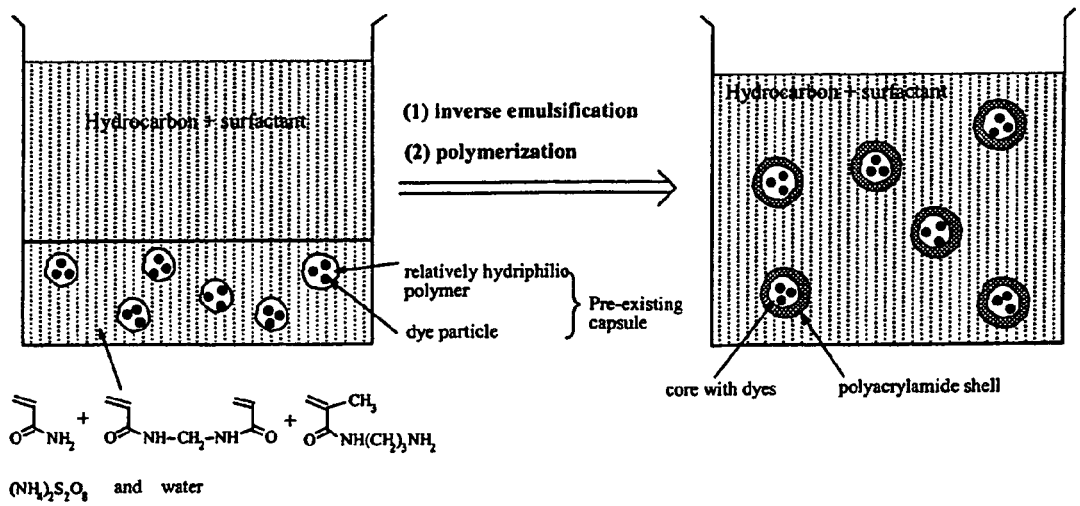
FIG. 13 shows a non-limiting exemplary method of core/shell microencapsulation of hydrophilic microbeads comprising dyes using inverse emulsion polymerization. The reaction is carried out using acrylamide, bis-acrylamide, amine-functionalized methacrylamide, and hydrophilic microbeads comprising dyes in the aqueous phase.

FIG. 13 shows a nonlimiting exemplary method of core/shell microencapsulation of hydrophilic microbead comprising dyes using inverse emulsion polymerization. The reaction is carried out using acrylamide, bis-acrylamide, amine-functionalized methacrylamide, and hydrophilic microbeads comprising dyes in the aqueous phase. In certain embodiments, the amine-functionalized methacrylamide is replaced with acrylic acid sodium salt. In certain embodiments, the emulsion further comprises a surfactant. The polymerization is initiated, e.g., by the addition of ammonium persulfate. In certain embodiments, core-shell microencapsulation of microbeads may be carried out using hydrophobic microbeads and emulsion polymerization substantially as shown, e.g., in FIG. 12.

Figure 14:
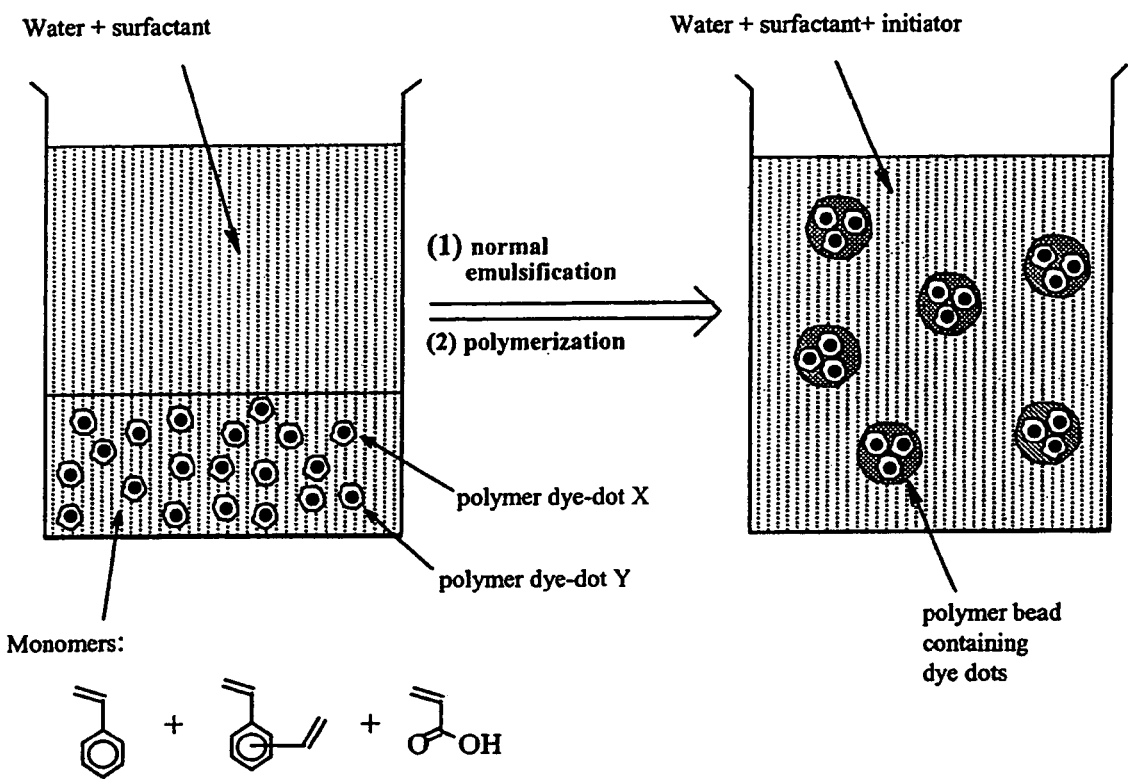
FIG. 14 shows a non-limiting exemplary method of encapsulating microbeads comprising dyes (also referred to as "dye-dots") into beads using emulsion polymerization. The reaction is carried out using styrene, divinyl styrene, acrylic acid, and microbeads comprising dyes in the oil phase.

FIG. 14 shows an exemplary method of incorporating microbeads comprising dyes (also referred to as "dye dots") into beads. The reaction is carried out using styrene, divinyl styrene, acrylic acid, and oil soluble aqueous dyes in the oil phase. In certain embodiments, the acrylic acid is replaced with a protected vinylaniline. In certain embodiments, the emulsion further comprises a surfactant. The polymerization is initiated, e.g., by the addition of at least one initiator. Exemplary initiators include, but are not limited to, persulfates (e.g., ammonium persulfate and potassium persulfate) and water-soluble azo compounds (e.g., 2,2'-azibis(N,N'-dimethyleneisobutyramidine)dihydrochloride, 2,2'-azobis(2-amidinopropane)dihydrochloride, and 4,4'-azobis(4-cyanopentanoic acid). In certain embodiments, a coinitiator or catalyst is used. Exemplary coinitiators and catalysts include, but are not limited to, tetramethylethylenediamine (TEMED). In certain embodiments, microbeads comprising dyes (sometimes referred to as "dye dots") are encapsulated into relatively hydrophilic beads using inverse emulsion polymerization. Hydrophilic beads may be made using inverse emulsion polymerization, e.g., substantially as shown in FIG. 11.

In certain embodiments, a microbead has a diameter of between about 1 nm and 5000 nm. In certain embodiments, a microbead has a diameter of between about 5 nm and about 500 nm. In certain embodiments, a microbead has a diameter of between about 10 nm and about 300 nm. In certain embodiments, a microbead has a diameter of about 10 nm, about 20 nm, about 30 nm, about 40 nm, about 50 nm, about 75 nm, about 100 nm, about 150 nm, about 200 nm, about 300 nm, or about 500 nm.

In certain embodiments, microbeads comprise the same substrate as the bead they are attached to or incorporated into. In certain embodiments, microbeads comprise at least one different substrate as the bead they are attached to or incorporated into. In certain embodiments, a dye dot comprises at least one dye encapsulated in an organic polymer, an inorganic polymer, or an inorganic-organic hybrid polymer.

In certain embodiments, a separating moiety is used to separate the bead and anything attached to the bead from a surrounding sample. In certain embodiments, a separating moiety is not associated with a bead in the absence of target. In certain embodiments, a separating moiety becomes associated with a bead in the presence of a target. In certain embodiments, a bead comprises a separating moiety. Exemplary separating moieties include, but are not limited to, magnetic materials, paramagnetic materials, polynucleotides, antibodies, and other members of affinity sets, including, but not limited to, biotin and streptavidin.

In certain embodiments, separating moieties are separated in view of their mobility. In certain embodiments, separating in view of mobility is accomplished by the size of the separating moiety. In certain embodiments, electrophoresis is used to separate separating moieties. In certain embodiments, mobility modifiers may be employed during electrophoresis. Non-limiting exemplary mobility modifiers and methods of their use have been described, e.g., in U.S. Pat. Nos. 5,470,705; 5,580,732; 5,624,800; and 5,989,871; which are incorporated by reference herein for any purpose. In certain embodiments, by changing the mobility of a bead, one may distinguish signals associated with the presence of a target from signals not associated with the presence of a target.

In certain embodiments, separating moieties are separated according to a property other than their mobility. As a non-limiting example, a separating moiety may comprise a magnetic particle. In certain embodiments, where a separating moiety comprises a magnetic particle, the separating moiety may be separated from other components of a mixture using a magnet. As a non-limiting example, a separating moiety may comprise biotin. In certain embodiments, where a separating moiety comprises biotin, the separating moiety may be separated from other components of a mixture using, e.g., streptavidin.

In certain embodiments, beads comprise at least one probe. In certain embodiments, beads comprise one or more probes on their surfaces. In certain embodiments, a probe is used to bind a target. Exemplary probes include, but are not limited to, polynucleotides, polypeptides, antibodies, receptor molecules, aptamers, enzymes, and members of affinity sets.

One of skill in the art will appreciate that there are many methods of obtaining beads comprising probes and/or separating moieties. Exemplary methods include, but are not limited to, attaching the probes or separating moieties to the beads using covalent chemical bonding, UV crosslinking, non-covalent interaction, and linking through an affinity set. As a non-limiting example, streptavidin molecules may be covalently attached to carboxylic acid groups on a bead surface. Oligonucleotide probes may be biotinylated, then linked to the beads via the streptavidin molecules.

In certain embodiments, a coded bead may comprise a first probe that binds to a first region of polynucleotide target and a separating moiety may comprise a second probe that binds to a second region of a polynucleotide target that is adjacent to the first region. In certain embodiments, where the first probe and the second probe are polynucleotides, the first probe and the second probe, once boind to the polynucleotide target, may be ligated together. In certain embodiments, the separating moiety is then separated from the other components of the composition. In certain embodiments, where ligation has occurred, the separating moiety is attached to the coded bead, which may be detected following separation. In certain embodiments, where ligation has not occurred, the separating moiety is not attached to the coded bead, so no bead is detected following separation. See, e.g., U.S. Publication No. 2003/0165935 A1, which is incorporated by reference herein for any purpose. In certain embodiments, the separating moiety comprises a magnetic particle. In certain embodiments, the separating moiety comprises biotin.

Certain Exemplary Forms of Beads and Certain Exemplary Methods of Making Beads

In certain embodiments, as a non-limiting example, phosphor particles may be incorporated into cross-linked polymer beads. In certain embodiments, polystyrene beads may be synthesized using an emulsion of styrene (98% vol./vol.), divinylbenzene (1% vol./vol.), and acrylic acid (1% vol./vol.) at 70° C. In certain embodiments, the beads are then swelled in a solvent mixture containing 5% (vol./vol.) chloroform and 95% (vol./vol.) propanol or butanol. In certain embodiments, a controlled amount of phosphor particles are added to the mixture. In certain embodiments, after incubation at room temperature, the embedding process is complete. In certain embodiments, the size of the beads may be controlled by the amount of a stabilizer (e.g., polyvinylpyrrolidone and partially hydrolyzed polyvinyl alcohol) used in the synthesis.

In certain embodiments, the method of making beads discussed above results in beads with varying numbers of phosphor particles. Also, in certain embodiments, if one uses more than one color of phosphor particle, one may obtain beads that have varying numbers of the different colors. In certain embodiments, after such bead preparation, the resulting beads are sorted by the relative number of phosphor particles of each color in a given bead to obtain groups of identically coded beads with distinct codes. In certain embodiments, the sorting can be automated using machines, such as a Fluorescence Activated Cell Sorter (FACS) or other flow-cytometer type detection method that can distinguish between different codes.

Several methods of making beads with phosphor particles are available, resulting in the placement of the phosphor particles at different areas within or on the bead.

For example, FIG. 1 shows certain embodiments in which a bead (12) contains an aggregate (16) of different colored phosphor particles (18) encapsulated within a substrate (14). FIG. 1 also shows certain embodiments in which probes and/or separating moieties (22) are attached to the outside of the bead. Probes and/or separating moieties may be attached directly to the outside of the bead, or attached through a linking molecule, such as a chemical linkage group or affinity set. Chemical linkage groups include, but are not limited to, polymer tethers. Exemplary polymer tethers include, but are not limited to, poly(ethylene oxide), and polyacrylamide. A non-limiting exemplary method of making the bead shown in FIG. 1 is to mix together different phosphor particles (18) and allow them to form aggregates (16). In certain embodiments, after the phosphor particles form aggregates (16), the aggregates are sorted by size and then encapsulated with the substrate (14). In certain embodiments, the phosphor aggregates are encapsulated during a polymerization reaction, e.g., using emulsion polymerization or inverse emulsion polymerization. In certain embodiments, the polymerization reaction comprises an oil phase, an aqueous phase, at least one monomer, and at least one phosphor aggregate. In certain embodiments, the polymerization reaction comprises at least two monomers, one of which is a cross-linking monomer. In certain embodiments, the polymerization reaction further comprises an initiator. In certain embodiments, the polymerization reaction further comprises a surfactant.

Figure 2:
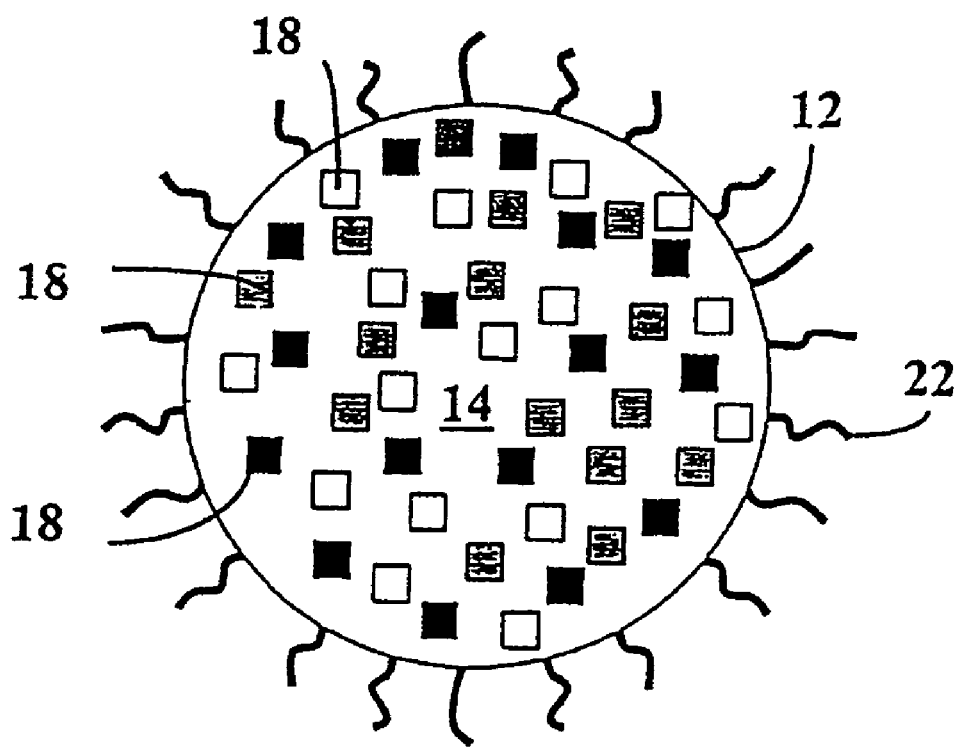
FIG. 2 illustrates certain embodiments of beads comprising phosphor particles wherein the phosphor particles are homogeneously distributed throughout the substrate of the bead.

In certain embodiments, beads are formed without phosphor particle aggregates. In certain embodiment, phosphor particles are incorporated into the bead. For example, FIG. 2 shows certain embodiments in which a bead (12) has phosphor particles (18) homogeneously distributed throughout the substrate (14). FIG. 2 also shows certain embodiments in which probes and/or separating moieties (22) are attached to the outside of the bead (12). In certain embodiments, phosphor particles are surface-modified prior to incorporation into a bead. In certain embodiments, surface modification reduces aggregation of the phosphor particles. In certain embodiments, surface modification reduces passive adsorption of biomolecules, including, but not limited to, polynucleotides and polypeptides.

A non-limiting exemplary method of making beads as shown in FIG. 2 is to mix different phosphor particles (18) into a molten substrate (14) until the phosphor particles (18) are homogeneously distributed. The molten substrate with the distribution of phosphor particles is then formed into beads. Methods of making beads from molten substrate are well known in the art.

In certain embodiments, the phosphor particles are incorporated into polymer beads during the polymerization reaction, e.g., using emulsion polymerization or inverse emulsion polymerization. In certain embodiments, the polymerization reaction comprises an oil phase, an aqueous phase, at least one monomer, and at least one phosphor particle. In certain embodiments, the polymerization reaction comprises at least two monomers, one of which is a cross-linking monomer. In certain embodiments, the polymerization reaction further comprises an initiator. In certain embodiments, the polymerization reaction further comprises a surfactant. In certain embodiments, following polymerization, the phosphor particles are incorporated into the bead. In certain embodiments, following polymerization, the phosphor particles are distributed throughout the polymer substrate. In certain embodiments, following polymerization, the phosphor particles are homogeneously distributed throughout the polymer substrate.

Figure 3:
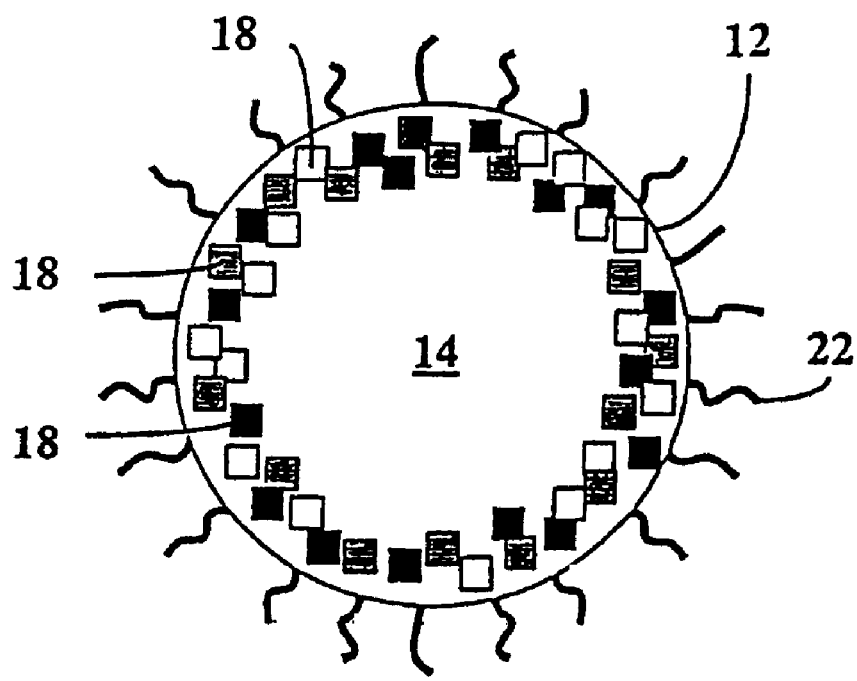
FIG. 3 illustrates certain embodiments of beads comprising phosphor particles wherein the phosphor particles are embedded near the surface of the bead.

In certain embodiments, beads have phosphor particles embedded near the surface of the bead. For example, FIG. 3 shows certain embodiments in which a bead (12) has different phosphor particles (18) embedded near the surface of the bead. FIG. 3 also shows certain embodiments in which probes and/or separating moieties (22) are attached to the outside of the bead (12).

A non-limiting exemplary method of making a bead shown in FIG. 3 is to mix different phosphor particles into a liquid. The liquid is then used to coat a substrate (14). The substrate (14) is then heated such that part of the substrate melts and phosphor particles (18) on the outside of the substrate become embedded within the substrate (14), which is then cooled.

In certain embodiments, the bead shown in FIG. 3 can be made by soaking phosphor particles into a bead that has been swelled. Certain methods of soaking particles into swelled beads are known in the art. In certain embodiments, the bead is swelled in organic solvent. In certain embodiments, the soaking reaction is carried out for a length of time sufficient to soak the phosphor particles only part way into the bead, such that the phosphor particles are generally localized to the region just below the surface of the bead.

In certain embodiments, beads are manufactured with a solid core. In certain embodiments, the solid core is a magnetic or paramagnetic particle. The solid core may or may not be transparent, and, in certain embodiments, may be made of metal. In certain embodiments, the portion of the bead containing the phosphor particles is made of the same polymer composition as the solid core. In certain embodiments, a bead having a solid core is made by emulsion polymerization or inverse emulsion polymerization. In certain embodiments, the polymerization reaction comprises phosphor particles, solid core particles, and at least one type of monomer. In certain embodiments, the polymerization reaction further comprises a cross-linking monomer.

In certain embodiments, the resulting beads having one solid core are separated from those beads that do not have a solid core or have more than one solid core. In certain embodiments, that separation is done by size. In certain embodiments, where a magnetic solid core is used, the beads having at least one solid core are separated from those without a solid core by their magnetic characteristics. In certain embodiments, a solid core is used which contains a dye, so that beads having the solid core may be separated by detecting the dye, e.g., using FACS.

Figure 4:
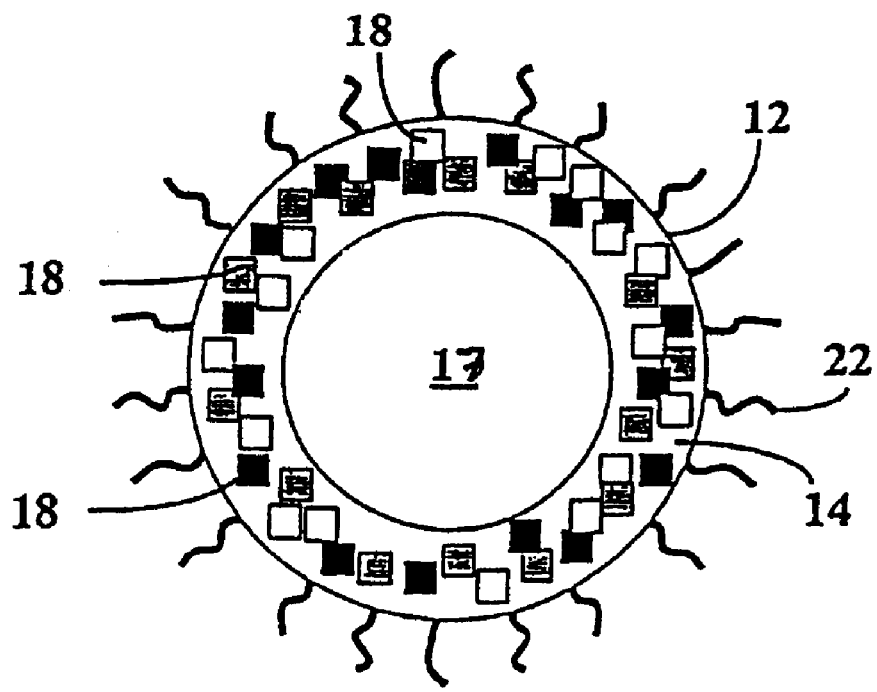
FIG. 4 illustrates certain embodiments of beads comprising phosphor particles wherein the bead further comprises a solid core.

FIG. 4 shows certain embodiments in which a bead (12) has different phosphor particles (18) and a solid core (17). FIG. 4 also shows certain embodiments in which probes and/or separating moieties (22) are attached to the outside of the bead (12).

A non-limiting exemplary method of making a bead as shown in FIG. 4 is to mix different phosphor particles (18) with a molten substrate (14) until the phosphor particles (18) are homogeneously distributed within the substrate (14). The molten substrate with the distribution of different phosphor particles is then used-to coat the solid core (17) and allowed to cool.

In certain embodiments, beads as shown in FIG. 4 may be made by including the solid core and phosphor particles in a polymerization reaction, as discussed above.

Figure 5:
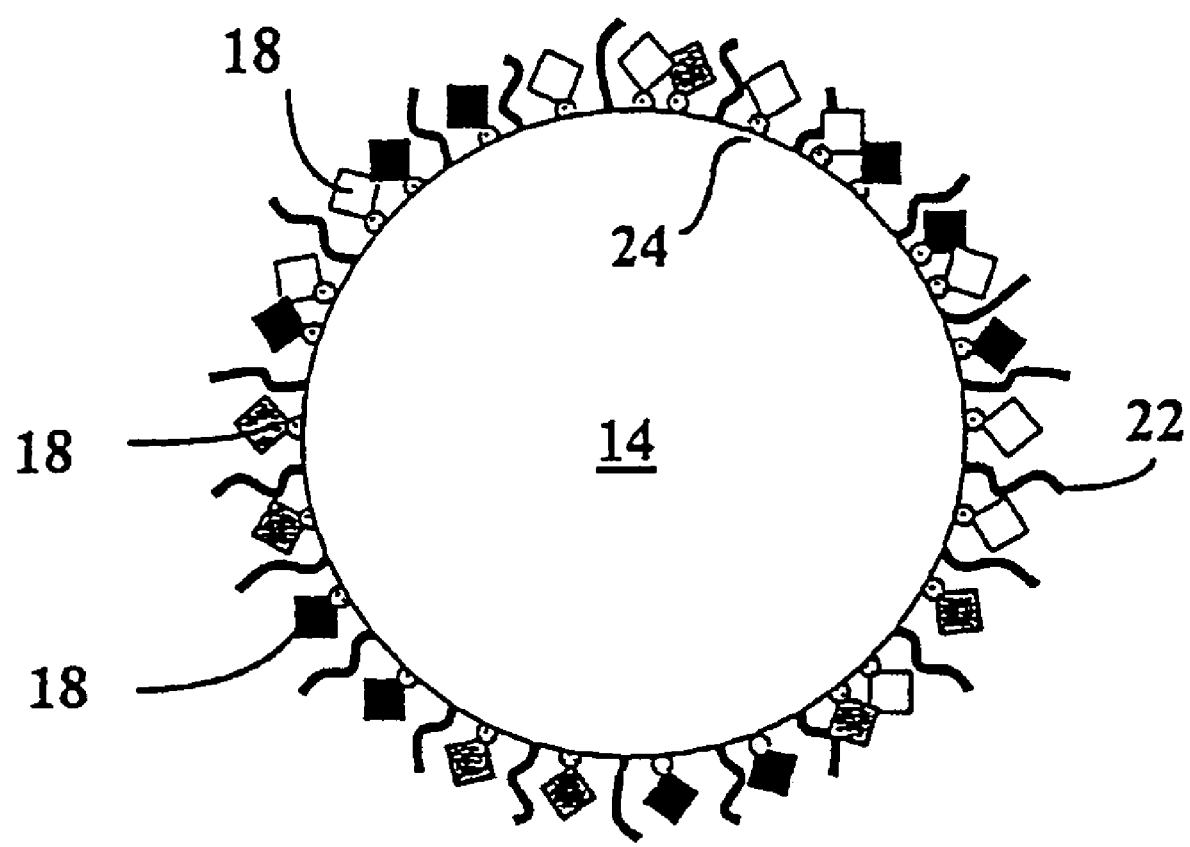
FIG. 5 illustrates certain embodiments of beads comprising phosphor particles wherein the phosphor particles are attached to the surface of the bead.

In certain embodiments, different phosphor particles may be attached to the surface of a bead. For example, FIG. 5 shows certain embodiments in which a bead has different phosphor particles (18) attached to the surface of a substrate (14). In certain embodiments, the different phosphor particles (18) are attached to the substrate (14) by a covalent chemical linkage or affinity set (24). FIG. 5 also shows certain embodiments in which probes and/or separating moieties (22) are attached to the outside of the bead (12).

An non-limiting exemplary method of making a bead as shown in FIG. 5 is by coating a substrate (14) with a member of an affinity set, such as streptavidin. Exemplary streptavidin-coated beads are well known in the art and are commercially available. Different phosphor particles (18) may then be coated with another member of the same affinity set. For example, in certain embodiments, if the substrate is coated with streptavidin, the different phosphor particles may be coated with biotin, which would then allow the different phosphor particles to bind to the substrate.

In certain embodiments, different phosphor particles may be covalently attached to polymer beads that have reactive moieties on their surfaces. Such polymer beads can be made, in certain embodiments, by including an additive having a reactive moiety in the polymerization reaction. Phosphor particles having an appropriate functionality on their surfaces can then be covalently coupled to the reactive moieties on the surface of the beads.

In certain embodiments, an additive comprises a member of an affinity set. In certain embodiments, an additive comprises a polymerizable moiety and a member of an affinity set. In certain embodiments, phosphor particles having the other member of the affinity set can then be bound to the surface of the bead.

Exemplary Phosphor Particles

In certain embodiments, a bead comprising at least one phosphor particle is provided. In certain embodiments, a bead comprising at least two different phosphor particles is provided. In certain embodiments, a bead comprising three or more different phosphor particles is provided. In certain embodiments, a bead may comprise multiple copies of each different phosphor particle. Thus, in certain embodiments, a bead comprising "two or more different phosphor particles" may comprise one or more copies of each different phosphor particle. Exemplary phosphor particles include, but are not limited to, lanthanide phosphors, lanthanide chelates, yttrium chelates, yttrium oxysulfide activated with europium, europium chelates, erbium, sodium yttrium fluoride, vitroceramic phosphors, lanthanum fluoride, lanthanum oxysulfide, yttrium fluoride, yttrium gallate, yttrium aluminum garnet, gadolinium fluoride, barium yttrium fluoride, and gadolinium oxysulfide. In certain embodiments, phosphor particles comprise at least one of the following exemplary emitters: erbium, holmium, terbium, thulium, europium, and any other emitters. Exemplary phosphor particles have been discussed, for example, in U.S. Pat. No. 5,043,265 (Tanke et al.); U.S. Pat. No. 5,763,410 (Zarling et al.); U.S. Pat. No. 5,698,397 (Zarling et al.); and U.S. Pat. No. 6,159,686 (Kardos et al.); EP 0 660 936 B1 (Zarling et al.); EP 0 723 146 A1; and in Soini and Lovgren, *CRC Crit. Rev. Anal. Chem.* 18:105 (1987).

In certain embodiments, phosphor particles absorb light at one or more wavelengths, and emit a single specific wavelength of light. Phosphor particles that have absorbed light may be said to be "excited." An excited phosphor particle may then emit a signal in the form of a specific wavelength of light. When the wavelength of light emitted by a phosphor particle is of a higher frequency (shorter wavelength) than the frequency of the signal that excited the phosphor particle, the phosphor particle may be referred to as an "up-converting" phosphor particle. When a phosphor particle emits a signal of a lower frequency (longer wavelength) than the frequency of the signal used to excite the phosphor particle, the phosphor particle is referred to as a "down-converting" phosphor particle. In certain embodiments, beads comprise "up-converting" phosphor particles. In certain embodiments, beads comprise "down-converting" phosphor particles. In certain embodiments, beads comprise both "up-converting" phosphor particles and "down-converting" phosphor particles.

Many distinct phosphor colors are known that emit light in the visible spectrum. In certain embodiments, varying the number of-phosphor particles in a bead may provide coding by the intensity of the signal. In certain embodiments, varying the colors of light emitted by the phosphor particles may provide coding by the color of the signal. In certain embodiments, phosphor particles that emit light of different wavelengths may be excited by light of the same wavelength, such that a single light source may excite several different phosphor particles.

In certain embodiments, the wavelength of light emitted by a phosphor particle may be different in length from the wavelength used to excite the phosphor particle. Thus, in certain embodiments, the background "noise" in detecting the signals emitted by phosphor particles may be reduced by using phosphor particles that emit wavelengths that are distinct from the wavelength used to excite the phosphor particles. In certain embodiments, phosphor particles may be excited by infrared wavelengths as long as 980 nm and emit light in the visible spectrum.

Further, in certain embodiments, the band of the light emitted by a phosphor particle may be narrow, allowing easy distinction of different detected wavelengths of light emitted by phosphor particles. In certain embodiments, the band of light emitted by a phosphor particle is less than 30 nm. In certain embodiments, the band of light emitted by a phosphor particle is less than 20 nm. In certain embodiments, the band of light emitted by a phosphor particle is less than 10 nm. In certain embodiments, the band of light emitted by a phosphor particle is less than 5 nm.

The manufacture of many phosphor particles is well known in the art, and many phosphor particles are available commercially.

Exemplary Surface Modification of Particles

In certain embodiments, the surface of particles are modified. In certain embodiments, the surface of particles are modified prior to incorporating them into beads. In certain embodiments, the surface of particles are modified prior to attaching them to beads. In certain embodiments, the surface of quantum dots are modified. In certain embodiments, the surface of phosphors are modified.

Non-limiting exemplary methods of modifying the surface of quantum dots are described, e.g., in U.S. Pat. Nos. 6,251,303; 6,319,426; 6,306,610; 6,426,513; 6,444,143; and 6,326,144; which are incorporated by reference herein for any purpose.

Non-limiting exemplary methods of modifying the surface of phosphors are described, e.g., in U.S. Pat. Nos. 6,537,829; 5,674,698; and 5,698,397; and PCT Publication No. WO 02/04527; which are incorporated by reference herein for any purpose.

Non-limiting exemplary methods of modifying the surface of quantum dot particles and phosphor particles are shown, e.g., in FIG. 21. FIG. 21 shows non-limiting exemplary methods of surface modification of particles. In certain embodiments, the surface of the particle is first reacted with either 1,4-dimercapto-2,3,-butanediol or 3-amino propyl thio hydrochloride. The resulting surface-functionalized particles have either free hydroxyl groups or free amino groups on their surfaces. In certain embodiments, the surface-functionalized particle are then reacted with (meth)acryloyl chloride. In certain embodiments, the resulting particles have polymerizable moieties on their surfaces.

In certain embodiments, surface modification of particles makes the particles more hydrophobic. In certain embodiments, surface modification of particles makes them more hydrophilic. In certain embodiments, hydrophobic surface modification is chosen in order to encapsulate the particles into hydrophobic beads, such as polystyrene. In certain embodiments, hydrophilic surface modification is chosen in order to encapsulate the particles into hydrophilic beads, such as polyacrylamide. One skilled in the art can choose the appropriate surface modification according to the application.

In certain embodiments, surface modification of particles results in the presence of polymerizable moieties on the surface of the particles. Non-limiting exemplary polymerizable moieties include, but are not limited to, acrylamide and (meth)acrylate groups (see, e.g., FIG. 21). In certain embodiments, particles having polymerizable moieties on their surface are incorporated into beads such that the polymerizable moieties become covalently incorporated into the polymer bead. One of skill in the art can select appropriate polymerizable moieties for the type of polymer bead selected.

Exemplary Coded Beads

Figure 6:
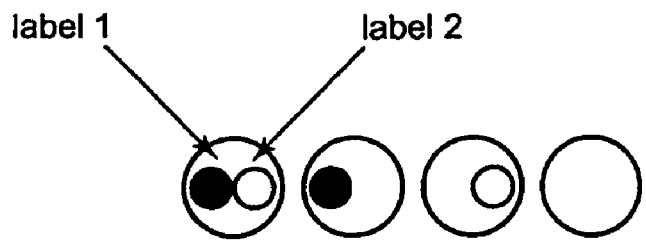
FIG. 6 illustrates certain potential binary and ternary codes using two or three different labels according to certain embodiments.
Figure 6:
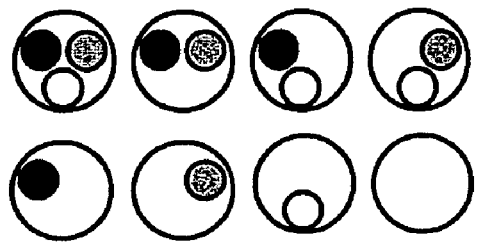
Figure 6:
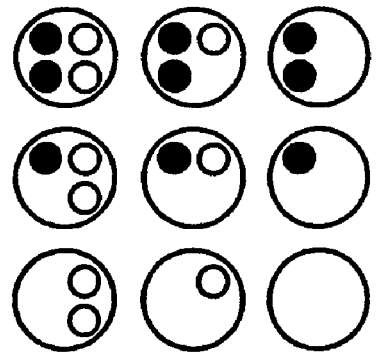

According to certain embodiments, multiple targets may be detected in a sample, and distinguished by using different codes in at least two different beads. In certain embodiments, the beads are coded using two or more phosphor particles. In certain embodiments, one uses multiple wavelengths or colors of phosphor particles, which multiplies the number of potential different codes. For example, if a given phosphor particle is given a binary code, then one can detect the presence or absence of a specific phosphor particle (either a "1" or "0"—hence a binary code). If only one color is used, then there are 2 codes, one with the phosphor particle, and one without the phosphor particle. If two colors are used (e.g., red and blue), then 4 codes are possible—(1) red, (2) blue, (3) red and blue, and (4) no color (see, e.g., FIG. 6). Each additional color multiplies the number of possible codes by two. Thus, if 10 colors of phosphor particles are used, then $2^{10}$, or 1,024, binary codes are possible.

In certain embodiments, one may use two or more sets of labels that emit light in overlapping spectra, but that are excited by a different wavelengths of light. For example, in certain embodiments, two different labels may emit light of substantially the same wavelength, but one is excited by infrared light and the other is excited by ultraviolet light. In certain embodiments, two different sets of labels may emit light in the spectra of 400 to 700 nm, but one set is excited by infrared light and the other set is excited by ultraviolet light. Thus, the emissions of the two different sets may be distinguished by exciting them with the different wavelengths of light at different times.

For example, assume that a first set of labels emits ten colors A, B, C, D, E, F, G, H, I, and J and is excited by infrared light. The number of possible codes for that first set of labels is $2^{10}$, or 1024, codes. Further, assume that a second set of labels emits the same ten colors A, B, C, D, E, F, G, H, I, and J, but is excited by ultraviolet light. The number of possible codes for that second set of labels is also $2^{10}$, or 1024, codes. If both the first set of labels and the second set of labels are employed, however, the number of possible codes for the combined sets of labels is 1024 multiplied by 1024, or 1,048,576 possible codes.

Exemplary labels that may be employed in sets that are excited by different wavelengths of light include, but are not limited to, quantum dot particles, down-converting phosphor particles (excited by ultraviolet light), up-converting phosphor particles (excited by infrared light), and dyes (excited by ultraviolet light, infrared light, or visible light). Various embodiments enable various combinations of particles and/or dyes with various combinations of excitation wavelengths of light to provide a large number of unique codes.

Figure 10:
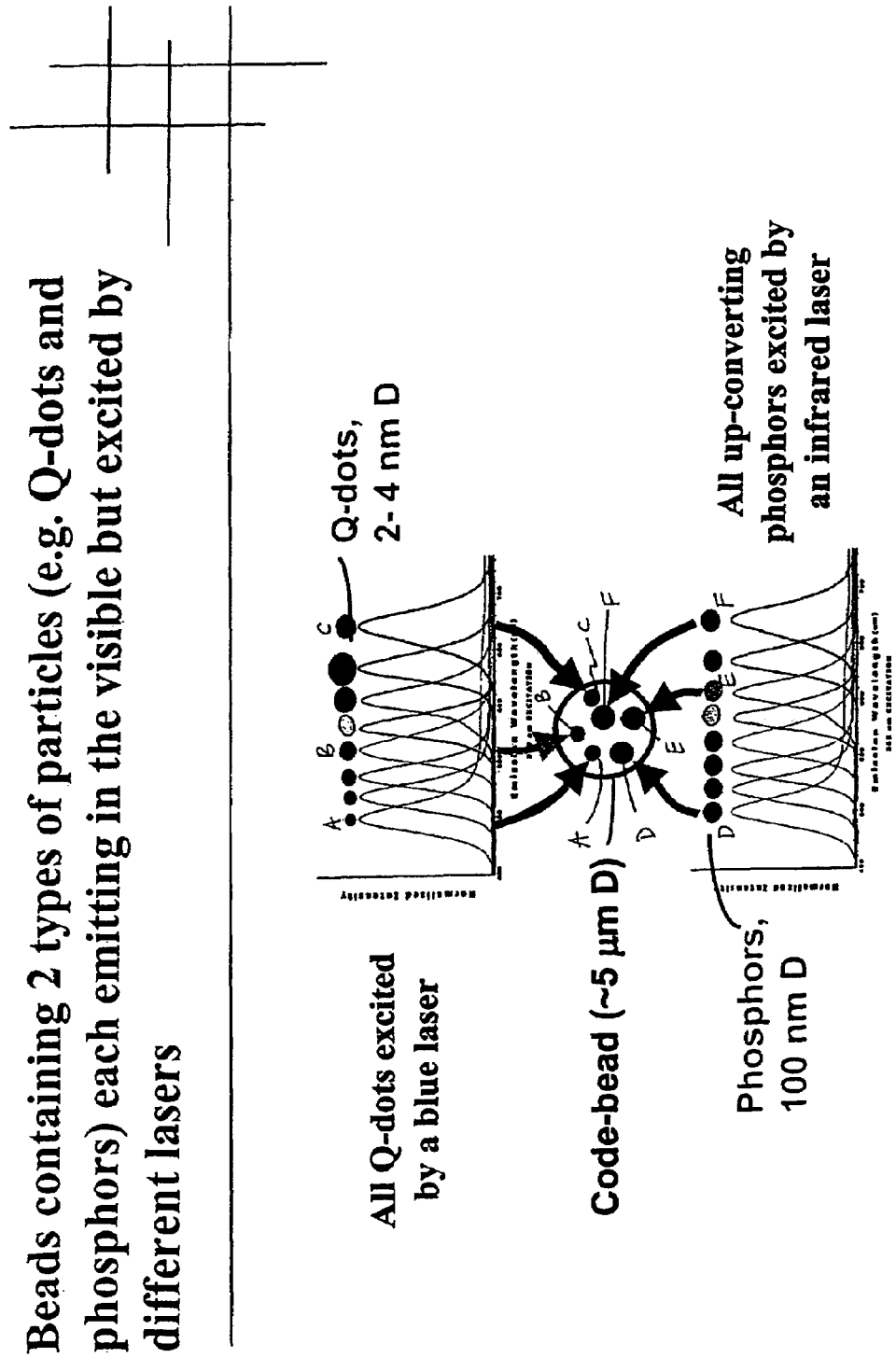
FIG. 10 shows an exemplary bead containing 2 types of particles (e.g., quantum dot particles and phosphor particles). In this example, both types of particles emit in the visible range, but each excited by a different laser.

In certain embodiments, beads may comprise two types of particles, for example, quantum dot particles and up-converting phosphor particles, that emit visible light but that are excited by different wavelengths of light. See, for example, FIG. 10. In certain such embodiments, the quantum dot particles may be excited by a blue laser and the up-converting phosphor particles may be excited by an infrared laser. The quantum dot particles do not luminesce when illuminated with infrared light and the up-converting phosphor particles do not luminesce when illuminated with the blue laser. To evaluate the bead codes, the beads may first be illuminated by the blue laser to excite the quantum dot particles such that the quantum dot codes can be interpreted. The blue laser may then be turned off. Beads may then be illuminated by the infrared laser to excite the up-converting phosphor particles such that the up-converting phosphor codes can be interpreted.

Intensity may also be used as a factor in distinguishing coded beads. In certain embodiments, intensity variations may be accomplished using coded beads that include phosphor particles of a single emission spectrum, but different beads having different probes have phosphor particles with different intensity levels. In certain embodiments, intensity variations may be accomplished by varying the number of phosphor particles of the same wavelength. For example, in certain embodiments, one can use phosphor particles of the same wavelength in different coded beads, and distinguish between the beads by using different numbers of phosphor particles in each code. For example, if a coded bead is given a ternary code (three levels of intensity for each color of phosphor particle), then one color of phosphor particle provides three possible codes, e.g., (1) no label, (2) one label, and (3) two labels. In certain embodiments, if two colors are used with those three levels of intensity, then 9 ternary codes are possible (see the nonlimiting example in FIG. 6C). In certain embodiments, four colors would allow $3^4$, or 81 ternary codes. In certain embodiments, six colors would allow $3^6$, or 729 ternary codes.

Figure 7:
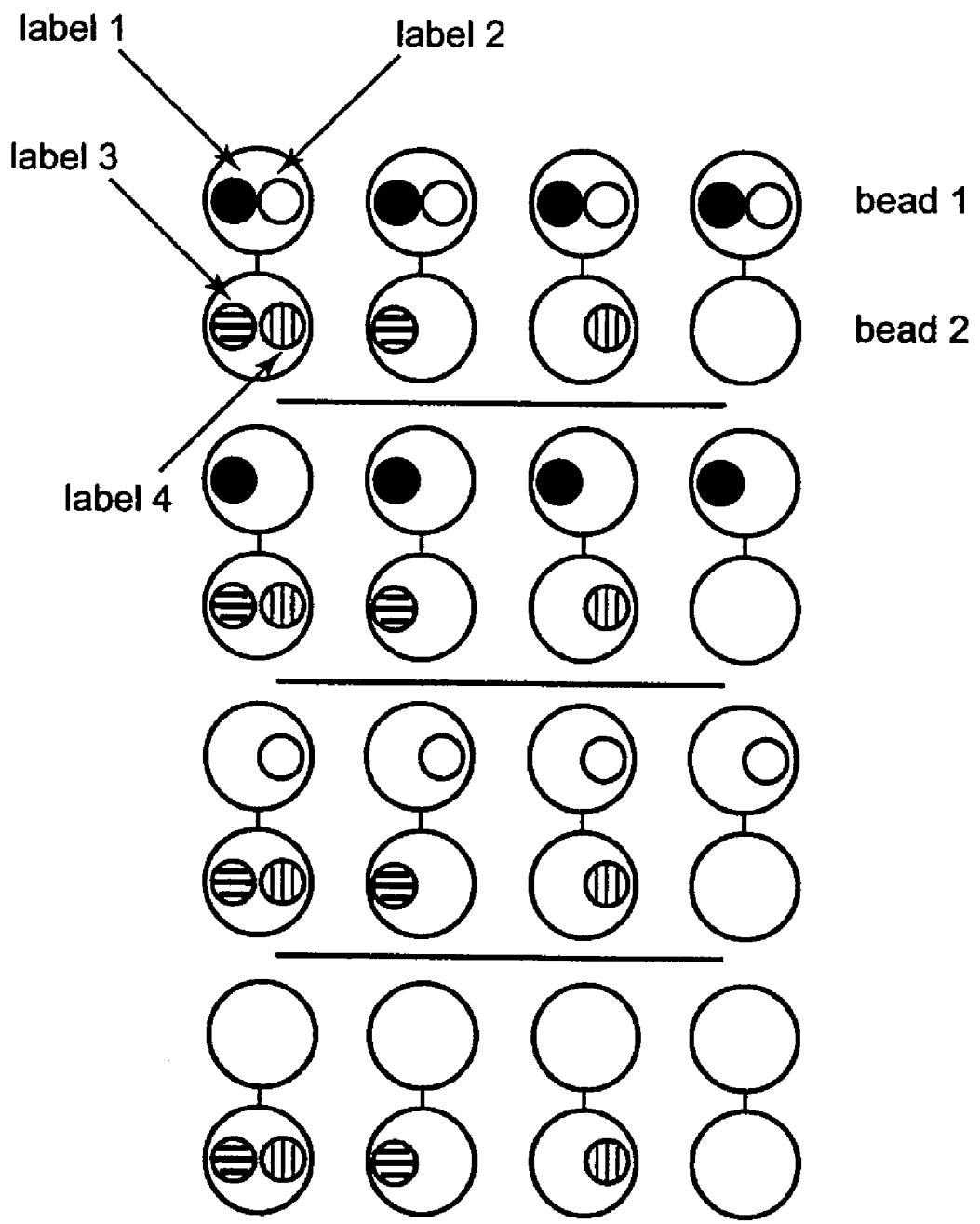
FIG. 7 illustrates certain potential codes using bead pairs. In the nonlimiting example shown in FIG. 7, bead 1 of the bead pair comprises label 1 and label 2, and each label is either present or absent, i.e., each label is binary. Bead 2 of the bead pair comprises label 3 and label 4, and each label is present or absent, i.e., each label is binary.

Further, when coded beads are attached to two different probes of a probe set, the number of potential codes is further multiplied (see the non-limiting example in FIG. 7). For example, in certain embodiments, using two beads per bead set, each of which comprises two labels (e.g., bead 1 comprises label 1 and label 2, and bead 2 comprises label 3 and label 4), where each label is present or absent, i.e., each label is binary, 16 different bead set codes are possible ($4^2$). In certain embodiments, using two different labels in a ternary code per bead, and two beads per bead set (e.g., bead 1 comprises label 1 and label 2, and bead 2 comprises label 3 and label 4), 81 different bead set codes are possible ($9^2$). in certain embodiments, using 4 different labels in a binary code per bead, and two beads per bead set (e.g., bead 1 comprises labels 1, 2, 3, and 4; and bead 2 comprises labels 5, 6, 7, and 8), 256 bead set codes are possible ($16^2$). In certain embodiments, using 10 different labels in a binary code per bead, and two beads per bead set, over 1 million probe set codes are possible ($1,024^2$). In certain embodiments, using 6 different labels in a ternary code, and two beads per bead set, over 500,000 bead set codes are possible ($729^2$).

In certain embodiments, a bead set may comprise more than two beads. In certain embodiments, a bead set comprises three beads. In certain embodiments, two of the beads are each attached to a different target-specific probe. In certain embodiments, at least one of the target-specific probes further comprises an addressable portion. In certain embodiments, the third bead is attached to a probe comprising a complementary addressable portion that is capable of hybridizing to the addressable portion. Addressable portions and complementary addressable portions are described, e.g., in U.S. Publication No. 2003/0165935 A1, which is incorporated by reference herein for any purpose. In certain embodiments, using three different labels in a binary code, and three beads per bead set, 512 bead set codes are possible ($8^3$). In certain embodiments, using six different labels in a ternary code, and three beads per bead set, over 300 million bead set codes are possible ($729^3$).

Exemplary Method of Inverse Emulsion Polymerization

In certain embodiments, beads, microspheres, or dye dots may be made using inverse emulsion polymerization. An exemplary method of making polyacrylamide beads by inverse emulsion polymerization follows.

A solution of 12.022 g (121.28 mmol) dimethylacrylamide (Dajac, containing 75 ppm of monomethyl ether hydroquinone (MEHQ)), 18 g of a 1.5 µM solution of quantum dots (hydrophobic surface-modified, Quantum Dot Corporation) in water; 4.9 mg (0.0132 mmol) EDTA (Aldrich Chemical), and 6.1 mg (0.021 mmol) ammonium persulfate (Aldrich Chemical) is poured into a 500 ml polypropylene beaker containing 80.0 g of mineral oil (certified for Nujol mull, Aldrich Chemical) and 4.0 g Span-80 (sorbital monooleate, Fluka). The mixture is emulsified by stirring at 2,000 rpm for five minutes with a 2" rod-shaped magnetic stir bar. In certain embodiments, phosphors may be used in addition to, or in place of quantum dots. One-tenth of a gram of phosphors is dispersed into 5 g of pH 7 phosphate buffer (Baker) and 0.005 g polyvinyl alcohol (80% hydrolyzed). If used in place of the quantum dots, an additional 13 g of water is added to the dispersed phase solution. If used in addition to the quantum dots, a higher concentration of quantum dot solution may be used to maintain a similar volume of dispersed solution. One skilled in the art can adjust the concentrations and volumes appropriately. One skilled in the art can also select the amount of particles desired for incorporation into beads.

The milky emulsion is transferred into a 500 ml three-necked round bottom flask equipped with a mechanical stirrer having a 2" Teflon stirring blade. The flask is also equipped with a water-cooled condenser, a rubber septum, a bleeding tube for bubbling, and a 12 gauge syringe needle for venting. The mixture is de-oxygenated by bubbling argon through it at a rate of 130 ml/min for 1 hour with constant stirring at 200 rpm. Five µL tetramethylethylenediamine (TEMED, ultra pure, Armesco) is added with a syringe through the rubber septum. With constant stirring at 200 rpm, the reaction flask is then immersed into an oil bath at 40±1° C. for 22 hours. The flask is then removed from the oil bath and air is bubbled into the reaction mixture for 5 minutes with constant stirring at 200 rpm to quench the reaction.

The reaction mixture is then divided into four 50-ml polyethylene centrifuge tubes and centrifuged at 18,000 rpm at 15° C. for 30 minutes. The supernatant is decanted and the pellet is rinsed with n-hexane to remove the mineral oil. The polymer is then vacuum dried at 35° C. overnight to yield 18.0 g of polymer. In order to remove any residual mineral oil, a 5.6 g sample of the polymer is added to 150 ml of acetone and stirred to give a translucent solution. The acetone solution is then poured in a fine stream into 1000 ml of n-hexane with vigorous stirring. The precipitated polymer is rinsed with n-hexane and then vacuum dried at 40° C. for 16 hours to yield 4.6 g of poly(dimethylacrylamide) (PDMA). The molecular weight of the PDMA is then determined by American Polymer Standards Corporation (Mentor, Ohio) using gel permeation chromatograph (GPC) and polyacrylamide internal standards. An exemplary molecular weight is 6,900,000 daltons.

Exemplary Methods of Membrane Emulsion Polymerization

In certain embodiments, beads, microspheres, or dye dots may be made using membrane emulsion polymerization. An exemplary method of making polystyrene beads by membrane emulsion polymerization follows.

All monomers are distilled under reduced pressure prior to use. The dispersed phase is prepared by mixing 4.0 g styrene (38.5 mmol), 0.285 g divinylbenzene (DVB, 2.04 mmol, Aldrich Chemicals), 0.438 g hexadecane (HD, Aldrich Chemicals), and 0.0847 g 2,2'-Azobis(2,4-dimethylvaleronitrile) (Vazo-52, 0.34 mmol, DuPont). The continuous phase is prepared by dissolving 1 g polyvinylalcohol (PVA, 80% hydrolyzed, molecular weight 9-10 kDa, Aldrich Chemicals) and 0.10 g sodium dodecyl sulfate (SDS, USB) in 100 g Milli-Q™-purified water. In certain embodiments, the dispersed phase includes at least one type of label. In certain embodiments, the dispersed phase includes phosphors. In certain embodiments, the dispersed phase includes quantum dots. In certain embodiments, the phosphors and/or quantum dots are hydrophobic surface-modified. One skilled in the art can select the appropriate weight of label included in the reaction in order to achieve the desired bead composition.

The Shirasu Porous Glass (SPG) membrane emulsifier (SPG Technology Co., Japan) is assembled. The membrane tip is wetted by sonication for 3 minutes in water. One hundred and twenty-five ml of the prepared continuous phase is stirred in a 150 ml glass beaker with a ½" stainless steel mechanical stirrer at 300 rpm. The prepared dispersed phase is added to the tank (internal pressurizing chamber) of the membrane micro kit (equipped with 1.1 µm pore size SPG membrane). The membrane is then lowered into the continuous phase. The pressure of the internal pressurizing chamber is increased slowly to a point at which the dispersed phase is forced through the membrane (about 57-60 kPa). The emulsion droplets are removed for size analysis using an optical microscope.

The emulsion prepared from the SPG emulsifier was added to a 250 ml round bottom flask equipped with a mechanical stirrer, a condenser, and a glass bleeding tube for purging the flask with ultra pure nitrogen. One-tenth of a gram of an aqueous solution of $NaNO_2$ (0.09 mmol) is added to the emulsion. The emulsion is then purged with nitrogen at a flow rate of 100 ml/min for 30 minutes and then maintained at constant stream of nitrogen of 30 ml/min. The emulsion was then heated in an oil bath at 70° C. for 17 hours with stirring at 50 rpm.

The resulting slurry solution is then poured into 200 ml of a 50% methanol solution in water and stirred for 5 minutes. The polystyrene beads are collected by centrifugation and washed twice with 40 ml of a 50% methanol solution in water. Twenty-five ml of a 0.5% PVA (80% hydrolyzed) solution in water is added and the mixture sonicated for 10 minutes. Th PVA solution washing is repeated until the beads are free of debris. The beads are then washed with 40 ml of a water/methanol (4:1 v/v) solution twice, and then with 40 ml of methanol twice. The resultant 4-5 µm beads are then suspended in water and may be stored in a refrigerator prior to use.

An exemplary method of making magnetic polystyrene beads by SPG membrane emulsification polymerization follows.

Heptane-based $Fe_3O_3$ colloids (Ferrofluid (80% solid) from Ferrotec Corp.) are dried under vacuum prior to weighing. The dispersed solution is prepared as follows. A mixture of 3.8 g styrene (36.5 mmol), 0.262 g DVB (2.01 mmol), 0.0234 g HD, 0.169 g methacrylic acid (MAA, 1.96 mmol, Aldrich Chemicals), and 0.0295 g PS/PAA (poly (styrene-b-acrylic acid), Polymer Source) is added to 0.029 g dry $Fe_3O_3$ colloids. The mixture is sonicated for 15 minutes to give a dark red solution. Benzoyl perozide (BPO, 0.0889, 0.367 mmol; Aldrich Chemical) is then added. The continuous phase is prepared by dissolving 7.84 g PVA and 0.39 g SDS in 600 g Milli-Q™-purified water.

The membrane micro kit is assembled. The membrane tip is wetted by sonication for 3 minutes in water. One hundred and twenty-five ml of the prepared continuous phase is added to a 150 ml glass beaker. The pH of the continuous phase is adjusted to 3.0 using a 20% solution of sulfuric acid. The dispersed phase is then added to the tank (internal pressurizing chamber). The membrane is lowered into the continuous phase, which is stirred with a ½" stainless steel mechanical stirrer at 300 rpm. Pressure in the internal pressurizing chamber is increased slowly to a point at which the dispersed phase is forced through the membrane (about 35-33 kPa). The emulsion droplets are then removed for size analysis using an optical microscope.

The polymerization procedure is then carried out in a manner similar to that described above for making polystyrene beads using membrane emulsion polymerization. The beads are also washed as described above. The resulting magnetic polystyrene beads are about 4-6 µm in size.

Non-limiting exemplary membrane emulsion polymerization is described, e.g., in Ma, *Macromol. Symp.*, 179: 233-240 (2002); Chu et al., *Langmuir*, 18: 1856-1864 (2002); Omi et al., *Macromol. Symp.*, 151: 319-330 (2000); Kiatamjourwong et al., *Chinese J. Polym. Sci.*,18: 309-322 (2000); Yuyama et al., *Colloids and Surfaces A*, 168: 159-174 (2000); Tong et al., *J. Surfactants and Detergents*, 3: 285-293 (2000); Nagashima et al., *Colloids and Surfaces A*, 153: 221-227 (1999); Nagashima et al., *Colloid and Surfaces A*, 11: 47-56 (1988); Schroder et al., Colloids and Surfaces A, 152: 103-109 (1999); Joscelyne et al., *J. Food Eng.*, 39: 59-64 (1999); Sotoyama et al., *J. Food Sci.*, 64: 211-215 (1999); Omi et al., *Colloids and Surfaces A*, 153: 373-381 (1999); Ha et al., *Colloid and Surfaces A*, 145: 281-284 (1998); Ma et al., *J. Appl. Polym. Sci.*, 66: 1325-1341 (1997); Muramatsu et al., *J. Microencapsulation*, 15: 715-723 (1998); and Omi, *Colloid and Surfaces A*, 109: 97-107 (1996); which are incorporated by reference herein for any purpose.

Exemplary Methods of Dispersion Polymerization

In certain embodiments, beads, microspheres, or dye dots may be made using dispersion polymerization. An exemplary method of making polystyrene beads by dispersion polymerization follows.

A solution is prepared by dissolving 0.453 g polyvinylpyrrolidone K30 (PVP K30, molecular weight 40,000 Da, Fluka), 0.033 g 2,2'-azobisisobutyronitrile (AIBN, 0.20 mmol, Aldrich Chemicals), and 0.048 MAA (0.556 mmol) in 21.3 g absolute ethanol. The solution is added to a 250 ml round bottom flask equipped with a mechanical stirrer with a 2" Teflon stirring blade, a condenser, and a glass bleeding tube for purging with ultra pure nitrogen. The solution is purged with nitrogen for 30 minutes at about 100 ml/min and then maintained at about 30 ml/min nitrogen. The flask is placed into an oil bath at 70° C. and stirred at 100 rpm for 24 hours. The resulting polystyrene beads are poured into 200 ml of methanol and collected by centrifugation. The beads are washed three times with 45 ml methanol and then dried under vacuum. The resulting beads are about 1 µm in size.

Dispersion polymerization is described, e.g., in Kiathamjourwong et al., *Colloids and Surfaces A*, 153: 229-240 (1999); Horak et al., *J. Polym. Sci.: Part A: Polym. Chem.*, 33: 2329-2338 (1995); Hattori, et al., *J. Appl. Polym. Sci.*, 50: 2027-2034 (1993); Christopher et al., *Macromolecules*, 20: 268-273 (1987); Tseng et al., *J. Polym. Sci.: Part A: Polym. Chem.*, 24: 2995-3007 (1986); Kawaguchi et al., *Makromol. Chem., Rapid Commun.*, 6: 315-319 (1985); Almog et al., *Ind. Eng. Chem. Prod. Res. Dev.*, 21: 163-170 (1982); Papir et al., *J. Paint Tech.*, 42: 571-578 (1970); which are incorporated by reference herein for any purpose.

Exemplary Surface Modification of Beads

In certain embodiments, the surface of a bead is modified. In certain embodiments, surface modification facilitates conjugation of a molecule or molecules. In certain embodiments, surface modification facilitates conjugation of biomolecules, including, but not limited to polynucleotides and polypeptides.

In certain embodiments, surface modification involves tethering functional groups to the surface of the bead through a linker so that they generally remain at a distance from the bead surface. In certain embodiments, such tethering through a linker improves the kinetics of conjugation through those functional groups. In certain embodiments, tethering functional groups through a linker to the surface of the bead increases the density of probes that can be conjugated through those functional groups. In certain embodiments, such increased density results in increased sensitivity of detection.

In certain embodiments, surface modification decreases passive adsorption of certain molecules to the surface of the beads. In certain embodiments, by grafting hydrophilic polymers, including, but not limited to, at least one of polyethylene oxide and polyacrylamide, passive adsorption of hydrophilic molecules is reduced. In certain embodiments, by grafting hydrophilic polymers to the surface of the bead, passive adsorption of biomolecules, including, but not limited to, polynucleotides and polypeptides, is reduced. In certain embodiments, by reducing passive adsorption, the signal to noise ratio is reduced and the sensitivity of detection is increased.

Certain exemplary embodiments of surface modification of beads are shown in FIGS. 15-20. In certain embodiments, the grafted polymers form a hydrophilic shell on the surface of a polystyrene bead. In certain embodiments, tethered carboxylate groups may be used for conjugation of certain biomolecules, such as polynucleotides and polypeptides, to the surface of the bead. In certain embodiments, the remaining unreacted hydroxyl groups on the surface of the bead reduce passive adsorption of the biomolecules, increasing the availability of the biomolecules for detection in the assay. In certain embodiments. by increasing the availability of the biomolecules in the assay, the signal to noise ratio may be increased, thereby increasing the sensitivity of the assay.

FIG. 15 shows a non-limiting exemplary surface modification of polystyrene beads using free radical polymerization. In certain embodiments, the surface modification exemplified in FIG. 15 may be used for other types of beads, e.g., nylon beads, polypropylene beads, and/or polyethylene beads. The polystyrene beads are hydroxylated in an aqueous solution of ammonium persulfate (APS) at elevated temperature. Surface modification is then carried using acrylamide and ω-carbonyl(polyethylene oxide)acrylate, molecular weight 3400 (Nektar) in the presence of Ceric (IV)ammonium nitrate in an aqueous solution. See, e.g., Bamford et al., *Macromol. Rapid Commun.*, 14: 379-384 (1994); Bamford et al., *Polymer*, 35: 2844-2852 (1994); Bamford et al., *Polymer*, 37: 4885-4889 (1996); Jabloner et al., *J. Polym. Sci.: A*1, 10:793 (1972); and U.S. Pat. Nos. 3,401,049; 3,698,931; 3,880,580; and 4,810,567; which are incorporated by reference herein for any purpose.

FIG. 16 shows a non-limiting exemplary surface modification of polystyrene beads using Michael addition. Amino groups are introduced onto the surface of the beads by surface nitration with nitric acid and subsequent hydrogenation. The amino groups are then reacted with acrylamide and ω-carboxyl(polyethylene oxide)acrylate, molecular weight 3400 (Nektar). The residual amino groups may be capped, e.g., with an acid anhydride such as acetic anhydride. In certain embodiments, the free amino groups can be converted to free thiol groups by one skilled in the art prior to carrying out the Michael addition reaction, thereby increasing the yield of the Michael addition reaction.

FIG. 17 shows a non-limiting exemplary surface modification of polystyrene beads using ionic interaction. The surface of the bead is chloromethylated, e.g., by addition of chloromethyloctyl ether and a catalyst. A non-limiting exemplary catalyst is $SnCl_4$. The surface is then quaternized with a trialkyl amine such as trimethylamine. The resulting positively-charged beads are then coated with a negatively-charged polymer such as a terpolymer prepared by copolymerization of acrylic acid, styrene sulfonic acid, and N,N'-dimethylacrylamide (or acrylamide). The resulting surface-modified bead will have free carboxylic acid groups for conjugation. In certain embodiments, the unconjugated free carboxylic acid groups will reduce passive adsorption of certain biomolecules including, but not limited to, polynucleotides.

FIG. 18 shows a non-limiting exemplary method of surface modification using atomic transfer radical polymerization (ATRP). Amino groups are introduced onto the surface of the beads by surface nitration with nitric acid and subsequent hydrogenation. The surface amino groups are then acylated with 2-bromoisobutyryl bromide. Atom transfer radical polymerization is then initiated, e.g., by a catalyst such as copper 2,2'-dipyridyl chloride to graft acrylamide, N,N-dimethylacrylamide, and/or ω-carboxyl(polyethylene oxide)acrylate, molecular weight 3400 (Nektar), onto the surface of the bead. See, e.g., Truelsen et al., *Polym. Prepr.*, 43: 49 (2002); Jayachandran et al., *Polym. Prepr.*, 43: 65 (2002); and Husson et al., *Polym. Prepr.*, 43: 67 (2002); which are incorporated by reference herein for any purpose. In certain embodiments, the thickness of the grafted polymer can be controlled in order to produce an acrylamide shell over the polystyrene bead core.

In certain embodiments, other living free radical polymerization techniques may be used. Exemplary free radical polymerization techniques include, but are not limited to, reversible addition chain transfer (RAFT) and tetramethylpiperidine-N-oxide (TEMPO)-initiated polymerization. RAFT is described, e.g., in Chong et al., *Macromolecules*, 32: 2071-2074 (1999); Chiefari et al., *Macromolecules*, 31: 5559-5562 (1998); and Donovan et al., *Polym. Prep.* 40: 281-282 (1999); which are incorporated by reference herein for any purpose. TEMPO is described, e.g., in Hawker, *Acc. Chem. Res.*, 30, 373-382 (1997), which is incorporated by reference herein for any purpose.

FIG. 19 shows a non-limiting exemplary surface modification of polystyrene beads using living radical polymerization. The surface of the bead is chloromethylated, e.g., using chloromethyloctyl ether in the presence of a catalyst such as $SnCl_4$. Following chloromethylation, acrylamide; N,N-dimethylacrylamide; acrylic acid; poly(ethylene glycol)methyl ether acrylate; ω-carboxyl(polyethylene oxide) acrylate, molecular weight 3400 (Nektar); or a combination thereof may be grafted onto the surface of the bead in the presence of a catalyst such as, for example, copper 2,2'-dipyridyl chloride. See, e.g., Wang et al., *Macromolecules*, 28: 7901-7910 (1995);.Li et al., *Polym. Prepr.*, 40: 250 (1999); Rademacher et al., *Polym. Prepr.*, 40: 255 (1999); Huang et al., *Macromolecules*, 32: 1694-1696 (1999); which are incorporated by reference herein for any purpose.

FIG. 20 shows a general non-limiting exemplary approach for modifying the surface of beads using poly (ethylene oxide) having various modifications. Certain non-limiting exemplary R groups are shown in FIG. 20. Certain non-limiting exemplary A and B groups are shown in FIG. 20. One skilled in the art can select appropriate R, A, and B functionalities for conjugating a selected molecule or molecules to the bead. A non-limiting exemplary scheme is as follows. The surface of the bead is first modified to create surface thiol groups, e.g., by first making surface amino groups, and then converting to thiol groups according to methods known in the art. The surface thiol groups are then reacted, e.g., with an acryloxyl group (where A is $CH_2=CH-CO_2$) to form a Michael Addition adduct containing an aldehyde, carboxylic, or NHS-ester (i.e., B is —CHO, —$CO_2H$, or —$CO_2NHS$). In certain embodiments, that adduct is capable of being conjugated to a 3'- or 5' amino group of an oligonucleotide.

Counting Beads and Digital Detection

In certain embodiments, the number of coded beads is counted, which refers to the actual counting of individual beads. Counting the number of beads is distinguishable from analog signal detection, where an aggregate level of signal from multiple beads is detected. Analog signal detection typically uses integration of signals from multiple labels of the same type to determine the number of such labels present in a sample. For example, analog detection typically provides an estimate of the number of beads of a given type by comparing the brightness or level of intensity of the signal in the test sample to the brightness or level of intensity of the signal in controls with known quantities of the given beads.

Counting, by contrast, is a digital detection system in which the number of individual beads is actually counted. Thus, in certain embodiments, if 200 of the same beads are present in a sample, each of those beads is counted. In contrast, to determine the number of beads in a sample with analog detection, the aggregate signal from the 200 beads is measured and compared to the aggregate signal from known quantities of beads.

In certain embodiments, the number of beads counted may be within 20% of the actual number in the sample. In certain embodiments, the number of beads counted may be within 10% of the actual number in the sample. In certain embodiments, the number of beads counted may be within 50% of the actual number in the sample. In certain embodiments, a representative portion of the beads present in a sample are counted, and the total number of beads in the sample is extrapolated from the number of beads counted in the representative portion.

Certain exemplary counting and digital detection methods have been described, for example, in U.S. application Ser. No. 10/302,688.

In certain embodiments involving the actual counting of beads, digital detection may be less influenced by background "noise" or incidental light than analog detection.

In certain embodiments, one may determine fine distinctions between different numbers of beads in different samples by counting the number of beads. In contrast, the aggregate signal from multiple beads in analog detection, in certain instances, may be affected by the variable amount of background signal in different samples, which may obscure small differences in the number of beads in different samples.

In certain embodiments where two or more detectably different beads are being detected in a sample, possible inaccuracies due to overlapping signals from detectably different beads may be minimized by detecting each of the beads separately. In certain analog detection methods, part of the signal from one bead may be detected as signal from another different bead, which may result in an inaccurate reading. This may particularly be the case if the signals from the different beads have overlapping emission ranges. By counting the individual beads rather than measuring aggregate signal intensities, in certain embodiments, inaccuracies that may sometimes result from such overlapping emission ranges may be minimized.

Internal References

In certain embodiments, a bead contains an internal reference. In certain embodiments, the internal reference is detectably different from the code. In certain embodiments, one may use an internal reference to confirm the number of beads with a particular code. For example, in certain embodiments, beads with different codes will each include the same internal reference that can be used to identify the presence of a single bead. In certain embodiments, in order to distinguish a single first bead with a first code from two beads with second codes that have a combined intensity similar to the intensity of the first code of the first bead, a single internal reference in each bead may be included. In certain embodiments, detection of two internal references would indicate the presence of two beads, while detection of a single internal reference would indicate the presence of a single bead. Thus, in certain embodiments, internal references assist in accurate determination of the number of beads actually present when detection of codes alone may provide ambiguous results.

In certain embodiments, the internal reference may be one or more phosphor particles or a non-phosphor particle label. Exemplary internal references include, but are not limited to, phosphor particles, fluorescent molecules, dyes, radioisotopes, luminescent molecules, quantum dots, and other nanoparticles, including, but not limited to, gold particles, resonance light scattering particles, and porous silicon smart dust. In certain embodiments, a single quantum dot is used as an internal reference on each bead. In such embodiments, the presence of a single quantum dot may be used to indicate the presence of a single bead, while the presence of two quantum dots would indicate the presence of two beads, and so forth.

As another nonlimiting example, in certain embodiments, an internal reference may provide a color signal that is detectably different from the signal of the codes. In certain embodiments, the signal from the internal reference for each bead will have an intensity that can be used to identify the presence of a single bead. For example, in certain embodiments, the internal reference signal for each bead will provide a red signal with an intensity of about one unit. In certain such embodiments, one may employ two different codes on two different beads to detect two different targets. For example, in certain embodiments the first code for a first target provides a green signal having an intensity of one unit, and the second code for a second target provides a green signal having an intensity of two units. Without an internal reference, in certain embodiments, one may have difficulty determining whether a green signal having an intensity of two units indicates the presence of two beads for the first target or the presence of one bead for the second target. In certain embodiments that employ the red internal reference, the detection of a red signal with an intensity of one unit will indicate the presence of one bead for the second target, and the detection of a red signal with an intensity of two units will indicate the presence of two beads for the first target.

When beads of varying size are employed, the number of phosphor particles incorporated into such beads may vary according to the size of the bead. In certain embodiments, the inclusion of an internal reference in beads may be used to normalize variations in phosphor signal caused by variations in bead size.

In certain embodiments that do not-employ an internal reference, one tries to use beads of fairly uniform size to try to avoid differences in signal from the same code due to the difference in the sizes of the beads. In certain embodiments, an internal reference on the beads may permit one to use beads of varying size. In certain such embodiments, one may employ two different codes on two different beads to detect two different targets. For example, if the beads have a diameter of X, the first code for a first target provides a green signal having an intensity of one unit, and the second code for a second target provides a green signal having an intensity of two units. Without an internal reference, in certain embodiments with beads of varying size, one may have difficulty determining whether a bead providing a green signal having an intensity of two units indicates the presence of a bead for the first target having a diameter larger than X or the presence of a bead for the second target having a diameter X.

In certain such embodiments, one may employ beads that include an internal reference that is detectably different from the phosphor particles emitting the codes. In certain embodiments, one may employ an internal reference that provides a red signal having an intensity of one unit if the bead has a diameter of X. Thus, if the bead size varies from the diameter of X, the internal reference will provide a different intensity than one unit. In certain such embodiments, the detection of a bead with a green signal of two units indicates the presence of the second target if the red signal is one unit and indicates the presence of the first target if the red signal is two units.

In certain embodiments, the use of an internal reference may allow one to produce beads of smaller sizes than is practical without the use of an internal reference. In certain embodiments, beads may be less than 2 μm in diameter. In certain embodiments, using an internal reference, one may be able to distinguish very small differences in bead size.

In certain embodiments, the use of an internal reference could be used when counting beads by staging or by flow cytometry. In certain embodiments, beads employing an internal reference may be used in an array, wherein analytes are bound to specific regions of the array. In certain embodiments, arrays with beads with internal references may be imaged. In certain embodiments, software may be used to normalize signals using the internal references in digitalized images.

In certain embodiments, the size of a bead may be used as a coding element. As a non-limiting example, beads have 100 different codes employing two colors. In certain embodiments, different sized beads may be used as part of the code, because different sized beads provide different intensities. For example, in certain embodiments, the 100 codes using two colors may be increased to 400 codes by using four different sized beads.

Detection Methods

In certain embodiments, the present invention provides for the detection of beads. In certain embodiments, the present invention provides for the counting of beads. Several methods of bead detection and/or counting are envisioned, and one of skill in the art will appreciate the variety of methods by which one could detect and/or count beads.

As discussed above, counting of beads refers to the actual counting of individual beads. In certain embodiments, detection and/or counting further includes identifying the code of a coded bead if multiple different codes are employed in the different beads.

In certain embodiments, beads are detected with a type of flow cytometry, such as a Fluorescence Activated Cell Sorter (FACS), a Luminex™ detection device, or a similar technology developed for the detection of single beads. In certain embodiments, beads are resolved by electrophoresis and detected during or after electrophoretic migration of the beads. Electrophoresis includes, but is not limited to, capillary electrophoresis and field electrophoresis. In certain embodiments, detection involves a device that excites the phosphor particles (such as a laser, as a non-limiting example) and a scanning device that counts the coded beads.

In certain embodiments, static methods of detection are employed. In certain embodiments, such methods involve placing the beads on a plate (as a non-limiting example), exciting the beads with one or more excitation sources (such as lasers of different wavelengths, for example) and running a scanning device across the plate in order to count the beads. In certain embodiments, the plate is moved back and forth across the field of detection of the scanning device. In certain embodiments, the beads are attached to the plate or slide. In certain embodiments, a camera images the entire field, and the image is scanned in order to count the beads.

Certain Exemplary Methods of Target Detection

In certain embodiments, methods of detecting targets are provided. In certain embodiments, probe sets comprising coded beads are provided for the detection of targets. In certain embodiments, methods of detecting targets employ probe sets comprising two or more probes, wherein the two or more probes are attached to different coded beads, wherein the different coded beads comprise detectably different codes. In certain embodiments, methods of detecting targets employ probe sets comprising two or more probes, wherein at least one probe is attached to a coded bead and at least one probe is attached to a separating moiety.

In certain embodiments in which the targets are nucleic acid sequences, the sequence-specific portions of the probes are of sufficient length to permit specific annealing to complementary sequences in target sequences. In certain embodiments, the length of the sequence-specific portion is 6 to 35 nucleotides. Detailed descriptions of probe design that provide for sequence-specific annealing can be found, among other places, in Diffenbach and Dveksler, PCR Primer, A Laboratory Manual, Cold Spring Harbor Press, 1995, and Kwok et al. (Nucl. Acid Res. 18:999-1005, 1990).

In certain embodiments, a probe set according to the present invention comprises a first target-specific probe and a second target-specific probe that adjacently hybridize to the same target sequence. A sequence-specific portion of the first target-specific probe in each probe set is designed to hybridize with the downstream region of the target sequence in a sequence-specific manner (see, e.g., probe A in FIG. 8). A sequence-specific portion of the second target-specific probe in the probe set is designed to hybridize with the upstream region of the target sequence in a sequence-specific manner (see, e.g., probe Z in FIG. 8). The sequence-specific portions of the probes are of sufficient length to permit specific annealing with complementary sequences in target sequences, as appropriate. Under appropriate conditions, adjacently hybridized probes may be ligated together to form a ligation product, provided that they comprise appropriate reactive groups, for example, without limitation, a free 3'-hydroxyl or 5'-phosphate group. In certain embodiments, the reaction is part of an oligonucleotide ligation assay (OLA). OLA is described, e.g., in U.S. Publication No. 2003/0165935 A1, which is incorporated by reference herein for any purpose.

Figure 9:
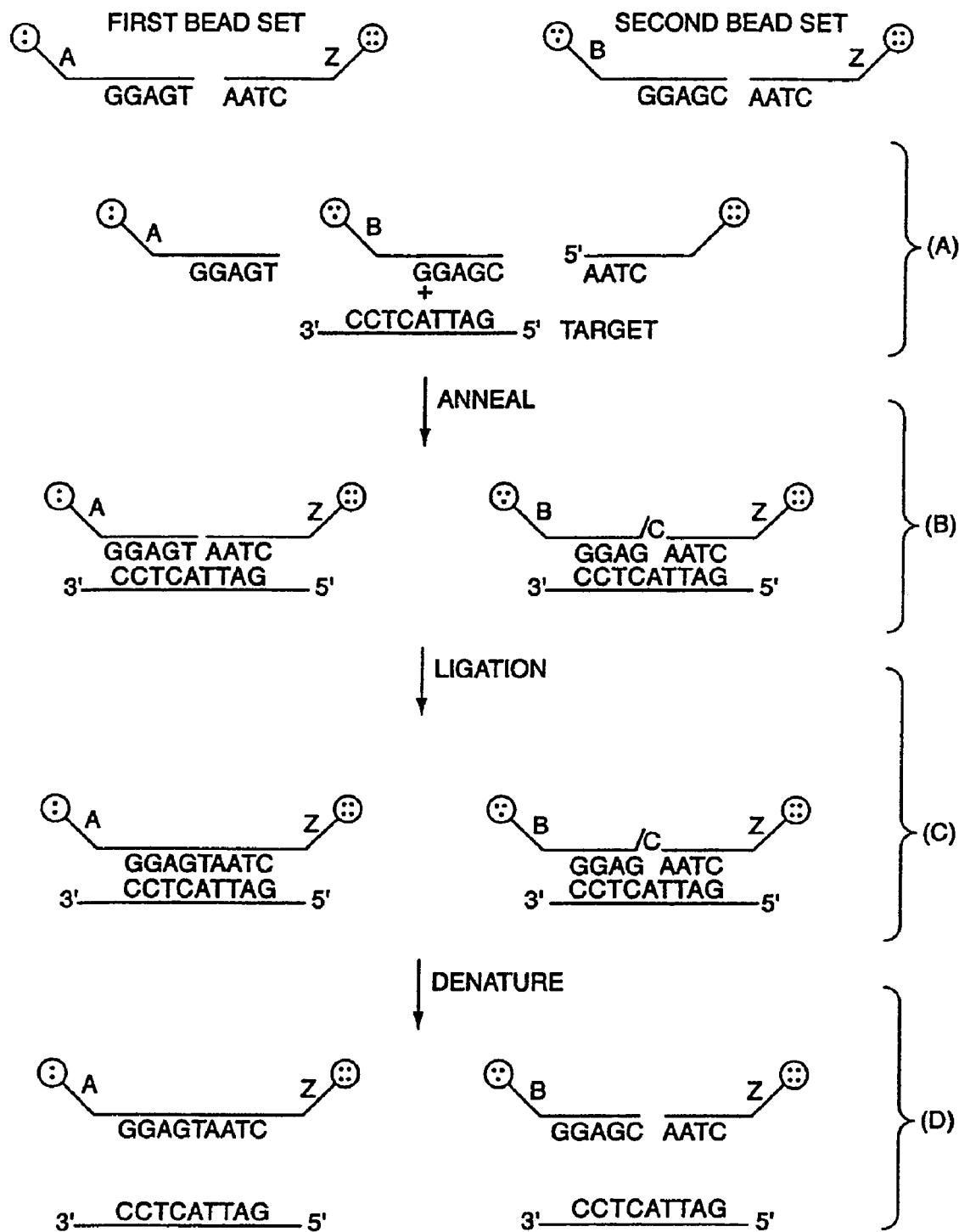
FIG. 9 illustrates methods for differentiating between two potential alleles in a target locus using certain embodiments of coded beads attached to probe sets.

In certain embodiments, two different probe sets may be used to determine the presence or absence of, or to quantitate, two different target sequences that differ by one or more nucleotides (see, e.g., FIG. 9). According to certain embodiments of the invention, a probe set is designed so that the sequence-specific portion of the first target-specific probe will hybridize with the downstream target region (see, e.g., probe A in FIG. 8, and probes A and B in FIG. 9) and the sequence-specific portion of the second target-specific probe will hybridize with the upstream target region (see, e.g., probe Z in FIG. 8 and FIG. 9). In certain embodiments, a nucleotide base complementary to the pivotal nucleotide, the "pivotal complement," is present on the proximal end of either the first target-specific probe or the second target-specific probe of the probe set (see, e.g., 3' end of probe A in FIG. 8, and the 3' end of probes A and B in FIG. 9). In certain embodiments, the first probe may comprise the pivotal complement rather than the second probe. The skilled artisan will appreciate that, in various embodiments, the pivotal nucleotide(s) may be located anywhere in the target sequence and that likewise, the pivotal complement(s) may be located anywhere within the target-specific portion of the probe(s). For example, according to various embodiments, the pivotal complement may be located at the 3' end of a probe, at the 5' end of a probe, or anywhere between the 3' end and the 5' end of a probe. Also, one or more pivotal complements may be located on both probes of a probe set In certain embodiments, when the first and second target-specific probes of the probe set are hybridized to the appropriate upstream and downstream target regions, and when the pivotal complement is at the 5' end of one probe or the 3' end of the other probe, and the pivotal complement is base-paired with the pivotal nucleotide on the target sequence, the hybridized first and second target-specific probes may be ligated together to form a ligation product (see, e.g., FIG. 9(B)-(C)). In the example shown in FIG. 9(B)-(C), a mismatched base at the pivotal nucleotide, however, interferes with ligation, even if both probes are otherwise fully hybridized to their respective target regions (see, e.g., FIG. 9(B)-(C)).

In certain embodiments, other mechanisms may be employed to avoid ligation of probes that do not include the correct complementary nucleotide at the pivotal complement. For example, in certain embodiments, conditions may be employed such that a probe of a ligation probe set will hybridize to the target sequence to a measurably lesser extent if there is a mismatch at the pivotal nucleotide. Thus, in such embodiments, such non-hybridized probes will not be ligated to the other probe in the probe set.

In certain embodiments, the first probes and second probes in a ligation probe set are designed with similar melting temperatures ($T_m$). Where a probe includes a pivotal complement, in certain embodiments, the $T_m$ for the probe(s) comprising the pivotal complement(s) of the target pivotal nucleotide sought will be approximately 4-15° C. lower than the other probe(s) that do not contain the pivotal complement in the probe set. In certain such embodiments, the probe comprising the pivotal complement(s) will also be designed with a $T_m$ near the ligation temperature. Thus, a probe with a mismatched nucleotide will more readily dissociate from the target at the ligation temperature. The ligation temperature, therefore, in certain embodiments provides another way to discriminate between, for example, multiple potential alleles in the target.

Further, in certain embodiments, ligation probe sets do not comprise a pivotal complement at the terminus of the first or the second probe (e.g., at the 3' end or the 5' end of the first or second probe). Rather, the pivotal complement is located somewhere between the 5' end and the 3' end of the first or second probe. In certain such embodiments, probes with target-specific portions that are fully complementary with their respective target regions will hybridize under high stringency conditions. Probes with one or more mismatched bases in the target-specific portion, by contrast, will hybridize to their respective target region to a measurably lesser extent. Both the first probe and the second probe must be hybridized to the target for a ligation product to be generated.

In certain embodiments, highly related sequences that differ by as little as a single nucleotide can be distinguished. For example, according to certain embodiments, one can distinguish the two potential alleles in a biallelic locus using two different probe sets as follows. The first target-specific probe of each probe set will differ from one another in their pivotal complement, and the coded beads associated with the two different first target-specific probes will be detectably different (see, e.g., the coded beads with probes A and B in FIG. 9(a)). Each probe set can also comprise identical second target-specific probes. In certain embodiments, each second target-specific probe is associated with an identical coded bead (see, e.g., the coded beads with probe Z in FIG. 9(a)). In certain embodiments, each second target-specific probe is associated with an identical separating moiety.

One can combine the sample with the two different probe sets. In certain embodiments, one of the target-specific probes of each probe set further comprises a separating moiety. In certain embodiments, the separating moiety is attached to, associated with, or embedded in, a bead. All three target-specific probes will hybridize with the target sequence under appropriate conditions (see, e.g., FIG. 9(b)). Only the first target-specific probe with the hybridized pivotal complement, however, will be ligated with the hybridized second target-specific probe (see, e.g., FIG. 9(c)). Thus, if only one allele is present in the sample, only one ligation product for that target will be generated (see, e.g., ligation product A-Z in FIG. 9(d)). Both ligation products (A-Z and B-Z) may be formed in a sample if both alleles are present, e.g., if the sample is from a heterozygous individual. In certain embodiments, ligation of probes with a pivotal complement that is not complementary to the pivotal nucleotide may occur, but such ligation occurs to a measurably lesser extent than ligation of probes with a pivotal complement that is complementary to the pivotal nucleotide. See, e.g., U.S. Publication No. 2003/0165935 A1, which is incorporated by reference herein for any purpose.

In certain embodiments, a probe set comprises a first target-specific probe and a second target-specific probe, as discussed above. In certain embodiments, one of the target-specific probes comprises a separating moiety and one of the target-specific probes comprises an addressable portion. In certain embodiments, a coded bead comprising a probe that comprises a complementary addressable portion, which is capable of hybridizing to the addressable portion, is added to the reaction composition. Addressable portions and complementary addressable portions are described, e.g., in U.S. Publication No. 2003/0165935 A1, which is incorporated by reference herein for any purpose. In certain embodiments, the addressable portion of each different target-specific probe is different. In certain embodiments, different coded beads comprise probes comprising different complementary addressable portions.

In certain embodiments, one of the target-specific probes comprises a coded bead and one of the target-specific probes comprises an addressable portion. In certain embodiments, a separating moiety comprising a probe that comprises a complementary addressable portion is added to the reaction composition. In certain embodiments, the coded bead attached to each different target-specific sequence is different. See, e.g., U.S. Publication No. 2003/0165935 A1, which is incorporated by reference herein for any purpose.

Certain Exemplary Embodiments of Detecting Targets

In certain embodiments, the present invention is directed to methods, reagents, and kits for determining the presence or absence of, or for quantitating, targets in a sample. In certain embodiments, one detects the presence or absence of (or quantitates) target nucleic acid sequences using methods involving ligation.

In certain embodiments, for each target nucleic acid sequence to be detected, a probe set, comprising at least one first target-specific probe attached to a first coded bead and at least one second target-specific probe attached to a second coded bead, is combined with the sample and optionally, a ligation agent, to form a ligation reaction mixture. In certain embodiments, the first coded bead further comprises a first code comprising at least two phosphor particles, and the first code is specific for the first target-specific probe. In certain embodiments, the second coded bead further comprises a second code comprising at least two phosphor particles, and the second code is specific for the second target-specific probe. The first coded bead is detectably different from the second coded bead.

In certain embodiments, the first and second target-specific probes in each probe set are designed to be complementary to the sequences immediately flanking the pivotal nucleotide of a target sequence (see, e.g., probes A, B, and Z in FIG. 9(A)). In certain embodiments, either the first target-specific probe or the second target-specific probe of a probe set, but not both, will comprise the pivotal complement (see, e.g., probe A of FIG. 9(A)). When the target sequence is present in the sample, the first and second target-specific probes will hybridize, under appropriate conditions, to adjacent regions on the target (see, e.g., FIG. 9(B)). When the pivotal complement is base-paired in the presence of an appropriate ligation agent, two adjacently hybridized probes may be ligated together to form a ligation product (see, e.g., FIG. 9(C)).

One can then detect the presence or absence of the target nucleic acid sequences by detecting the presence or absence of the ligation product comprising the appropriate coded beads.

In certain embodiments, including, but not limited to, detecting multiple alleles, the ligation reaction mixture may comprise a different probe set for each potential allele in a multiallelic target locus. In certain such embodiments, each different probe set comprises different coded beads, wherein each coded bead is specific for each target-specific probe In certain embodiments, one may use, for example, without limitation, a simple screening assay to detect the presence of three biallelic loci (e.g., L1, L2, and L3) in an individual using six probe sets. See, e.g., Table 1 below.

TABLE 1

| Locus | Allele | Probe Set - Probe (label) |
|-------|--------|---------------------------|
| L1 | 1 | A (2 red), Z (2 blue) |
|    | 2 | B (4 red), Z (2 blue) |
| L2 | 1 | C (2 orange), Y (4 blue) |
|    | 2 | D (4 orange), Y (4 blue) |
| L3 | 1 | E (2 yellow), X (2 green) |
|    | 2 | F (4 yellow), X (2 green) |

In such embodiments, two different probe sets are used to detect the presence or absence of each allele at each locus. The two first target-specific probes of the two different probe sets for each locus, for example, probes A and B for locus L1, comprise the same upstream sequence-specific portion, but differ at the pivotal complement. Also, the two different probes A and B comprise different coded beads. The two second target-specific probes of the two different probe sets for each locus, for example, probe Z for locus L1, comprise the same downstream sequence-specific portion. Also, the probes Z comprise the same coded bead. (In certain embodiments, at least one of the coded beads of each probe set may further comprise a separating moiety. In certain embodiments, only one of the coded beads of each probe set comprises a separating moiety.)

Thus, in embodiments as depicted in Table 1, the three probes A, B, and Z, are used to detect the two possible L1 alleles, wherein AZ is the ligation product formed if the first L1 allele is present and BZ is the ligation product formed if the second L1 allele is present. Likewise, probes C, D, and Y are used to detect the two possible L2 alleles. Likewise, probes E, F, and X are used to detect the two possible L3 alleles.

After ligation of adjacently hybridized first and second target-specific probes, one can detect the presence or absence of a ligation product for each of the alleles for each of the loci by detecting the presence of absence of the unique combinations of coded beads for each allele. For example, one may detect the following combinations of beads: (1) 2 red/2 blue; (2) 4 orange/4 blue; (3) 2 yellow/2 green; and (4) 4 yellow/2 green. Such an individual would be determined to be homozygous for allele 1 at locus L1, homozygous for allele 2 at locus L2, and heterozygous for both alleles 1 and 2 at locus L3.

The person of ordinary skill will appreciate that in certain embodiments, three or more alleles at a multiallelic locus can also be differentiated using these methods. Also, in certain embodiments, more than one locus can be analyzed in a single reaction.

The skilled artisan will understand that in certain embodiments, the probes can be designed with the pivotal complement at any location in either the first target-specific probe or the second target-specific probe. Additionally, in certain embodiments, target-specific probes comprising multiple pivotal complements are within the scope of the invention.

What is claimed is:

1. A method of determining the identity of at least two coded beads in a mixture, wherein each coded bead comprises a substrate, two or more different phosphor particles, and at least one member of an affinity set, comprising:

a) irradiating at least one bead with at least one irradiating wavelength of light, wherein the at least one irradiating wavelength of light causes at least one phosphor particle to emit at least one emitting wavelength of light;

b) detecting the at least one emitting wavelength of light;

c) optionally repeating (a) and (b) 1 to 20 times, wherein at least one of the at least one irradiating wavelength of light for each repetition is the same or different from at least one of the at least one irradiating wavelength of light for any previous irradiating of the beads, and wherein at least one of the at least one emitting wavelength of light for each repetition is the same or different from at least one of the at least one emitting wavelength of light for any previous emission by a phosphor particle; and d) determining the identity of at least one coded bead.

2. The method of claim 1, wherein at least one of the at least one emitting wavelength of light comprises light in the visible spectrum.

3. The method of claim 1, wherein at least one of the at least one emitting wavelength of light is between 380 nm and 720 nm.

4. The method of claim 1, wherein at least one coded bead comprises two or more different phosphor particles that emit light at wavelengths shorter than a wavelength capable of exciting the two or more different phosphor particles.

5. The method of claim 1, wherein at least one coded bead comprises at least one phosphor particle that emits light at a wavelength shorter than a wavelength capable of exciting the phosphor particle.

6. The method of claim 1, wherein at least one coded bead comprises two or more different phosphor particles that emit light at wavelengths longer than a wavelength capable of exciting the two or more different phosphor particles.

7. The method of claim 1, wherein at least one coded bead comprises at least one phosphor particle that emits light at a wavelength longer than a wavelength capable of exciting the phosphor particle.

8. The method of claim 1, wherein at least one coded bead comprises two or more different phosphor particles comprising:

phosphor particles that emit light at wavelengths shorter than a wavelength capable of exciting the two or more different phosphor particles; and phosphor particles that emit light at wavelengths longer than a wavelength capable of exciting the two or more different phosphor particles.

9. The method of claim 1, wherein the at least one member of an affinity set for each of the at least two coded beads is independently selected from a polynucleotide, a polypeptide, a polysaccharide, streptavidin, biotin, a ligand, an antigen, and an antibody.

10. The method of claim 1, wherein at least one coded bead comprises at least one substrate selected from glass, metal, and an organic polymer.

11. The method of claim 1, wherein at least one coded bead comprises phosphor particles distributed throughout the bead.

12. The method of claim 1, wherein at least one coded bead comprises phosphor particles homogeneously distributed throughout the bead.

13. The method of claim 1, wherein at least one coded bead comprises phosphor particles attached to the surface of the bead.

* * * * *